(12) United States Patent
Volkov et al.

(10) Patent No.: US 6,777,684 B1
(45) Date of Patent: Aug. 17, 2004

(54) SYSTEMS AND METHODS FOR MILLIMETER AND SUB-MILLIMETER WAVE IMAGING

(75) Inventors: Leonid Volkov, Moscow Region (RU); Johan Stiens, Brussels (BE)

(73) Assignee: Rose Research L.L.C., Dallas, TX (US)

( * ) Notice: Subject to any disclaimer, the term of this patent is extended or adjusted under 35 U.S.C. 154(b) by 216 days.

(21) Appl. No.: 09/644,817

(22) Filed: Aug. 23, 2000

Related U.S. Application Data

(60) Provisional application No. 60/150,397, filed on Aug. 23, 1999.

(51) Int. Cl.[7] ............................................. G01N 21/01
(52) U.S. Cl. ..................... 250/341.1; 342/179; 343/915
(58) Field of Search ..................... 250/341.1; 342/179; 343/915

(56) References Cited

U.S. PATENT DOCUMENTS

| | | | |
|---|---|---|---|
| 3,706,928 A | 12/1972 | Beck et al. .................... 325/33 |
| 4,090,204 A | * 5/1978 | Farhat ......................... 343/754 |
| 4,102,037 A | 7/1978 | Espaignol et al. ............. 29/583 |
| 4,197,546 A | 4/1980 | Cachier et al. ............. 343/701 |
| 4,278,951 A | 7/1981 | Cachier et al. ............... 331/96 |
| 4,310,852 A | 1/1982 | Tricoles ...................... 358/110 |
| 4,761,813 A | 8/1988 | Gammel ....................... 380/6 |
| 4,801,848 A | 1/1989 | Birnbach et al. .......... 315/5.41 |
| 4,847,571 A | 7/1989 | Stevance et al. .............. 331/96 |
| 4,866,454 A | 9/1989 | Droessler et al. ........... 343/725 |
| 4,901,084 A | 2/1990 | Huguenin et al. .......... 342/179 |
| 4,910,523 A | 3/1990 | Huguenin et al. .......... 342/179 |
| 4,929,951 A | 5/1990 | Small .......................... 342/179 |
| 5,047,783 A | 9/1991 | Hugenin ...................... 342/179 |
| 5,073,782 A | 12/1991 | Huguenin et al. .......... 342/179 |
| 5,170,169 A | 12/1992 | Stephan ....................... 342/179 |
| 5,172,243 A | 12/1992 | Hayashi et al. ............. 358/400 |
| 5,202,692 A | 4/1993 | Huguenin et al. .......... 342/179 |
| 5,227,800 A | 7/1993 | Huguenin et al. .......... 342/179 |
| 5,455,587 A | 10/1995 | Schneider .................... 342/62 |
| 5,455,590 A | 10/1995 | Collins et al. .............. 342/179 |
| 5,530,247 A | 6/1996 | McIver et al. ........... 250/336.1 |
| 5,537,242 A | 7/1996 | Lim ........................... 359/287 |
| 5,557,283 A | 9/1996 | Sheen et al. ................. 342/179 |
| 5,559,478 A | 9/1996 | Athas et al. ................. 331/117 |
| 5,623,145 A | 4/1997 | Nuss .......................... 250/330 |
| 5,680,139 A | 10/1997 | Huguenin et al. .......... 342/175 |
| 5,710,430 A | 1/1998 | Nuss ........................ 250/358.1 |

(List continued on next page.)

FOREIGN PATENT DOCUMENTS

| | | | |
|---|---|---|---|
| EP | 627634 A2 | 12/1994 |
| EP | 903566 A2 | 3/1999 |
| WO | WO 90/07130 | * 6/1990 |
| WO | WO 99/21148 | 4/1999 |

OTHER PUBLICATIONS

Goldsmith et al, "Focal plane imaging systems for millimeter wavelengths", IEEE Transactions on Microwave Theory and Techniques, vol. 41 No. 10, pp. 1664–1675, Oct. 1993.*
Waves, vol. 5, No. 1 1984, p 91–101.

*Primary Examiner*—Constantine Hannaher
*Assistant Examiner*—Shun Lee
(74) *Attorney, Agent, or Firm*—Slater & Matsil, L.L.P.

(57) ABSTRACT

In one aspect, the present invention provides an apparatus 10 for imaging. At least one source 12 (or 12/14) of composite radiation illuminates a field of view 16. The radiation includes a set of multiple phase-independent partials that are independently controllable and exhibit distinct physical features. A quasi-optical element 21 is disposed between the field of view 16 and a multi-element receiver 18. The multi-element receiver 18 is disposed to receive image radiation 28 from the quasi-optical element 21. Particular ones of the receiver elements transform the image radiation 28 into a set of electrical signals that include information relating to features of the partials.

79 Claims, 49 Drawing Sheets

U.S. PATENT DOCUMENTS

| | | | |
|---|---|---|---|
| 5,737,075 A | 4/1998 | Koch et al. | 356/310 |
| 5,754,945 A | 5/1998 | Lin et al. | 455/33.2 |
| 5,754,949 A | 5/1998 | Kumagai et al. | 455/115 |
| 5,760,397 A | 6/1998 | Huguenin et al. | 250/332 |
| 5,859,609 A | 1/1999 | Sheen et al. | 342/179 |
| 5,949,562 A | 9/1999 | Kubota et al. | 359/124 |
| 5,982,326 A * | 11/1999 | Chow et al. | 342/365 |

* cited by examiner

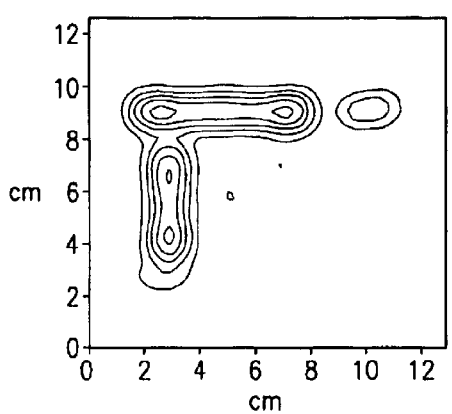
FIG. 4a
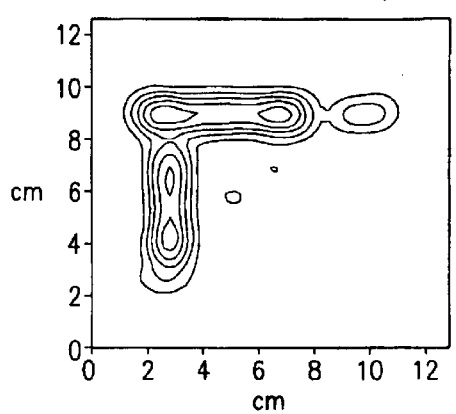
FIG. 4b
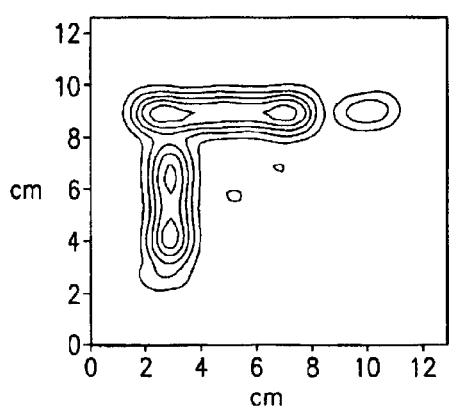
FIG. 4c
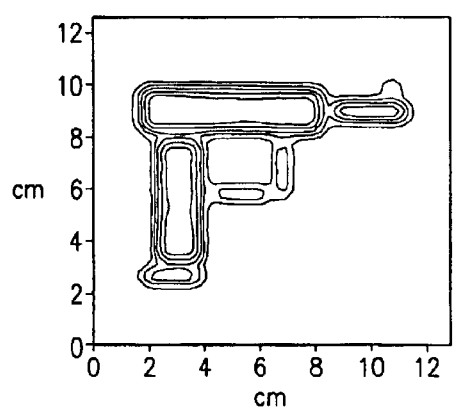
FIG. 4d
FIG. 5a

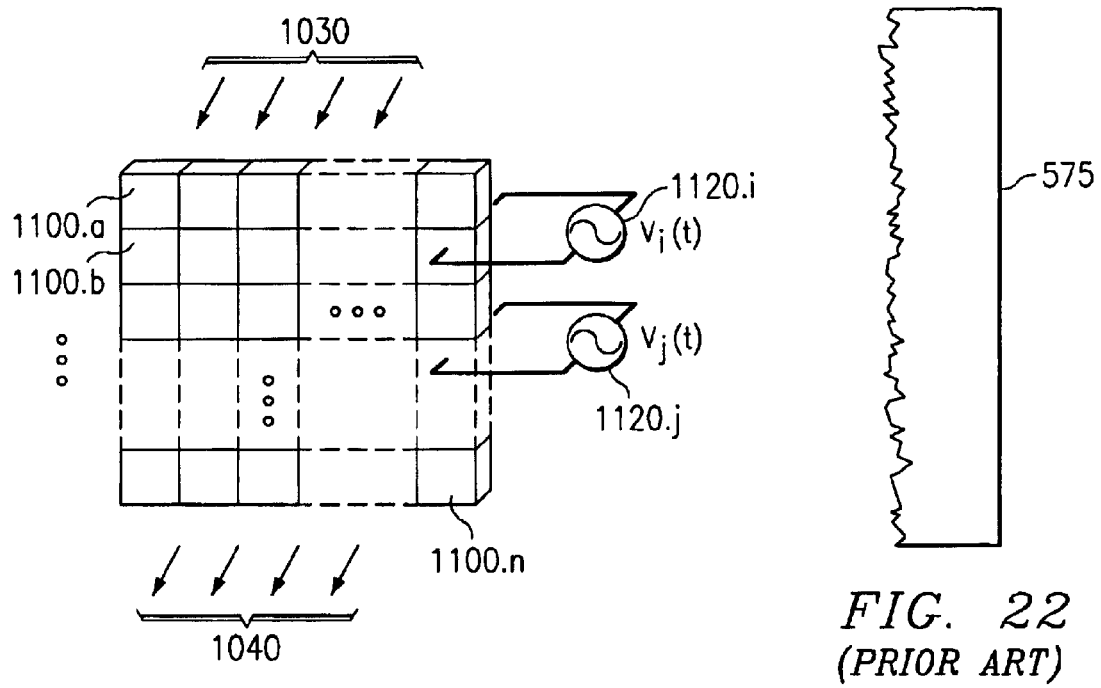
FIG. 21
FIG. 22
(PRIOR ART)
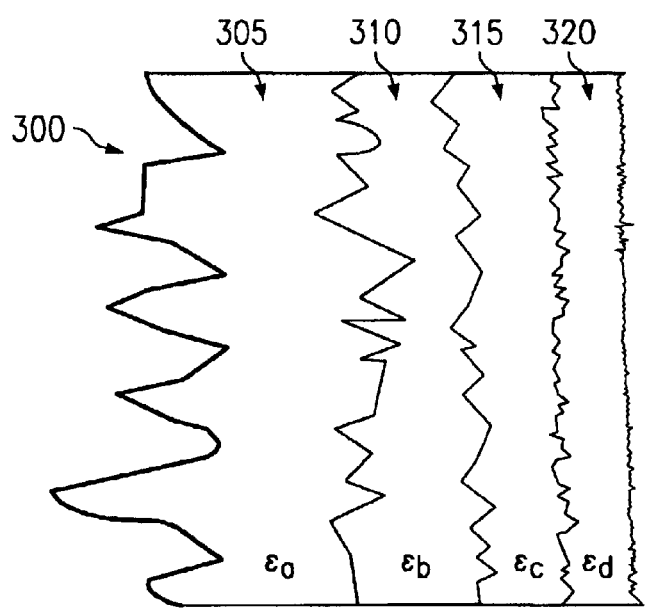
FIG. 23a

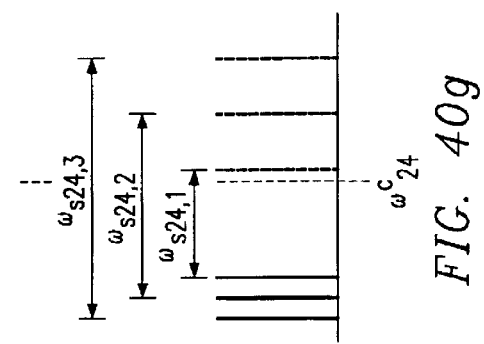
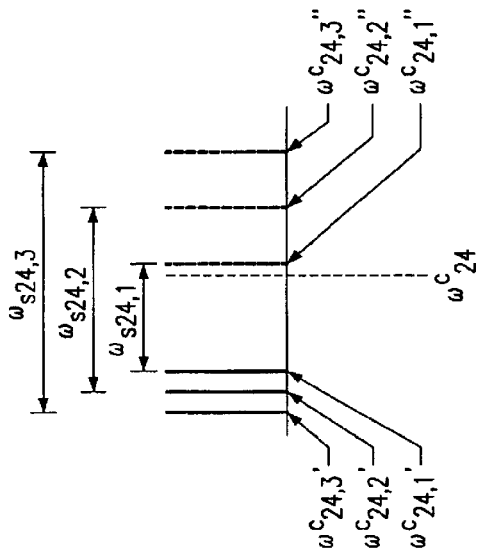
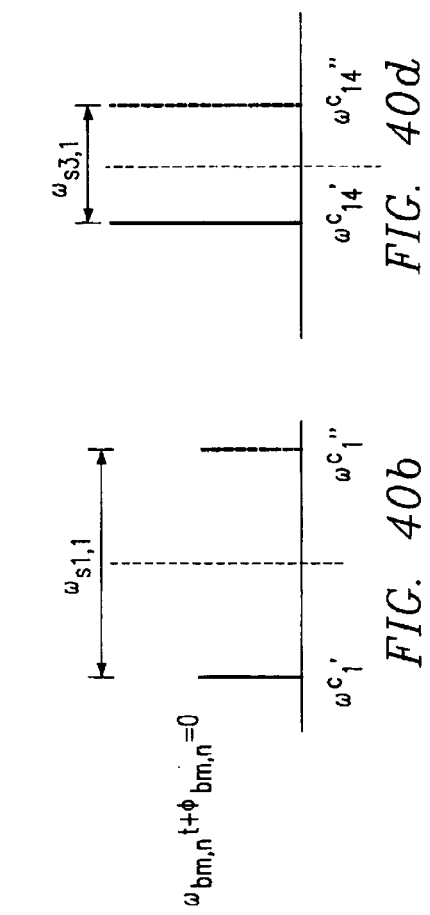
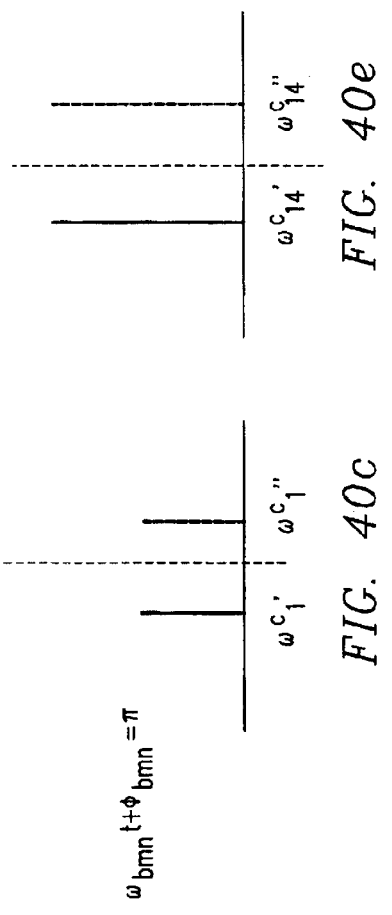
$\omega_{bm,n} = \omega^c{}_{m,n}{}'' - \omega^c{}_{m,n}{}' = \omega_{sm,n} + \omega_{dm,n}\cos(\omega_{m,n}t + \phi_{m,n})$

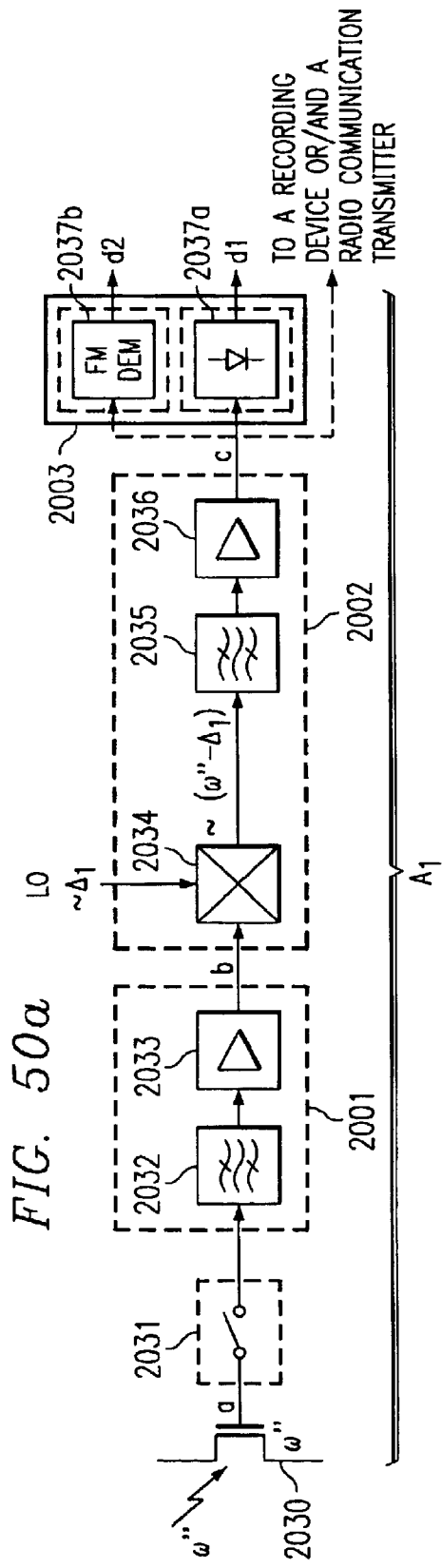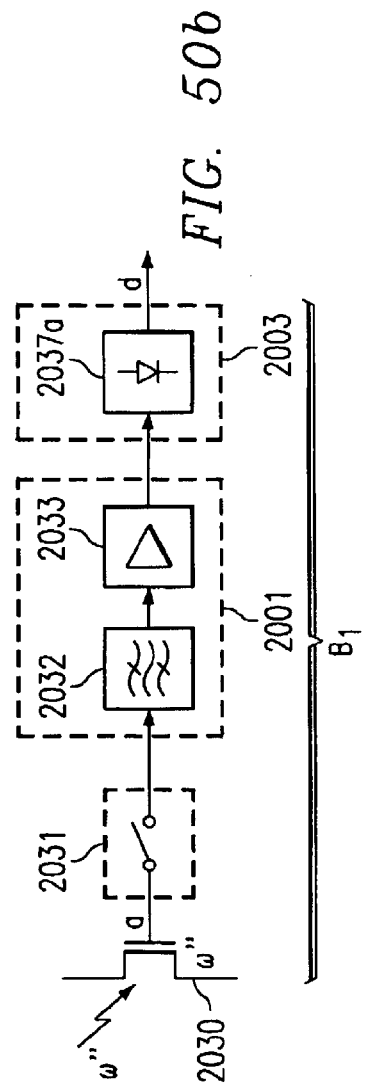

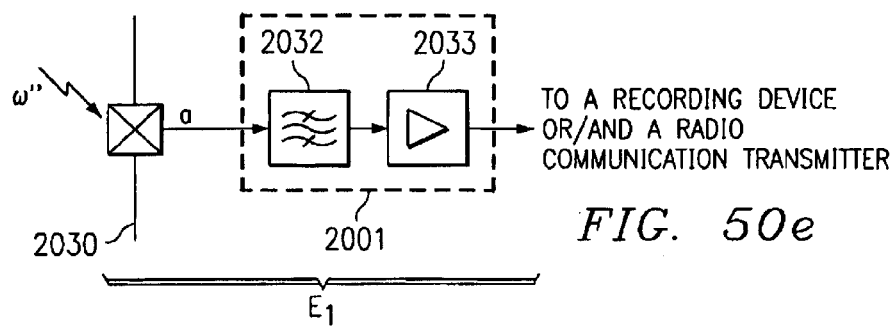
FIG. 50e
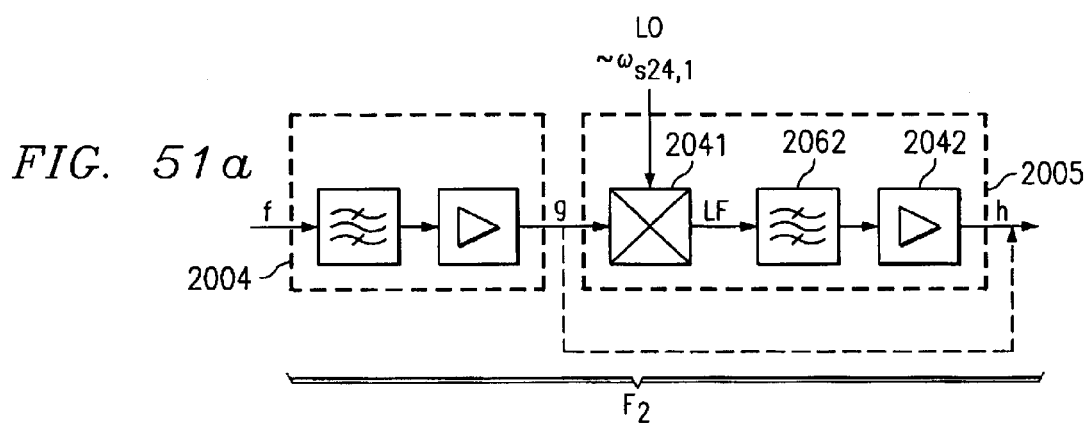
FIG. 51a
FIG. 51b
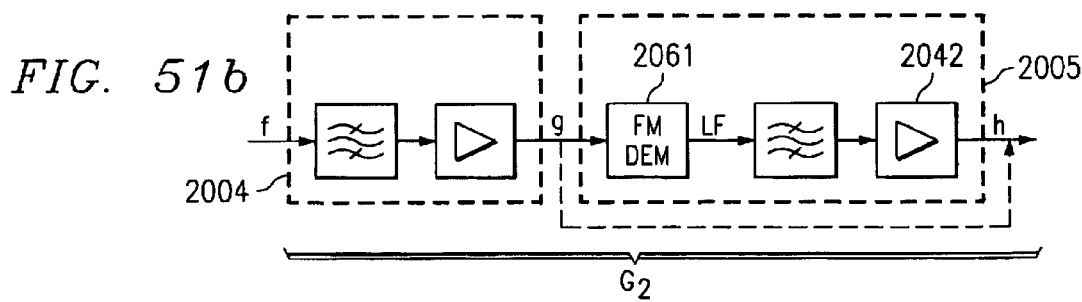
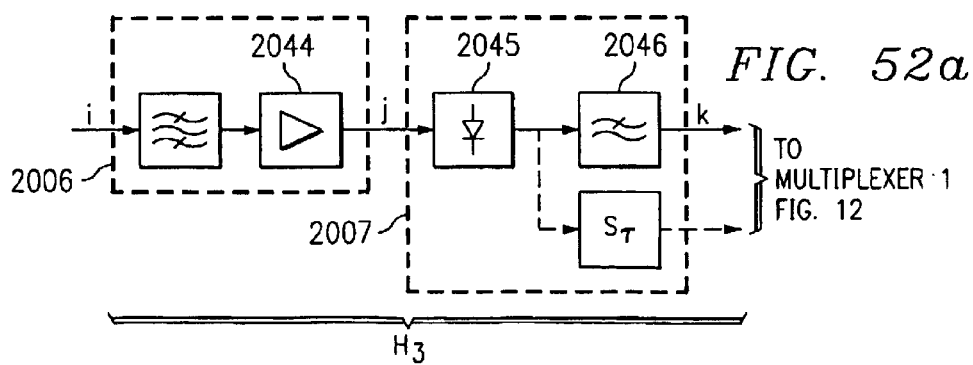
FIG. 52a

SYSTEMS AND METHODS FOR MILLIMETER AND SUB-MILLIMETER WAVE IMAGING

This patent claims the benefit of U.S. Provisional Patent Application Ser. No. 60/150,397, filed Aug. 23, 1999, and incorporated herein by reference.

FIELD OF THE INVENTION

The present invention relates generally to imaging systems and method and more particularly to a system and method for millimeter and sub-millimeter wave imaging.

BACKGROUND OF THE INVENTION

In the field of detection and-or imaging of concealed objects, millimeter and sub millimeter wave (hereinafter referred to as "s-mmw") radiation has very interesting properties when compared to optical, microwave and radio signals. This radiation has superior propagation in poor weather conditions (e.g., rain, fog, smoke, chemical gases, dust, etc.). Moreover, it can penetrate tissue, plastic materials, different textiles, different soils and other opaque media. The wavelength is short enough to provide sufficient resolution in the images and to enable the construction of optic-like detection and imaging systems, yielding compact and lightweight systems.

S-mmw radiation has enormous potential in safety applications: weapons, drugs, contraband and chemical explosion detection in secured areas such as airports, courthouses, banks, schools, and others. Furthermore, the issue of tracking millions of undiscovered mines in former battlefields is challenging. In all of these situations, a failure to detect harmful, concealed objects can have catastrophic consequences.

Conventional inspection techniques for detecting weapons and contraband carried by persons at the entries and exits of secured areas make use of simple systems sensitive to induction changes in the observed area Most of these simple techniques are restricted to a binary (yes/no) detection of the presence of metallic items only, without any details, features or positional information about the object. These systems cannot be used for imperceptible, efficient and real-time contraband detection. The widespread availability of plastic and ceramic weapons, combined with the desire to detect explosives, plastic mines and other contraband make these conventional detection systems less useful. In order to reliably detect and visualize this new class of weapons, mines as well as drugs or explosives, radically new techniques are required.

Millimeter wave imaging of objects scattering, reflecting, or emitting the radiation in this frequency range is one of the promising possibilities. This promise is due, in part, to the fact that millimeter waves penetrate clothes, without exhibiting (known) harmful effects on the human body. The reflection and attenuation characteristics for (sub) millimeter wave radiation of the human body are substantially different from the same characteristics of ceramic and plastic weapons and narcotics. This enables the imaging of objects made of these materials and concealed on a person. Metallic objects also reflect millimeter wave radiation differently than the human body.

Systems have been developed for the real-time visualization of (covered) objects by means of quasi-optical s-mmw imaging systems. Passive as well as active systems have been and are further under development. The basic building blocks, which can be identified in existing systems, are schematically presented in FIGS. 1a, 1b and 1c.

Referring first to the passive system of FIG. 1c, the multi-element detector array 5 receives radiation 8 by means of focusing lens 4. Radiation 8 is emitted by the person carrying covered object 3 and also includes the ambient radiation 9 reflected and scattered by the covered object. For indoor applications, however, the temperature contrast between the body 8 and ambient radiation 9 is quite small such the difference between metal, plastics explosives and human skin will be substantially difficult to differentiate. Hence, there is a need for an efficient low cost active illumination system.

Active systems developed up to now are based on the illumination of the object by means of radiation whose coherence level was lowered in an inefficient way. Referring now to FIG. 1a, radiation source 2a generates quasi-coherent s-mmw radiation that is directed towards a rotating diffuser 2b. Rotating diffuser 2b has a random conductive surface. The rotating diffuser is used to destroy the spatial coherence of the incident radiation beam and to redirect it towards an observed object 3.

In another implementation of an s-mmw illumination device shown in FIG. 1b, it has been proposed to use a spatially distributed array 1 of point sources in place of the combination of point source 2a and rotating diffuser 2b. The point sources of the array are sources of quasi-monochromatic radiation with slightly different central frequencies of the emitted radiation (the frequency distribution does not have to be larger than the normal manufacturing variations to achieve the interrelated results). The array of sources 2a/2b or 1 both are able to produce an illumination of the object 3 by radiation with decreased spatial coherence.

Referring to both FIGS. 1a and 1b, the object image is projected on a multi-element detector array 5 by means of a focusing element 4. An array of electrical signals is generated by the detector array 5 and processed (e.g., mixed, amplified, filtered) by electronic means 6 so that the object image can be visualized by the displaying means 7.

While a prior art active imaging system may in principle lead to good visual quality images, a high performance implementation is not sufficiently practical due to the inefficient nature of the coherence destruction mechanism. The fundamental reason is that the degree of spatial coherence of the illuminating radiation at the plane of the object strongly depends on the ratio between the size of the array of the spatially distributed non-coherent sources and the distance between said array and the object. Due to this dependence, the array size should be sufficiently large when imaging objects are at practical distances. Consequently only for the largest and, hence most expensive arrays, may the best imaging results be obtained.

A second drawback of prior art s-mmw imaging systems is the use of rotating diffusers in order to destroy coherence. The very bulky rotating diffusers need to rotate continuously and sufficiently fast The effectiveness of such reduction of the spatial coherence level is not high. Hence more acceptable and effective approaches for quality imaging of concealed objects are desired.

Another drawback of both these systems is the very limited possibility of using multi-frequency radiation for object illumination. To develop a multi-element array source in which every element will be able to emit radiation within sufficiently broad-band spectral range is practically non-achievable task. The random conductive surfaces of a diffuser cannot reflect the radiation in the same manner within a wide spectral range. Even if a known rotating diffuser could be developed to operate within such a wide spectral range, it would still have all of the problems of currently commercially available rotating diffusers.

Said in another way, prior art active s-mmw imaging systems are limited in effectively implementing multi-frequency illumination of the object. In the case of the multi-element source it is practically unfeasible to construct a multi-element array source, whereby every element would be able to emit radiation within a sufficiently broad spectral range. In the case of a rotating diffuser, the random conductive surface cannot reflect the radiation in the same way for the whole spectral range. Even if some modification of such mechanical diffuser will be developed the problem of rotating such bulky diffuser still holds.

SUMMARY OF THE INVENTION

In prior art active and passive systems, only one image (or eventually two in the case images for different polarization states are taken) is available. This can be stated as "one- or two-parameter" partial millimeter wave imaging. However, an image could be decomposed in much more partial images, whereby each partial image represents an image for a set of combinations of physical parameters of the illuminating radiation. These physical parameters are e.g. the carrier frequency of the illumination, the polarization state and the angle of incidence. Such an extended set of partial images for different combinations of the physical parameters allows much better analysis of the objects and clutter in the obtained images because one has access to each of these components. Having access to the partial components of the images allows to optimize the weighted combinations of the components (e.g. neglecting the bad components). In conventional imaging techniques such decomposition and advanced image analyzing techniques are not available.

Because X-ray is ionizing radiation, infrared radiation is non-penetrative through clothes and microwave radiation exhibits wavelengths which are too large to carry a needed volume of information concerning contraband objects, the proposed s-mmw imaging technique and apparatus are suitable realizations of remotely controlled and real time contraband detection.

The present invention provides a number of novel features that can be used advantageously in imaging systems. For example, in security applications, use of the present invention allows better imaging for concealed objects such as weapons and/or drugs. This system could be useful, for example, in airports where prior art passive systems are not as effective.

In one aspect, the present invention provides an apparatus for imaging. At least one source of composite radiation illuminates a field of view. The radiation includes a set of multiple phase-independent partials that are independently controllable and exhibit distinct physical features. A quasi-optical element is disposed between the field of view and a multi-element receiver. The multi-element receiver is disposed to receive image radiation from the quasi-optical element. Particular ones of the receiver elements transform the image radiation into a set of electrical signals that include information relating to features of the partials.

In one embodiment, an s-mmw imaging system includes a non-rotating diffuser that destroy the spatial coherence of radiation incident on the diffuser and directs the radiation towards a field of view. At least one radiation source is disposed to illuminate the diffuser. In the preferred embodiment, the radiation source(s) generates radiation having a wavelength between about 0.1 mm and about 10 mm. A quasi-optical element is disposed between the field of view and a multi-element receiver. The quasi-optical element directs radiation from the field of view toward an imaging plane. A multi-element receiver is disposed in the imaging plane such that particular ones of the receiver elements transform radiation into a set of electrical signals.

In another aspect, the present invention provides a method of illuminating a field of view. Radiation, preferably with a wavelength greater than about 0.1 mm is generated. The radiation includes multiple phase-independent partial components that exhibit distinguishable physical features. The radiation is encoded to label different ones of the multiple partial components. The radiation is then directed toward a field of view and focused on an imaging plane. The radiation can then be detected from the imaging plane and converted into electrical signals. Information relating to features of the multiple partial components can then be extracted from the electrical signals.

In yet another embodiment, the present invention provides a millimeter wave system that includes a source of radiation The radiation includes a set of independently controllable radiation components. Each radiation component includes a doublet that includes two spectral lines. Each radiation component is also labeled by a given frequency shift between the two spectral lines. The system also includes a receiver with an array of receiver elements disposed to receive the radiation emitted by the source. The receiver transforms the received radiation into an array of electrical signals. A processing system can be used to decode the array of electrical signals based on the labels of the radiation components.

As will be discussed throughout the text, aspects of the present invention provide a number of advantages over prior art systems. For example, by utilizing the techniques of the present invention, clearer images are possible in a variety of contexts. Other aspects of the present invention can be used in other applications such as in communication systems.

BRIEF DESCRIPTION OF THE DRAWINGS

The above features of the present invention will be more clearly understood from consideration of the following descriptions in connection with accompanying drawings in which:

FIGS. 4a–4d show the results of the numerical calculations of quasi-optical imaging of some real-life object illuminated by smmw radiation with various spectral compositions;

FIGS. 5a–5e illustrate step by step the possible effective changes of the spectral density distribution of the statistically averaged radiation recorded by the receiver array;

FIG. 21 is liquid crystal diffuser able to destroy spatial coherence of radiation;

FIG. 22 is a prior art surface roughened diffuser;

FIGS. 23a–23b are cross-sectional views of a preferred multi-layer diffuser featuring gradual surface roughness;

FIGS. 40a–4g are representations of s-mmw multi-spectral radiation comprising a plurality of doublets and multiplets;

FIGS. 50a–50e are diagrams schematically showing the building units of signal amplifying and transformation SAT-blocks according to the present invention;

FIGS. 51a–51b are block diagrams schematically showing processing units for beat spectrum analysis of doublets and multiplets according to the present invention;

FIGS. 52a–52c are block diagrams schematically showing LF-processing units;

DETAILED DESCRIPTION OF THE EMBODIMENTS

The making and use of the presently preferred embodiments are discussed below in detail. However, it should be appreciated that the present invention provides many applicable inventive concepts that can be embodied in a wide variety of specific contexts. The specific embodiments discussed are merely illustrative of specific ways to make and use the invention, and do not limit the scope of the invention.

The present invention, which includes numerous aspects and variations, will be described in the following text. An exemplary system will first be described briefly to put into context one particular implementation of the concepts of the present invention. Each of the components as well as other novel features will then be described.

I. The System

Figure 2:
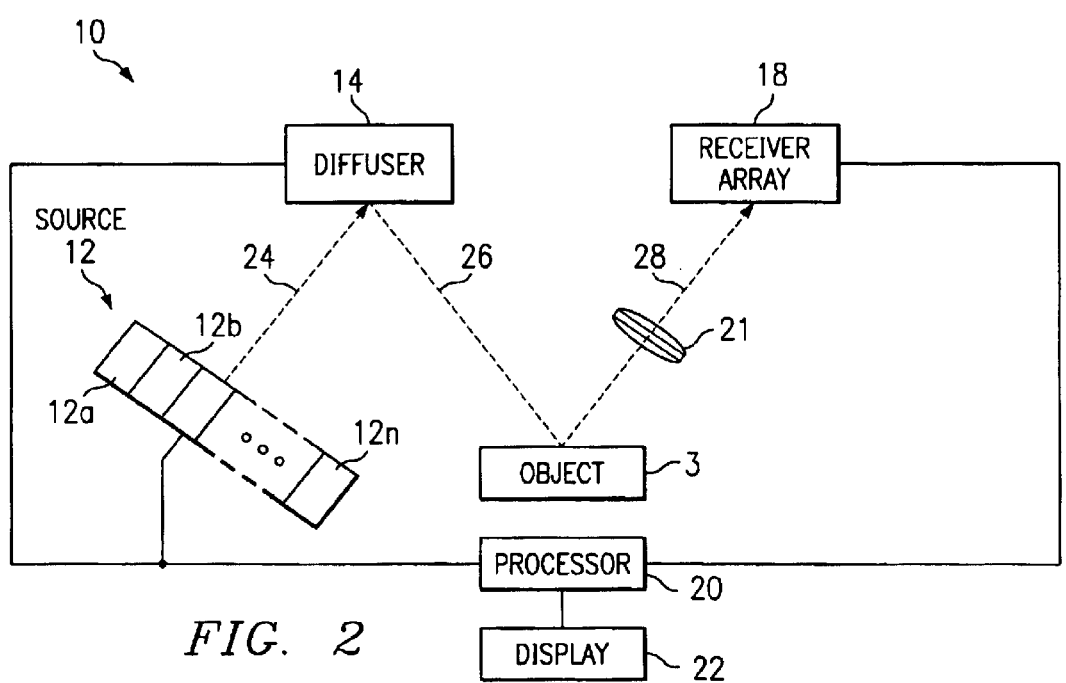
FIG. 2 shows schematically the basic building blocks of a quasi-optical s-mmw imaging system of the present invention.

FIG. 2 illustrates a simplified illustration of a first embodiment system 10 of the present invention. This system 10 includes a millimeter wave (mmw) and/or sub-millimeter wave (s-mmw) source 12 that is preferably a point-like source. The latter means that the source emits spatially coherent radiation. In the preferred embodiment, the spectral components of the radiation from source 12 may be anywhere in the millimeter and/or sub-millimeter wave range of the electromagnetic spectrum. For the purpose of this invention, the term s-mmw will be used to refer to any radiation in the millimeter or sub-millimeter wave range, for example having spectral components between about 30 GHz and about 3000 GHz (or wavelengths from about 0.1 mm to about 10 mm).

In a simple embodiment of the invention, the source 12 emits narrow band (e.g., quasi-monochromatic) radiation. Such radiation can be generated by any standard monolithic or waveguide s-mmw radiation source manufactured for operating at fixed frequency. The radiation from this source may be spatially coherent.

In a more preferred embodiment, source 12 is a wide-band radiation source. In one embodiment, the source 12 may comprise one or more sub-sources, each emitting radiation comprising different spectral parts. Preferably, the amplitudes of the components of these spectral parts, as well as their spectral position and content, are individually controllable by their respective sub-source drivers. The radiation outputs of the different sub-sources may be constructively united in such a way that all spectral components will be emitted from the same spatial point (or at least from the same horn for the case of a waveguide realization of the sources) or from spatially near points. In another embodiment, source 12 may comprise one or more sub-sources, whereby each sub-source is characterized by a particular polarization state, not necessary different for each sub-source.

Generally, drivers of the partial sources are able to control both the averaged power of the source 12 emitted radiation and the width and central frequency of spectral localization of correspondent spectral component In another preferred embodiment, these drivers also implement a code to each sub-source separately, such the radiation emitted by each sub-source (characterized by its spectral content and-or polarization state) and after its interaction with the object can be individually accessed by decoding the composite radiation at the receiver side. In accordance with another aspect of the invention the spectral composition of the wide-band radiation comprises only narrow-band spectral components, the power and central frequency of which may be independently changeable.

As will be described below, the multi-frequency approach provides a number of advantages. For example, films have been designed to exhibit the same scattering characteristics as human skin. With multi-frequency illumination, it is extremely difficult to make objects invisible by hiding them with these films over a wide spectral band. When one takes into account that the scattering properties of human skin also depend on the ambient moisture and temperature conditions, as well as on the nervous state of the individual carrying the covered object (being excited or not and so on), it would be near impossible to cheat a wide spectral band imaging system. Other advantages of the multi-frequency source 12 will be discussed in more detail below.

Returning to FIG. 2, source 12 emits s-mmw radiation to diffuser 14, which diffusively reflects the radiation toward object 3. The diffuser 14 also essentially decreases the spatial coherence of the radiation in the field of view. This feature improves the imaging properties of the system 10 due to the reduction of spatial coherent related noises such as speckle and glint or glare. This result is valid for quasi-monochromatic radiation as well as for multi-frequency radiation. In the latter case, the system is more effective in reduction of the coherence level because both spatial and temporal coherence of illuminated radiation are simultaneously reduced.

Figure 1A:
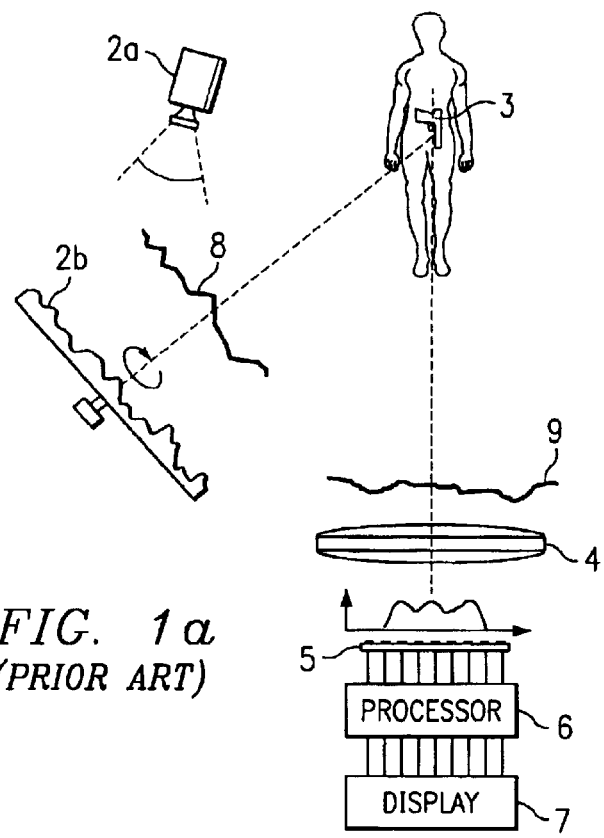
FIGS. 1a–1c show the basic building blocks of a prior art quasi-optical 2D s-mmw imaging system.
Figure 1B:
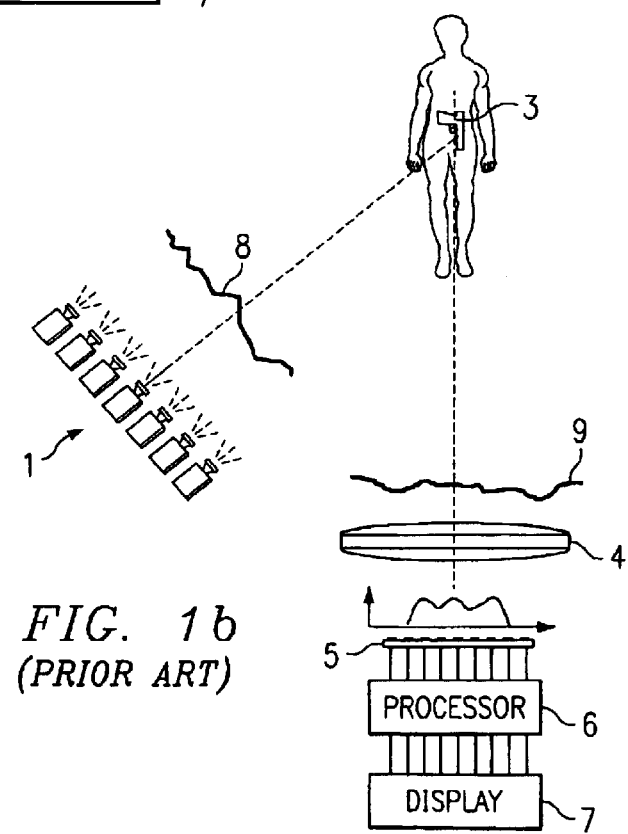
Figure 1C:
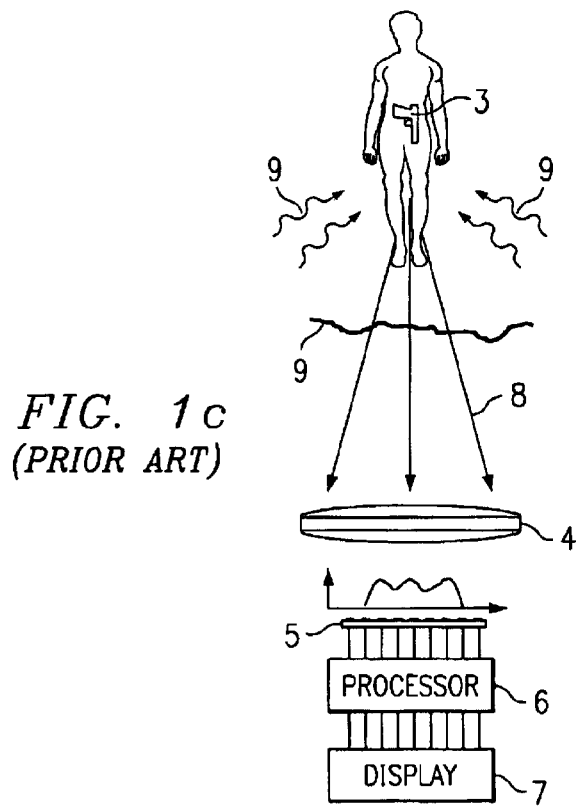

In the preferred embodiment, diffuser 14 comprises a non-movable array of electronically or optically controllable scattering elements. The electronic or optical control allows the physical features of the scattered radiation, such as the degree of spatial coherence, to be changed. This embodiment is preferred because a system that requires a large movable unit is dramatically limited in the number of applications in which it can be used. That being said, alternate embodiments of the imaging system of the present invention can be implemented with a rotating diffuser 14 (see e.g., element 2b in FIG. 1a). The unique diffuser 14 of the preferred embodiment will be described in more detail below.

In the preferred embodiment for the diffuser 14, the scattering elements can be dynamically clustered such that each cluster represents an another average angle of incidence on the object. Each cluster receives its code, such that radiation scattered by each cluster and after its interaction with the object, can be individually accessed by decoding the composite radiation at the receiver side.

As a note, the term "source" can be used with different meanings in different contexts. For example, the term "source" can be interpreted together with the state of the emitted radiation. When referring to source of a coherent radiation, one refers to a bare source of radiation as indicated by box 12 in FIG. 2. When referring to a source of spatially non-coherent radiation one can refer to the combination of that same box 12 and the spatially coherence destroying diffuser 14. Alternatively, one can be referring to a source emitting spatially non-coherent radiation (e.g., a source in combination with noise generators or a source driven in chaotic mode, as will be described below). Therefore, it should be understood that a source can refer to the source itself or a combination of elements including the source.

Diffuser 14 directs the radiation toward object 16. The object under test 16 is situated in the field of view of a lens 21, which projects an image on the receiver array 18. The characteristics of the radiation reflected, scattered and absorbed by the object 16 depends on the different materials, surface, texture and volume of the object 16. If object 16 is not uniform, than radiation 28 may be scattered by different parts of the object 16 in a different way. For example, if object 16 includes a plane metal portion, reflected radiation 28 will therefore include both specular and diffuse components. The imaging system of the preferred embodiment includes techniques to differentiate and even locate these different components, as will be discussed below.

The receiver array 18 preferably comprises antenna-coupled nonlinear elements. The frequency response of these antennas matches the spectrum of the s-mmw radiation. In the preferred embodiment, receiver 18 comprises an array of Schottky barrier diodes used as detectors or mixers. The lens 21 is positioned such that the object 16 is inside the field of view and the image of the object is projected on the receiver array 18. Although not illustrated in FIG. 2, a polarizer may be included between lens 21 and detector 18.

The image information detected by receiver 18 is provided to processor 20, which processes the information to create a viewable image or a set of viewable images. The viewable image(s) is (are) provided to display 22, which may be a CRT monitor or an LCD display, as two examples. The images can be stored in computer memory to allow advanced signal processing on the acquired images.

In some embodiments, processor 20 is also coupled to source 12 and/or to diffuser 14. This connection can be made through a common line (or lines) or via separate connections. This feedback can be used to control the operation of source 12 and/or diffuser. 14 in combination with the principle of encoding spectral and/or polarization information at source 12 and/or angular and/or polarization information at diffuser 14. For example, as will be explained below, the diffuser 14 might be affected in order to minimize glint affects As will also be explained, the source 12 might be adjusted to counter ringing effects.

As will become clear from the discussion below, the system of the present invention can provide advantages. In contrast to some prior art imaging systems, the preferred embodiments of this invention provide effective solutions to counter the following physical effects, which substantially deteriorate the image quality. For example, speckle can cause image deterioration effect due to surface roughness of the objects in the field of view. Glint or glare can cause image deterioration due to mirror-like reflections of the objects causing over-saturation inside the receiver or a portion of it. Dispersion can cause image deterioration due to partial absorption of the illuminating radiation by the covering material such that the information of the object is partially lost. Ringing can cause image deterioration due to limited spatial resolution of the quasi-optical imaging system and the relatively large wavelength of the illuminating radiation.

Provisional Patent Application No. 60/150,397, the filing date of which this invention claims benefit, provides some fundamental principles of (non-)coherent imaging theory. For the purpose of brevity, this explanation will not be repeated here. To see this discussion, reference can be made to the provisional application, which is incorporated herein by reference.

II. Multi-frequency Source

In the preferred embodiment, source 12 of FIG. 2 is a multi-frequency source. A multi-frequency source is a source that emits radiation at at least two different frequencies. In typical embodiments, source 12 emits radiation at between about 5 and about 15 different frequencies ranges (or wavelengths). As examples, these different frequencies may be generated by multiple distinct sources or a single source that scans over the desired frequency range.

As an example, it is possible to eliminate, or at least minimize, speckle in the global image of the object 16 with the creation of statistically independent partial images. These partial images can be created using radiation containing at least two substantially different spectral regions. For example, the wave fronts of the radiation of two closely spaced narrow spectral regions can be transformed by the object 3 and projected by the lens 21 on the receiver array 18 in very similar way, resulting in similar speckled images.

Figure 3A:
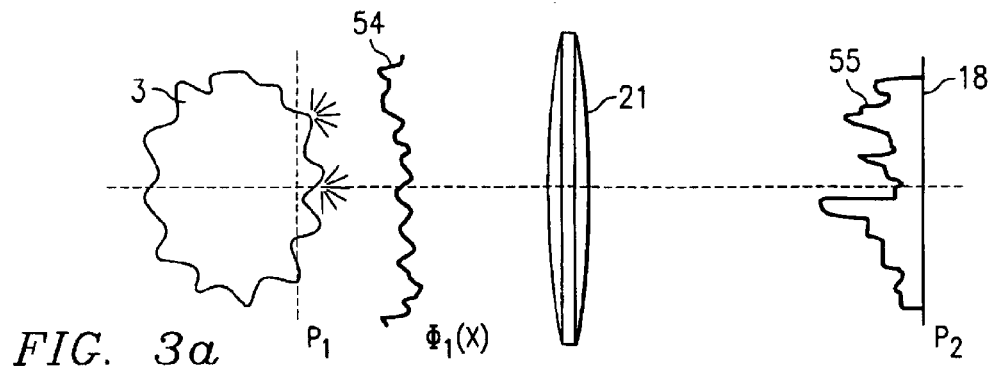
FIGS. 3a–3d illustrate the evolution of the wavefronts incident and reflected on the objects and projected on the receiver plane by means of the lens.
Figure 3B:
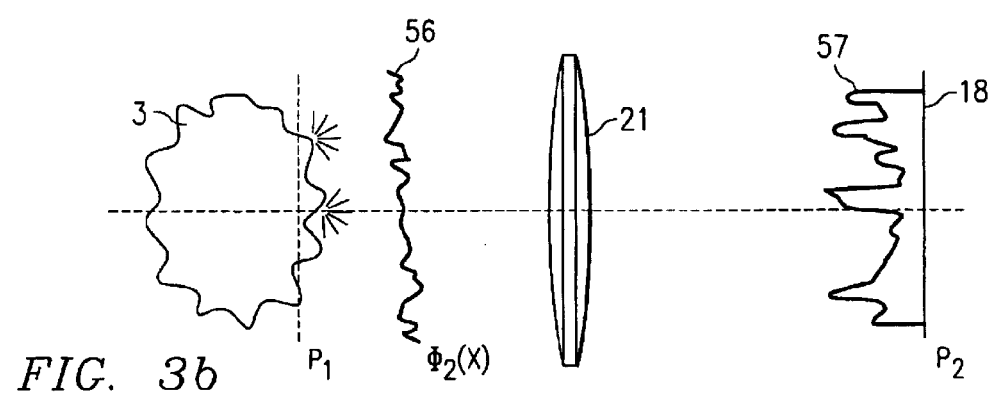
Figure 3C:
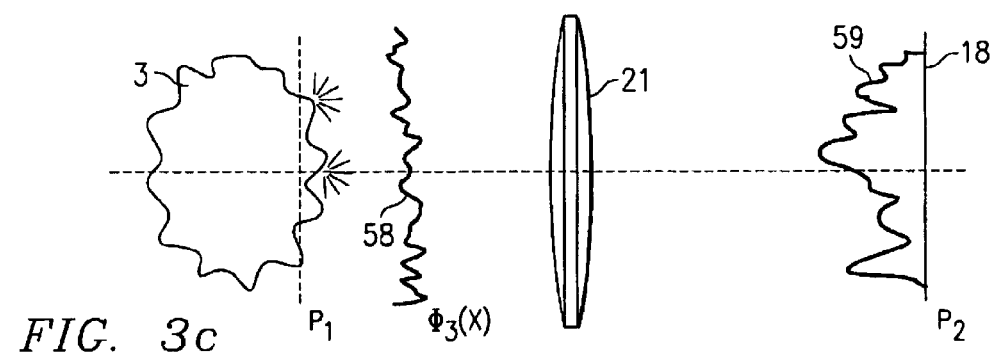
Figure 3D:
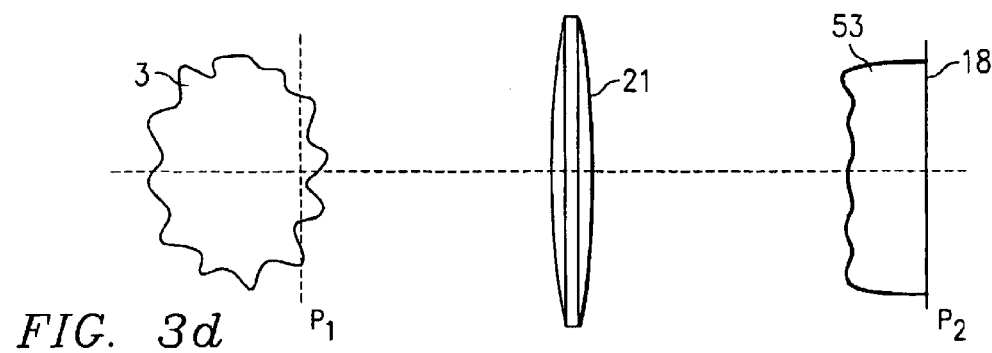

Considerably increasing the frequency difference between the two components of the illuminating radiation will result in distinguishable speckled partial images. These partial images can be presented as shown in FIGS. 3a–3c. The distorted waveforms obtained after the interactions with a rough object are presented by curves 54, 56 and 58. The curves 55, 57 and 59 refer to partial images obtained at very distinct frequencies. The combination of the different partial images by accumulating their energy during the exposure time in the nonlinear receivers leads to an enhanced sum image 53 in FIG. 3d.

The addition of any number of other spectral lines (even up to a continuous spectrum), each located in a relatively small spectral range, will only yield an increased average intensity of the primary speckle image, whereby the same speckle structure is conserved. The exposure time is essentially shorter than in the case of quasi-monochromatic spatially non-coherent radiation. The required frequency differences depend on the geometrical characteristics of the object and decrease when the aforesaid wave front phase distortions increase. In practical cases, the frequency difference between the different sources is of the order of about 5 to about 10 GHz or more.

Widening the effective bandwidth of the illuminating radiation results in an increased number of spectrally different and, consequently, statistically independent speckle partial images. In other words, referring to coherent imaging theory, one decreases temporal coherence of the radiation. It is to be understood that besides the analog or optic-like integration of the partial image signals, a (weighted) digital summing of the partial statistically independent images is achievable as well. In fact, such a digital summary is even preferred in some instances. Digital summing is important when effects intervene. The next paragraphs will demonstrate how the multi-frequency approach can keep a high image quality even when dispersion and ringing are present.

Multi-frequency s-mmw illumination of an object is suitable for minimizing the ringing effect In FIGS. 4a–4d the dependence of the resulting quasi-optical coherent images 200, 205 and 210 of an idealized smooth object on the spectral composition of the multi-frequency source is illustrated. The different curves show iso-intensity contour plots at different monochromatic frequencies. The real dimensions of the object are shown on the x and y axes.

The images are calculated for the case of a smooth object (in comparison with the wavelength range of the multi-spectral radiation) without dispersive characteristics (permittivity values of the materials are assumed to be frequency independent), but with large details at various depths. The quasi-optical elements and the detectors are also assumed to be zero dispersion elements. The object is illuminated with the same s-mmw power for all frequencies of interest.

In the case of a bad spectral composition we see that the image (intensity distribution) 200, 205, 210 of the object results in a garbled image. Single frequency coherent imaging does not provide a sufficient spatial resolution and true distribution simultaneously. The spatial resolution is determined by the spatial bandwidth of the quasi-optical system and the wavelength of the illuminating radiation.

For some combinations of the temporal frequency f and feature size of the object there are no oscillations in the image. But when the frequency for the feature sizes change the image quality worsens. The limited resolution of the s-mmw radiation produces oscillations. Such phenomenon is equivalent to under-sampling. If the object has a complicated structure with different sizes of details, then the single frequency imaging cannot provide adequate object recognition.

Simulations show that the multi-frequency imaging can yield higher resolution 215 (FIG. 4d) than mono-frequency imaging (FIGS. 4a–4c). But simply increasing the number of frequencies does not automatically provide better image quality. In the preferred embodiment, the source provides a sufficiently broad frequency range with substantial frequency difference. Quantitative values can be easily estimated in the following way. The ringing effect appears as soon as the spatial frequency components of the object exceed the cut-off spatial frequency of the coherent imaging system:

$$|\bar{n}_{max}^{coh}| = \frac{L}{2\lambda d_2} \quad (1)$$

where $\lambda$ is the wavelength, $d_2$ is the distance between the lens and the imaging plane, and L is the size of the lens. Taking into account this cutoff spatial frequency, one can derive that oscillations in the image originating from different frequencies cancel each other under the following conditions:

$$\lambda_n - \lambda_m = \lambda_n \lambda_m / N \quad (2)$$

where $$N = \frac{2\lambda d_2}{LZ} \quad (3)$$

and Z is the size of the object.

For typical values of these parameters, the typical step $\Delta\lambda_n = \lambda_n/N$ where N=5–15. The changes in wavelength, and therefore frequency, are preferably in the range of about 17% to about 20% of the wavelength of two neighboring wavelengths. Further decreasing the step will result in summing virtually identical intensity distributions with increasing the absolute value of the signal but insufficient elimination of the distortion oscillations.

In reality, every single element of the system including the object and any covering layers are characterized by dispersion and inhomogeneities. The complex permittivity value is dependent on the frequency. The conditions of scattering, reflection, and absorption of every object in the quasi-optical imaging system are as a rule different for each frequency. In particular the materials, which would be used to cover objects, can exhibit strong dispersion behavior in the absorption process. Some contraband materials can exhibit strong dispersion behavior in the absorption process. Some contraband materials can exhibit strong absorption resonance at particular frequencies. Also the detectors contribute to the global dispersion over the large frequency interval.

To cope with this dispersion behavior it is essential to be able to control the intensity level of the different s-mmw sources as well as their spectral content, emitting in different spectral regions. Equalizing the spectral response at the detector plane can be effectuated by introducing a feedback system. The presence of the feedback loop is essential to set the intensity level of each s-mmw source in accordance with a predefined algorithm or rule.

Figure 5B:
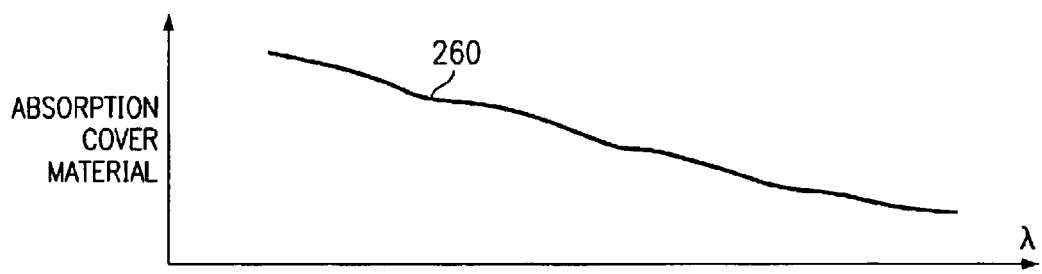
Figure 5C:
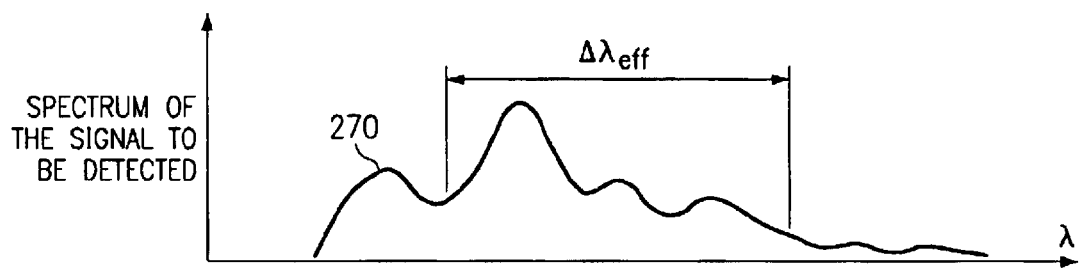

In FIG. 5a a hypothetical wavelength dependent reflection curve 250 of an object formed from different materials is depicted. In FIG. 5b the spectral dependence of the absorption coefficient 260 of a hypothetical cover material is simulated. The resulting signal 270, which has to be detected by the array of antenna coupled nonlinear detectors, is shown in FIG. 5c. This signal 270 is the result of a weighted averaging process over all the pixels of the whole detector array.

Figure 5D:
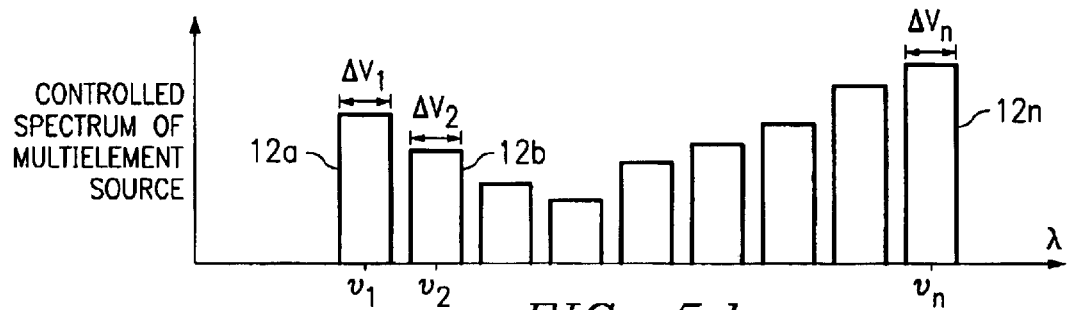

The averaging process itself can be implemented in several ways. To avoid deteriorating dispersion effects, it is preferable to detect a signal having a more equalized frequency distribution. Therefore it is preferable that every single s-mmw $12a$, $12b$, $12n$ can be individually tuned as illustrated in FIG. 5d.

Figure 5E:
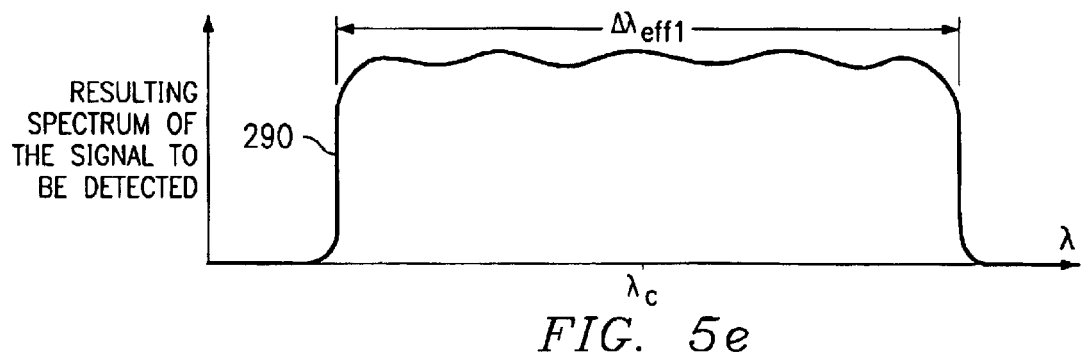

Finally the multi-frequency spectrum of the tuned signal 290 received by the detectors is shown in FIG. 5e. Each frequency interval is detected with about the same average intensity. By means of amplitude-tuned generators, the dispersion effect of the different components of the imaging system is minimized and the advantages of the multi-frequency approach can again be completely exploited.

A multi-frequency spectrum consisting of frequency intervals is preferential with respect to a pure discrete one as particular absorption resonances can occur. The tuning of the amplitude of a s-mmw source emitting a discrete line at the absorption resonance frequency has no sense. Hence spectral information would be lost resulting in a degraded image quality. Particular wavelengths, however, missing in some parts of the image can reveal the presence of particular materials, e.g., concealed drugs or weapons. The real time detection of pronounced relative increases or decreases of average intensity over some of said spectral different partial images further enhance the power of the multi-frequency approach and form the basis for spectroscopic non-coherent imaging techniques. The benefits of the embodiment of spectroscopic techniques are here summarized.

Figure 14A:
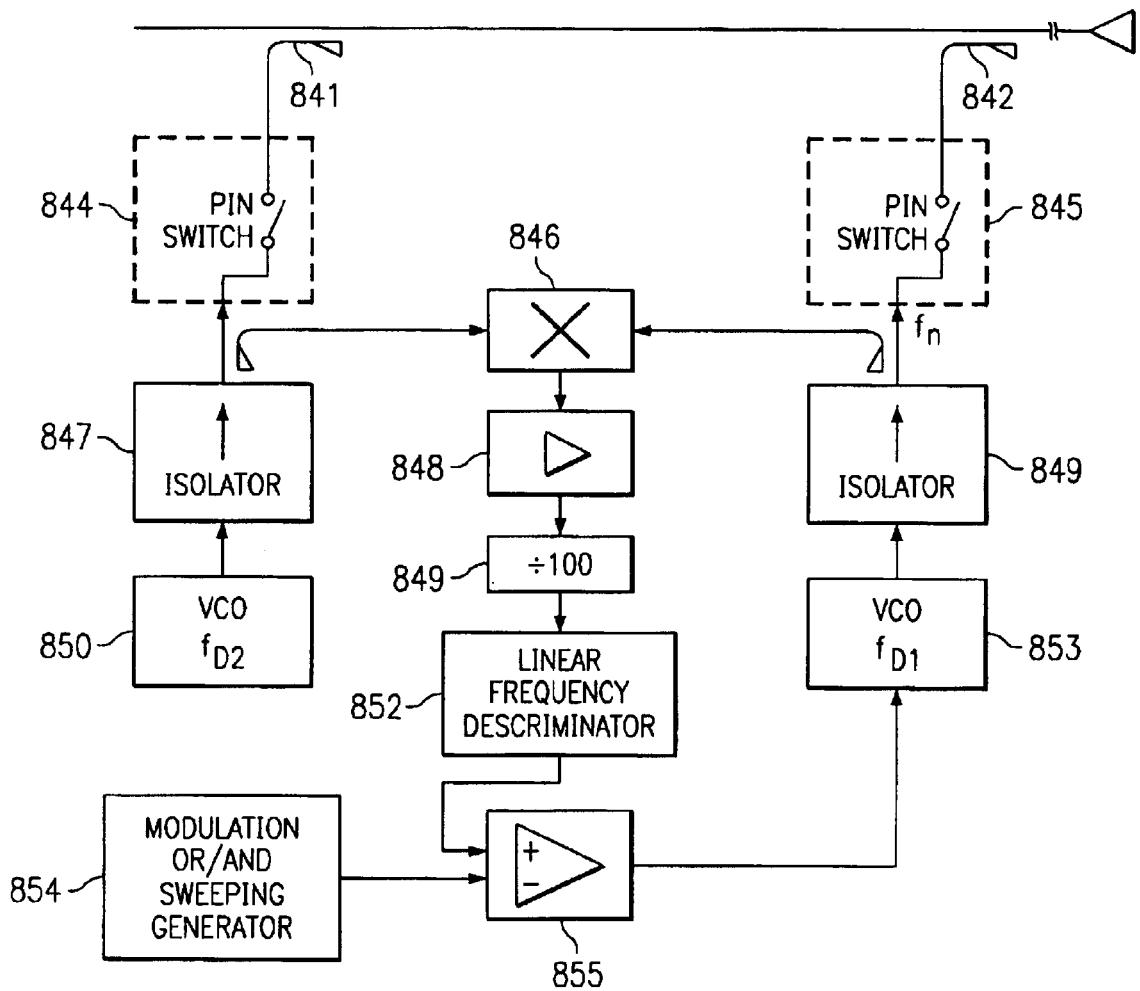
FIGS. 14a–14b show schemes for controlling the frequency shift between doublet components.
Figure 14B:
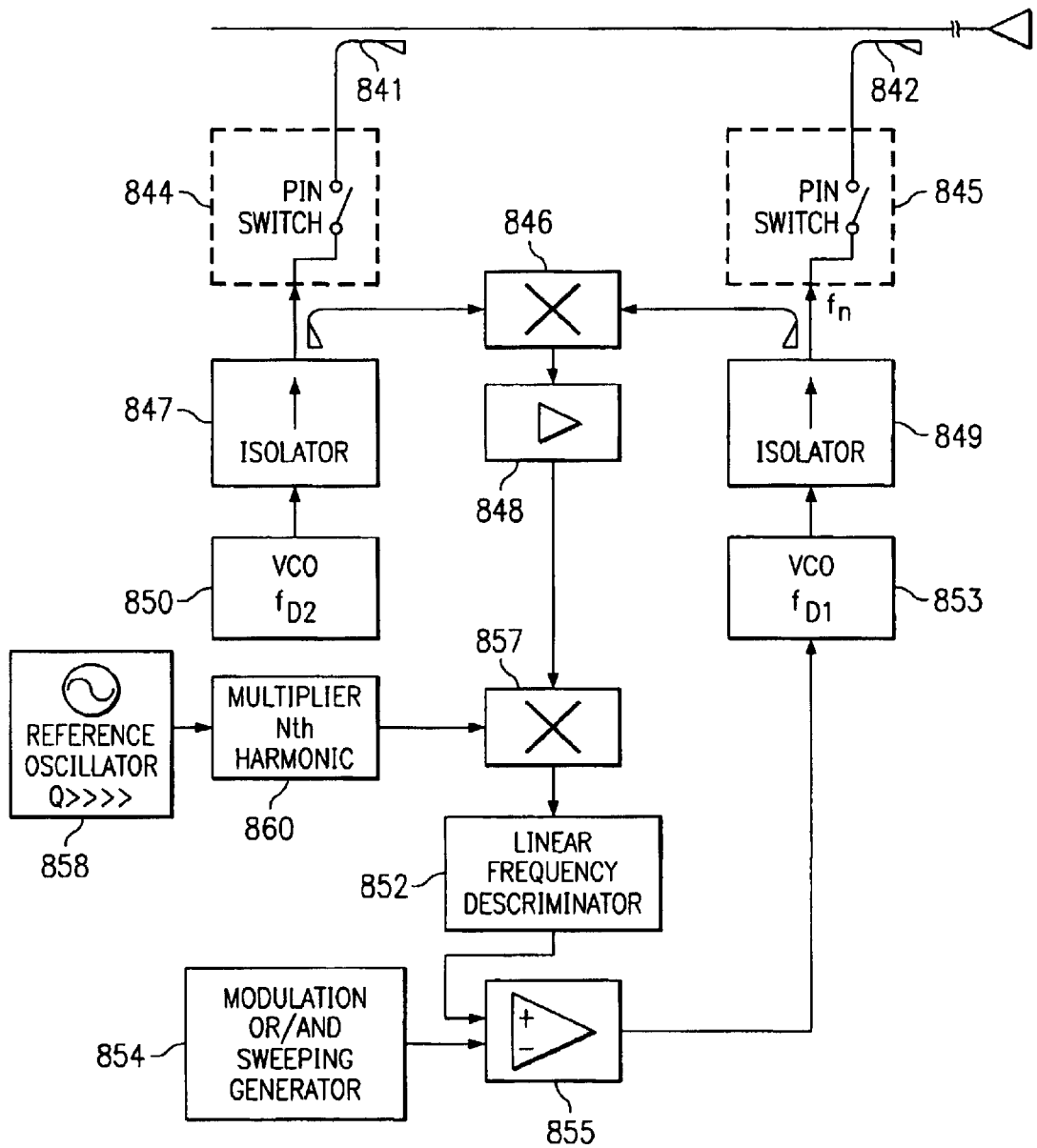

In general gas molecules (originating from drugs or explosives) may exhibit very fine and precisely defined rotational absorption lines in the s-mmw spectrum. When sufficient molecules are available these spectral lines can be traced by adding a stabilized subsource $12m$ of s-mmw radiation emitting the particular absorption line. When the subsource $12m$, however, is sweeping in a precisely controlled way, spectroscopic measurements allow remotely obtaining the fine chemical structure of hidden substances in combination with high quality images of this substance obtained by combining distinct partial images recorded at different frequencies which can be strictly defined in accuracy and arranged in a broad spectral range (50–220 GHz and even more). So this is a tool to combine precise spectroscopy with imaging possibilities. The principle of spectroscopic and non-spectroscopic imaging will be the same. The big difference between multi-frequency imaging in a more general sense and the spectroscopic approach lies in the absolute frequency stability of the s-mmw sources. More details about the implementation of stabilized s-mmw sources will follow. A preferred implementation of stabilized s-mmw source is the doublet, a particular kind of two-frequency radiation. The doublet is defined as a pair of two closely spaced frequencies whereby the value of their frequency difference is essentially smaller than the value of their central frequency. A generalized scheme for controlling the frequency shift and the phase between doublet components is presented in FIG. 14 and will be further detailed below. The doublet radiation can be detected with very narrow band detector, leading to extremely high dynamic range and sensitivity. This means that the level of illuminating radiation can be extremely low, such that not a single danger exists for persons illuminated by this s-mmw radiation.

If the gas molecules are only available in a restricted quantity on the person in the field of view, then there exist a more preferred spectroscopic s-mmw imaging solution. In that case it is better that gas molecules are transported towards a special gas chamber with decreased gas pressure. It is a preferred embodiment to collect these gas molecules in a specially designed gas chamber by means of a hoover machine (e.g., a vacuum) and to perform inside the gas chamber transmission measurements in the s-mmw for the identification of the substances. Typical drug molecules can also be available in the expired air of a human being and be transported to the chamber. This principle may be extended to the methods of checking people's clothes for residual drugs or explosive molecules. Clothes of the person under investigation can be temporally stored in a container, provided by a hooving mechanism to collect a substantial amount of gas molecules. In this case the s-mmw technology can be further simplified by drastically decreasing the number of receiving elements down to a single receiver identification channel, operating in a particular narrow band.

The use of radiation with quasi-continuous and wide-band temporal spectrum or a fast and widely scanned one is preferable. In addition, specific spectral lines may be included in the radiation spectrum when such lines are deemed to exhibit the proper disperse effects for a number of special and dangerous contraband materials (special kinds of drugs or plastics weapons, for example). Concurrently receiving and processing/displaying the different frequency statistically independent partial images is quite desirable for real time contraband detection when contraband carrier movements are inherent (possible/acceptable) in the field of view of imaging system.

Adaptive temporally non-coherent s-mmw imaging is preferable when portability and compactness are needed. In this case, a spatially expanded illumination system is not required and in principle, only one point-like frequency-sweeping source may be successfully used such that enhanced imaging and recognition characteristics for a contraband detection system will be provided.

The principle of adaptive s-mmw illumination yields images of high visual quality due to the fact that an increased number of independent partial images are available and their combinations can be controlled using digital processing methods.

Moreover, joint use of adaptive, temporally and spatially non-coherent illumination provides multiple image-enhancing techniques not available in prior art methods and devices. (Mere exist many non-destructive control applications for said imaging technique.)

A multi-frequency imaging approach provides a number of advantages. First of all, it can be used in imaging systems designed to detect contraband by helping to counteract special films that are designed to conceal contraband beneath clothing. These films typically have physical properties that are equivalent to the physical properties of human skin. It is very difficult, however, to develop materials that have the same scattering properties, much less properties equivalent to the scattering properties of human skin, over all frequencies of s-mmw radiation. As a result, even if the radiation at certain frequencies is scattered (and/or absorbed) by certain materials that resemble human skin, the object will still be detectable due to radiation at other wavelengths.

So to conceal a individual carried contraband beneath any specially designed materials is extremely complicated when s-mmw multi-frequency illumination is used. This is an advantage of the proposed active imaging system in comparison with any passive imaging systems. The passive imaging system is sensitive only to temperature (brightness) contrast over the observable surface. As a result, films heated under automatic control are able to mask objects if only passive imaging system is used to detect the object. In this case any differences in reflecting properties of an individual skin and masking films may be simply neglected by properly choosing the temperature of the fills.

The next sections will describe some of the different embodiments that can be used to implement a multi-frequency source, such as source 12 in FIG. 2. Different kinds of multi-frequency imaging systems can be designed and developed depending on a number of factors including the availability and price of the technology the desired level of sophistication, and the required level of control of spatial and temporal coherence.

One way to implement a multi-frequency source is with sub-sources having fixed narrow spectral lines. The spectral lines can be single lines or doublet lines and, depending on the implementation, these lines can be coded or uncoded. When the different sub-sources are coded, one can easily identify their radiation at the receiver side. The spectral bandwidth of the sub-sources can be further increased by adding noise or chaos to the different generators.

In another aspect, a multi-frequency source can be implemented with a sweeping source. In this embodiment, the different frequencies are utilized at different times. In one embodiment, the source will sweep, e.g., linearly, over the entire spectral range. In another embodiment, the source may step through discrete frequencies over the spectral range.

Figure 6A:
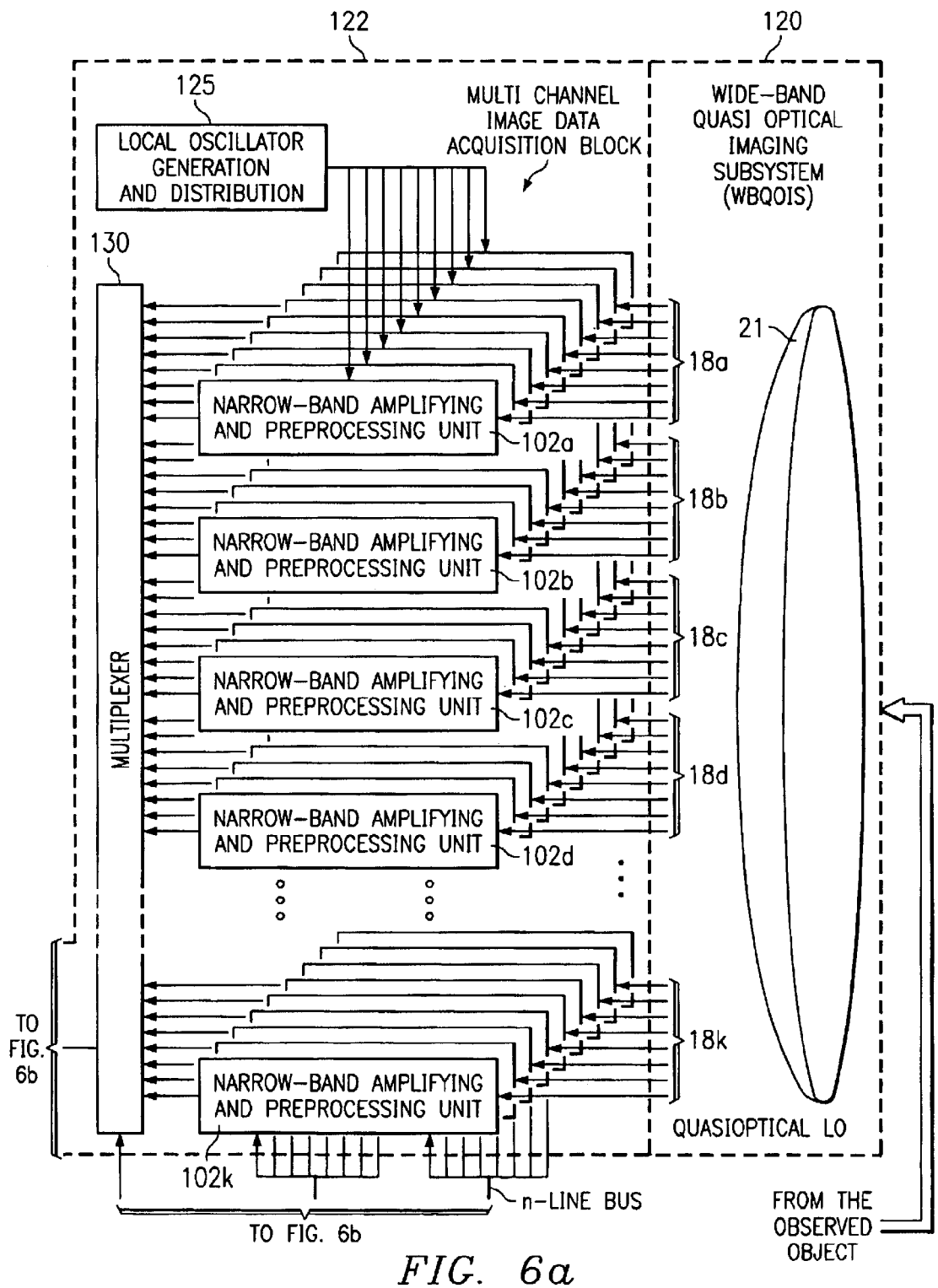
FIG. 6 schematically shows the configuration of the quasi-optical 2D s-mmw multi-imaging system of a multi-frequency embodiment.
Figure 6B:
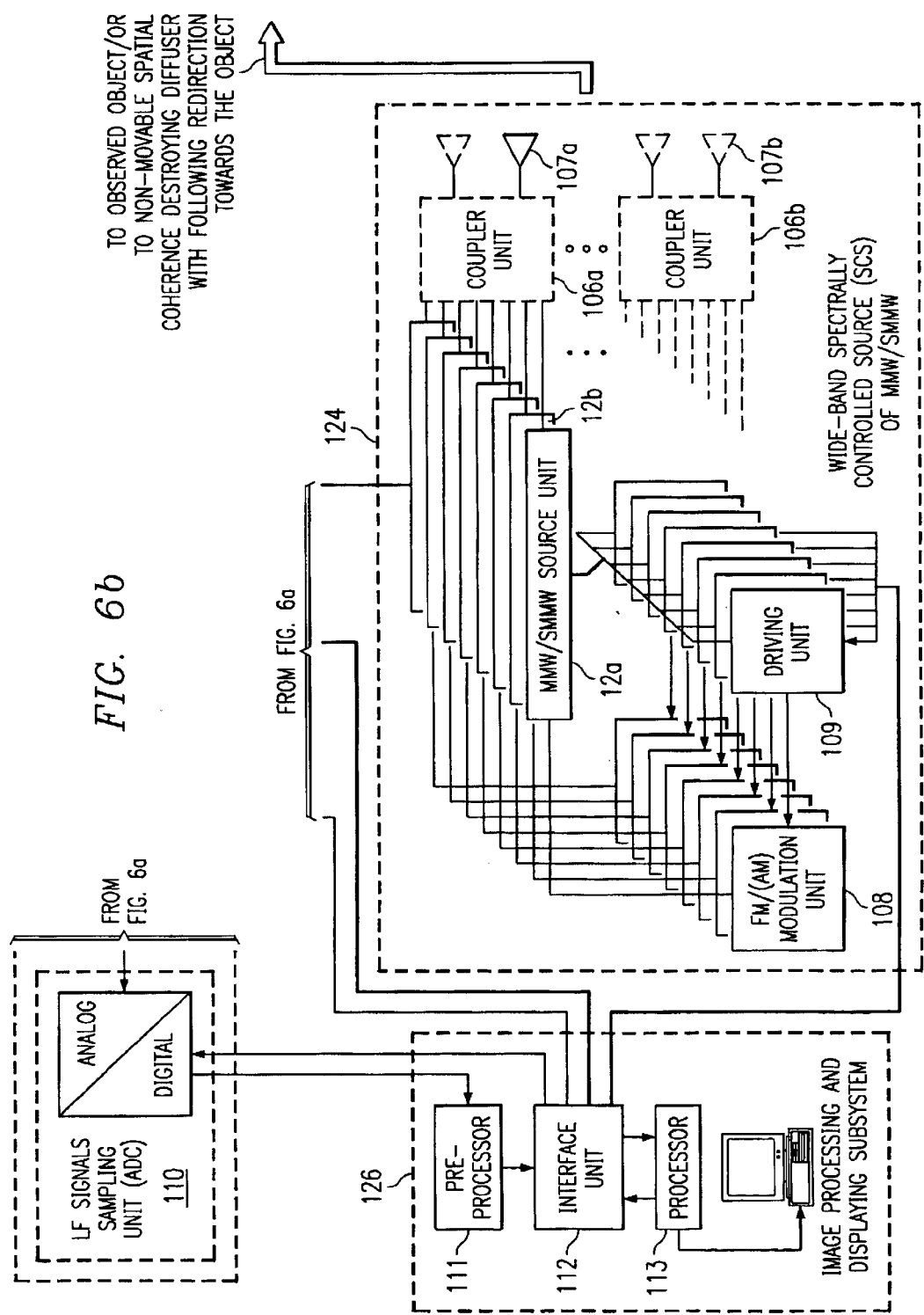

A general block-diagram of an adaptive s-mmw wide-band multi-frequency waveguide based source with controllable intensity level and spectral content of emitted radiation and corresponding quasi-optical imaging system is shown in FIG. 6. The wide-band spectrally-controlled source of mmw/s-mmw radiation includes a set of at least two partial s-mmw sources 12a, 12b with essentially different spectral composition of emitted radiation. A set of sources with large distinctive frequencies is preferred. Difference in their spatial location, however, is not a necessary condition.

It is more preferable to construct a source whose different frequency components are emitted from substantially the same point. In a waveguide realization, the same horn 107 can be used for emitting all frequency components. But in that case each independent frequency channel should be isolated from the others to ensure uncoupled sources.

To accomplish this goal, a set of waveguide couplers 106 is used. Of course, the bandwidth of the radiation spectrum emitted by a particular horn 107 will be limited by the bandwidths of one and correspondent waveguide. If more wide-band radiation is needed for the illumination goals, the s-mmw source should include some limited number of point-emitted horns being frequently distinct with particular sets of partial sources for every horn. Additional couplers 106 and horns 107 are shown in phantom in FIG. 6.

In the case of monolithic realization of the partial sources, the set of the coupler units 106 is not needed at all. Every partial source includes an individual emitting antenna (107) that is integrally connected with the source 12.

In the preferred embodiment, a set of driving units 109 provide supply currents for each of the sources 12a, 12b, ... and set of FM/(AM) modulators 108 are intended for distinct modulation of the radiation emitted by the different partial sources.

FIG. 6 provides a very general block-diagram of the source and is only intended to show functional arrangement. Each of the partial sources may be under independent control since each driving unit 109 and corresponding modulation unit 108 has an individual electrical connection with interface unit 112 and correspondingly with processor 113. Including a feedback mechanism allows determining the optimal spectral distribution of the "multi-frequency" s-mmw source for a particular object and environment.

Four principal subsystems can be identified in the feedback loop of the self-adaptive imaging system: a) Wide-band Quasi-Optical Imaging Sub-system (WBQOIS) 120, including a wide-band objective lens 21 and wide-band multi-element receiving array 18; b) Multi-channel Image Data Acquisition Block 122, ensuring adequate pick up of the rectified/or mixed signals from the array elements and amplifying, preprocessing and sampling them; and c) Image Processing/Visualizing Sub-system 126, executing the functions of numerical processing of the partial images signals (e.g., for different spectral sub-ranges), and d) Source Control System Block 124 controlling the levels of radiation of every partial source 12a, 12b, . . . on the base of use of obtained information from the partial images according to chosen criteria.

In the event of another application of the source, correspondent feedback network will contain subsystems corresponding to new functionality of such source with optimum arrangement for these features.

Checking the average intensity level for every partial image by means of the feedback allows setting the optimal spectral distribution in all spectral ranges of the source in real time. The proposed approach is able to take into account any frequency dependence of propagation, penetration, reflection, absorption and rectification (mixing) in order to achieve enhanced quality images.

The multi-frequency approach can be successfully implemented when 1) the used detector array is sensitive in all spectral sub-ranges of the s-mmw radiation of the specified source and when 2) the Quasi-optics, used for forming images in the plane of the detector array, exhibit broadband operation as well.

In the majority of cases, averaging the intensity signals over a whole set of pixels for a particular partial image is necessary for the partial image intensity signals (being generated by elements of detector array) to be used for true estimation of the radiation level of such image. This is due to the possible speckle structure present in any partial image when the intensity value in one pixel of the partial image (or some number of ones) can not be presented. Generally, first partial images should be received by WBQOIS 120, and distinctly preprocessed and sampled by the Acquisition Block 122, processed by the Image Processing unit 126 and only then the information may be used for the source calibration. Such calibration of the source should be repeated in accordance with the changing reflection and absorption conditions of an observed object.

The intensity calibration of the different sources can be done in more than one way. In a first alternative, distinct frequency sub-ranges (emitted by particular partial sources) are individually tuned sequentially in time, preferably by the source block scheme 124 of FIG. 6. For this, it is necessary to switch off all sources but one by means of, for example, PIN switches or MEMS switches (not shown) or driven sources. In one embodiment, the switches can be embedded in the waveguide channel of each partial source 12 or drive units 109.

The operation of this calibration method of the system will now be described with reference to FIG. 6, along with FIG. 2. The quasi-monochromatic radiation of one s-mmw sub-source 12a–12n of source 12 is conditioned for being easily detectable at the receiver side. This conditioning can consist in the amplitude or frequency modulation of the carrier, in the composition of a doublet spectral line. This conditioned radiation is directed on the diffuser array 14 and from there scattered to the object 16. The radiation reflected and scattered on the object 16 is then imaged by means of the quasi-optical lens 21 on the array of antenna-coupled nonlinear detectors 18. Each detector delivers a first electrical signal, which is then demodulated by appropriate demodulation circuits. The different demodulation circuits will be detailed in later sections.

Afterwards, this signal is mixed with the local oscillator signal 125 having a frequency equal to the central frequency of each frequency interval if the heterodyne detection principle is used. After this mixing, the signal is then integrated in time to deliver a second electrical signal. The time of integration is at least equal to the maximum of the sweeping time and the inverse of the minimum frequency of the interval.

This signal is multiplexed to the sampling unit 110 and after A/D conversion further processed by the pre- and main processor 111 and 113. The two-dimensional array of second electrical signals produces a partial image presentation of the target. An algorithm is implemented to calculate an average factor or another statistical quantity for normalization of the second electrical signals over all the elements of the array 18. This normalized number will be used to weigh the intensity of this frequency interval. This method of calibration is of the sequential type. By repeating this procedure for each generator 12n, the multi-frequency source is tuned over the whole frequency range of interest.

At each frequency interval a weight factor is produced. This weight factor can be directly applied to the PIN switches which are a part of the driving unit 109 (more details about this driving unit will be specified below) to tune the intensity of each source. Alternatively, the intensity of each source is kept constant and the weight factor for each frequency interval is implemented in the software for producing the image.

Another method for calibrating the system is of the concurrent type. The partial source generator for each frequency interval is amplitude or frequency modulated by a different LF signal, e.g., generated by modulation unit 108. All the frequency-modulated signals are directed towards the diffuser array 14 (FIG. 2) via the horn 107 and from there to the object 16 (FIG. 2). The radiation reflected and scattered by the object 16 is then focused on the elements of the detector array 18a, . . . 18k. Simultaneously demodulating each frequency interval with amplifying and preprocessing units 102a . . . 102n again results in the calibration or weight coefficient. Again these coefficients can be implemented in the software or directly applied to the PIN switches of the driving unit 109.

In contrast to prior art approaches, in the preferred embodiment of this invention the spectral composition of the illuminating radiation can be adapted to the dispersive characteristics of the object, its covering materials and the surroundings.

During the calibration process, glint, speckle and ringing can occur when each frequency is individually analyzed to set its amplitude. However, the averaging process over all elements of the detector array for each particular frequency interval individually cancels out all these effects.

The signal-to-noise ratio of the s-mmw signals at the receiving apparatus can be enhanced when the s-mmw sources are frequency modulated. In the simplest approach all s-mmw sources can be frequency modulated in the same way, such that at the detector side the frequency selective and demodulating circuits operating at LF can be minimized. However, modulating each source at a different frequency allows improvement of the intelligence of the system in different ways. More details about the advantages of using different FM s-mmw sources will be illustrated below.

In another embodiment of the invention, a unique imaging possibility appears that may take place only with s-mmw radiation. In this case, the wide-band multi-frequency source comprises a number of partial narrow-band s-mmw spectral lines with a large and substantially equidistant frequency shifts between each of them. At each partial spectral line a mutually statistically independent image is created, as shown in curves 184 and 186 in FIG. 7b. In this example, the amplitude image signals $v(x,f_1)$ and $v(x,f_2)$ are combined, e.g., at non-linear elements of each receiver, as follows:

$$V_{n,d}(x,t) = v(x,f_1) * v(x,f_2) * \cos[(f_1-f_2)t + \phi_{f_1,f_2}] \quad (4)$$

where $v(x,f_1)$ is the amplitude of a first speckle image for frequency $f_1$ and at receiver location point x and $v(x,f_2)$ is the amplitude of a second speckle image for frequency $f_2$ and at the same receiver location point x. The curves 184 and 186 are the intensity images $|V(x,f_1)|^2$ and $|V^*(x,f_2)|^2$ respectively recorded for the two frequencies independently. When the two frequencies are combined the following summed intensity images may be recorded $|V(x,f_1)|^2 + |V^*(x,f_2)|$.

At the image receiving side the antenna coupled mixers are conceived such that beat signals between the primary frequency distinctive signals can be generated and amplified even if they exhibit extra large frequency differences. When band pass filters, centered around the value of the equidistant frequency shift are added to the outputs of the detector array, a series (equal to the number of s-mmw sources minus 1) of statistically independent cross-correlation images 188 are created. The large frequency shift provides an enhanced visual image quality due to the strong attenuation of the speckle and ringing. Superimposed on the FIG. 7b (a–c) is the theoretical spatially and temporally non-coherent intensity image signal 180, replicating the reflection coefficient of the object under investigation. In this example the theoretical image reveals two regions of the object having a clearly distinct reflection behavior.

Figure 7A:
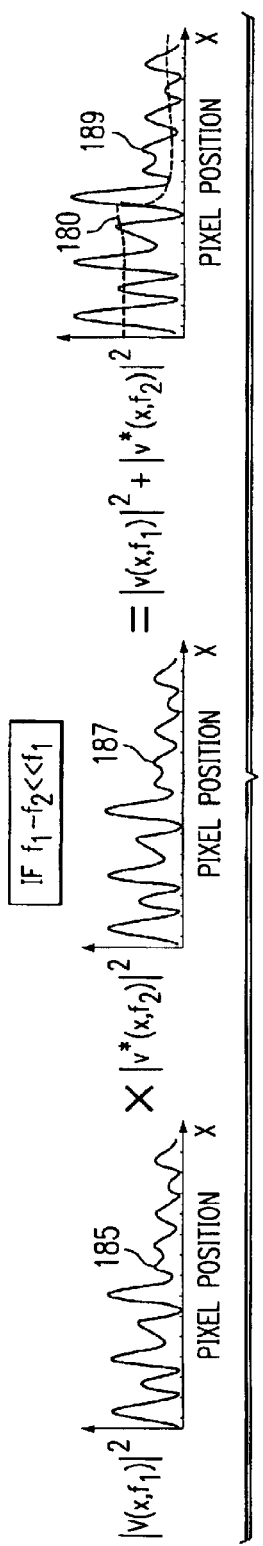
FIGS. 7a–7c illustrate the principal of two-frequency imaging.

If primary signals 185 and 187, which are responsible for two different partial images being mixed at the receiving array element, have almost the same frequencies, then the newly generated partial image being produced by beat signal 189 as illustrated in FIG. 7a, the image will exhibit the speckle structure practically analogous to the primary partial images. Because each of the primary images 185, 187 is produced by only a single spectral component of illuminated radiation, the primary images may be called one-frequency partial images. Likewise, the beat signal images may be named as two-frequency partial images.

Figure 7B:
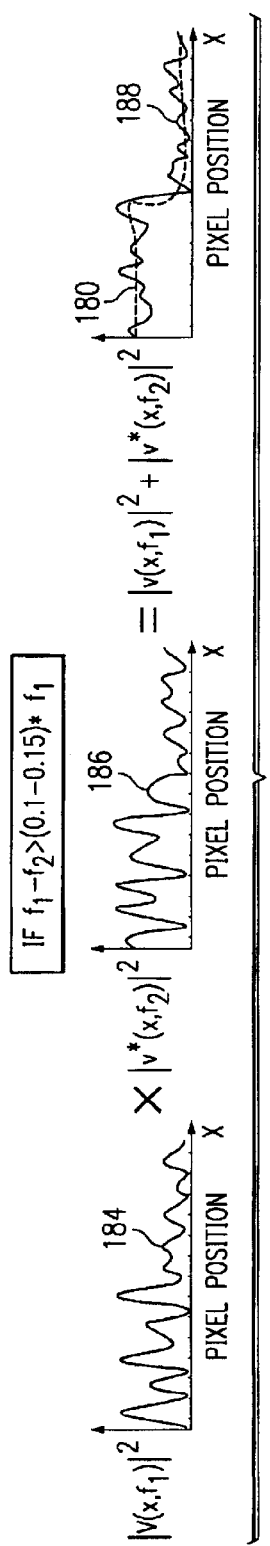

If the frequency difference between the primary one-frequency partial images is sufficiently large to produce statistically independent image spatial structures 184, 186 then the resultant two-frequency image will exhibit more smooth speckle structure 188, as shown in FIG. 7b. This curve 188 is coinciding much better with the ideal curve 180 than curve 189. The amplitude of the two-frequency image results from the multiplication of the amplitudes of the partial images. In the case where the frequencies of the one-frequency images have sufficiently distinct maximums in intensity, the distribution of speckle structure of a first one-frequency partial image is in average spatially coincident with the minimums of the second image. In this case, the generated two-frequency partial image will exhibit enhanced visual quality with smoothed speckle structure.

A possible realization of the intensity tuning of the partial s-mmw sources of this system is performed by illuminating the object frequently step by step over the whole frequency range with two simultaneously sweeping sources, separated in frequency by the frequency step. Concurrently the suitable control of the level of emitted radiation is realized. The intensity level control is needed for a correct superposition of distinct two-frequency images, but not for the constituting primary images. The spatial distribution of the two-frequency images does not depend on the absolute magnitudes of the partial image components; because the two-frequency images are the result of the multiplication of the components.

Such implementation of this embodiment is preferred for less expensive and less demanding systems since FM modulation unit 108 of FIG. 6 can be omitted and the frequency selection circuit at the detector side can be limited to one single system. This two-frequency cross-correlation imaging system can be further upgraded with a diffuser array 14 to destroy the spatial coherence of each spectral component such that angular information is added.

Figure 7C:
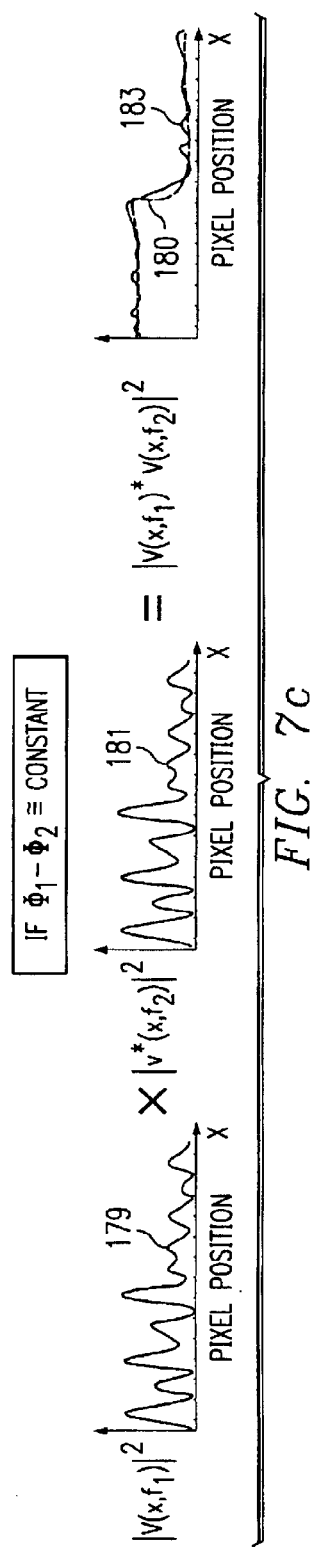

In another embodiment of two-frequency imaging, the two components of the illuminating radiation may have a stabilized frequency difference and additionally phase-locked by a steady state low noise reference signal of external or internal oscillator, which is turn may be stabilized, e.g. by high-Q quartz crystal. The details of this locking mechanism will be discussed in more detail below. These phase-locked radiation components are of great interest because along their propagation path from the radiation source 12 up to the receiver array 18, multiple scattering and reflections on the object surface 3 will not change the original phase relationship between the said phase-locked components (e.g., they propagate identically). It will be shown later that the phase relationship during further processing in the receiver array 18 is neither disturbed. These facts may be effectively exploited for speckle-free imaging which can be realised even if the observable objects (having any kind of surface roughness) is illuminated by spatially coherent radiation. This is illustrated in FIG. 7c.

The one-frequency intensity images $|V(x,f_1)|^2$ (179) and $|V^*(x,f_2)|^2$ (181) demonstrate that each one-frequency image is disturbed by speckle noise. The two-frequency image 183 produced by the multiplication of these phase-locked radiation components $|V(x,f_1)*V^*(x,f_2)|^2$, strongly approximates the theoretical non-coherent image 180.

The amplitudes of the product signals will be proportional to the intensity (and not to the amplitude as it takes place for traditional active imaging) of radiation scattered by those small parts of the concealed object at which this line of receiver elements look. It means that phase distortions in the radiation that appear due to random structure of the object's surface and which usually cause speckle structures in images in case of usual active coherent imaging, will be self-destroyed in the considered phase locked two-frequency imaging case.

Any phase-locked two-frequency images will exhibit quality of spatially non-coherent images even if spatial coherence of the object illuminating radiation will not be destroyed at all (e.g. by spatially coherence destroying diffuser 14 before interacting with the object). In other words the quality of doublet radiation images, being really the spatial distributions of beat signals of phase-locked spectrally closed radiation components at the receiver array plane, will exhibit speckle-free enhanced visual quality even if the object will be illuminated by spatially coherent radiation emitted, for example, by point-like source of the doublet line radiation. For illumination of the object from different angles even usual diffuser (a random surface reflector, the said multi-layer diffuser, or a diffuser of antenna-coupled loads with linear law response and so on), not able to destroy spatial coherence of the diffusely scattered radiation may be effectively used without any influence on speckle-free nature of the doublet radiation images. The quasi-optical performance of the lens and features of receiving array will be the main limiting factors of the image quality here. It is clear that any diffusers being able to destroy the spatial radiation coherence can be used as well, moreover illumination the diffuser, being an array of modulated antenna-coupled non-linear elements, can provides additional imaging abilities which will be discussed below.

Of course, the components of the doublets may be individually phase locked on the same reference source, but the quality of such stabilization is worse due to higher required multiplication factor of the stabilised reference signal, and this realisation is much more expensive. The stabilisation of the doublet component beat signal is the cheapest and simplest approach suitable for doublet radiation speckle-free imaging. Spectral difference of the doublet components should be small enough to provide near identical scattering and propagation through the imaging system.

Figure 8:
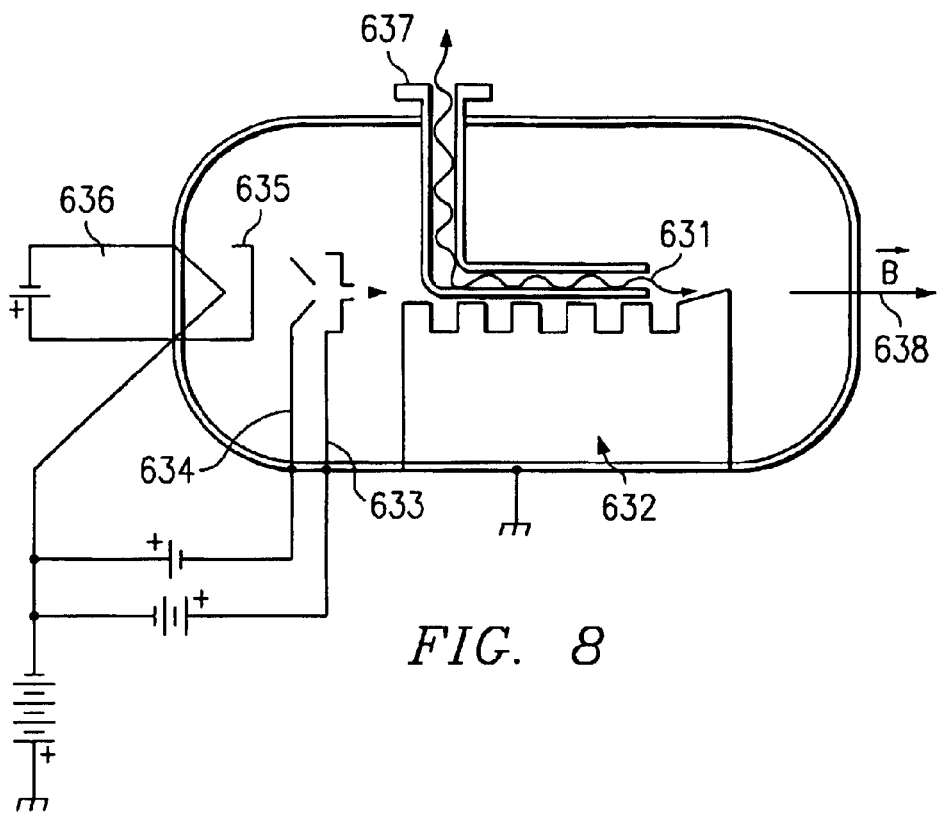
FIG. 8 is a schematic configuration of s-mmw Backward Wave Traveling tube.

As shown in FIG. 8, a backwave tube (BWT) provides another possible partial source of s-mmw radiation. A distinctive feature of such a source is the possibility to sweep the frequency of the emitted radiation over a wide spectral range in real time by means of a voltage sweep. As such, this source can be successfully implemented in the systems where frequency sweeping sources are desirable.

The operation principle of a BWT is based on the transformation of the energy of an electronic beam 631 into energy of s-mmw radiation. To obtain an effective electron interaction with the emitted radiation, the longitudinal speed of the electrons and the phase speed of the corresponding s-mmw wave should be equal. A desired element for realizing this phase synchronization is a delay line 632, which reduces the wave speed. The voltage on the accelerating electrode 633 controls the electron speed. The voltage on the control grid electrode 634 defines the beam current. The cathode 635 of the BWT and the cathode heater 636 provide the electrons. The RF wave-guide 637 directs the s-mmw towards the output of the BWT. The electron beam is focused by means of the magnetic field 638.

The backward-wave tube (BWT) is a s-mmw source with a large electronically-tunable frequency. The ability to tune the BWT electronically explains its wide usage in radio engineering and measurement devices such as sweep-generators, heterodynes, high-speed tuned clock generators and so on. By now, BWT have been designed to operate in the frequency range from about 1 up to about 700 GHz with an intensity up to 10 W (the last value is for the long wavelength range and this output power decreases with the frequency increasing) and with a frequency tuning which exceeds an octave: $(f_{max}-f_{min})/f_{mean}>0.67$. For frequency sweeping in a whole s-mmw frequency range, the BWT seems to be the most preferred building block or partial source to compose the complete spectrum. Due to its operational principles, one can change the emitting frequency of radiation up to a few tens of GHz.

Another possible partial source for the higher frequency range of the s-mmw spectrum and even for higher frequencies, is the integrated oscillator-harmonic multiplier combination. Typically, solid-state oscillators (e.g., Gunn oscillators) are very efficient low noise oscillators for the lower frequency range of the s-mmw spectrum where the power scales as 1/f due to thermal limitations. For higher frequency ranges, the power decreases much stronger with increasing frequency due to electronic limitations ($1/f^2$ rule). As a rule of thumb such oscillator sources can be used up to the limit of the F-band (140 GHz). At higher frequencies it is much more practical and efficient to combine the oscillator operating at lower frequencies, with a solid-state multiplier (e.g., GaAs whisker contacted varactor Schottky diode). These multipliers provide s-mmw radiation power by means of the $N^{th}$ harmonic generation (N=2, 3, ... 10). Depending on the tunability of the oscillator in the low frequency band and the choice of the multiplication factor a cheap widely tunable efficient s-mmw source can be realized. This combination exploits all the advantages of the basic oscillator in the low frequency range (available power, stability, low noise, ... ) at higher frequencies. For higher harmonics, the multiplication process decreases in efficiency. State-of-the-art Gunn oscillators can be tuned over very broad frequency range (e.g. 75–115 GHz). In combination with tunable multipliers an extremely extended range of frequencies is available for illumination purposes. When the basic oscillator is tunable over a frequency span $\Delta\omega_L$, then the integrated oscillator-harmonic multiplier is tunable over a frequency range $\Delta\omega_H=N\times\omega_L$, about N times larger than the lower frequency span. At the detector side the s-mmw radiation is downconverted by means of a wide band antenna coupled diode mixers.

In the preferred embodiment imaging application, sources with a continuous radiation spectrum in the required spectral intervals are most preferred. Besides conventional broadband noise sources characterized by an increased level of random fluctuations in a wide range of frequencies, more specific sources operating in the mode of stochastic signal generation can be used. A variety of possible realizations of such sources of different physical nature exist. Some of these realizations should be considered in light of their relative simplicity in practice and their sufficient output power. In such noise sources, a mode of growing stochastic oscillation with the fast-falling correlation function and wide-band spectrum of generating oscillation are realized Such modes are characteristic, for instance, for electronic-wave systems with a delayed feedback. This mode with use of traveling wave tube (TWT) will be described below.

Figure 9A:
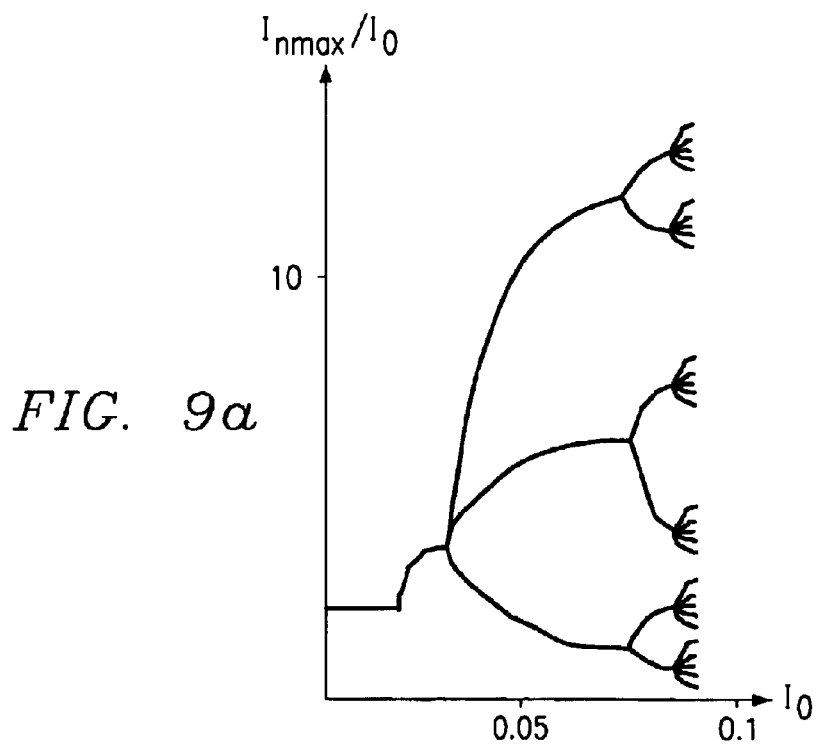
FIGS. 9a and 9b show an example of a wide-band source by means of noise-like generation in an Impatt diode.
Figure 9B:
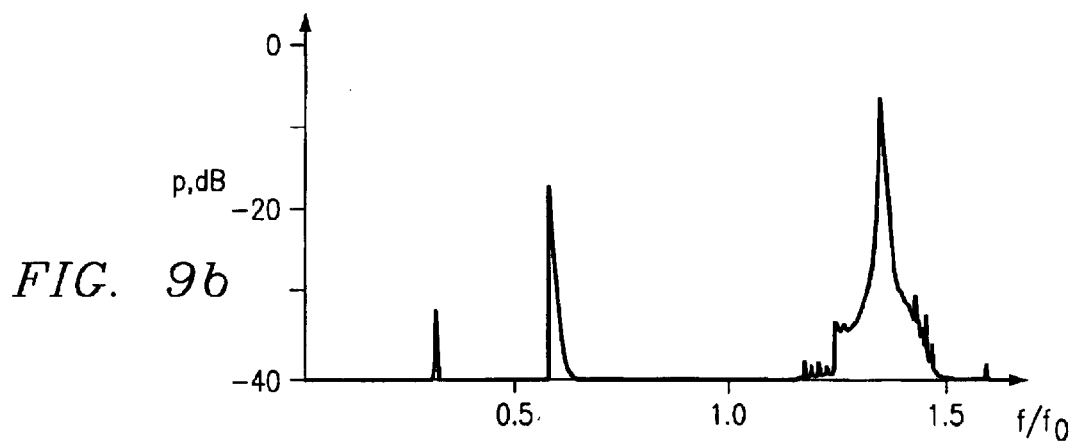

On the other hand, a similar mechanism of stochastic oscillations can appear in generators with comparatively simple oscillatory system, e.g., in the one-transit overlapped IMPATT diode. In such diodes, stochastic oscillations may appear as a result of the cascade of bifurcational reduplication of the oscillation period, as a result of complicating the self-modulation of the relaxation type, or the emergence of homoclinic orbits. Theoretical and experimental studies have shown how specific noise-like modes of radiation appear in the specific case of an IMPATT diode under certain conditions of such noise generating source. The results of such experimentation is shown in FIGS. 9 and 9b, as will be described below.

In the case of an IMPATT diode, the critical parameters that govern the emergence of stochastic oscillations are the capacitor C and the current $I_0$ in the avalanche multiplication region of the diode. Above a critical current value $I_0$ and for some range of capacitor values C, various modes of generated radiation arise. For small values of the capacitor C, the IMPATT diode exhibits a process of successive period doublings (e.g., frequency divisions) each time the current Io crosses an incremental critical current value. This doubling phenomenon is shown in FIG. 9a. In this context, $I_{nmax}$ is the current of the period-n solution in the region of avalanche multiplication. This doubling process converges fast to a chaotic behavior with the emergence of a strange attractor. The spectra of the IMPATT diode exhibiting chaotic behavior is shown in FIG. 9b. The spectra are related to the transit frequency $f_0$ of such diode and can lay in any range, representing interest for the given application. For other values of the capacitor values other modes of oscillation appear.

Figure 10:
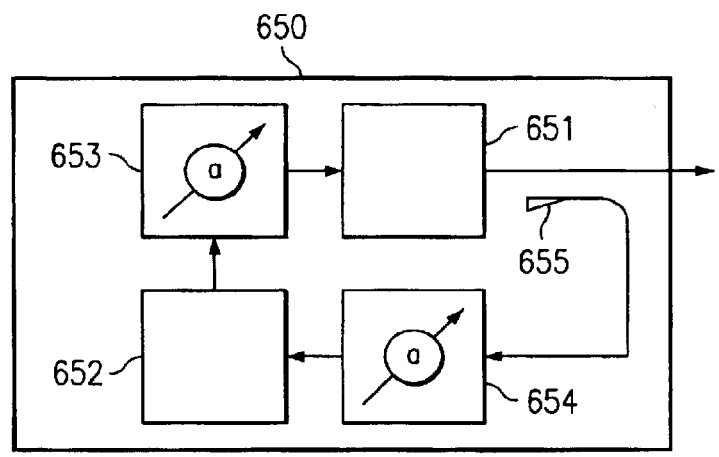
FIG. 10 is a schematic block diagram of a wide-band source, emitting chaotic s-mmw radiation based on the use of two traveling-wave tubes (TWT) with a delayed feedback.

As mentioned above, this type of generation mode is also characteristic, for instance, for electron-wave tube systems with a delayed feedback in the band of their transparency that originally gets several natural frequencies of the systems. FIG. 10 illustrates a delayed feedback stochastic s-mmw oscillator 650 that is based on traveling wave tubes. The system comprises two traveling wave tubes (TWT) 651 and 652, whose operation principle is similar to that of a BWT, a directive coupler 655 for taking part of the system radiation into the delayed feedback, and some attenuators 653, 654 for controlling the level of the radiation entering from the feedback.

The mode of stochastic generation depends on the choice of the operation mode of the tubes and transmission feedback factor. One of the tubes 651 provides a maximum amplification of signal power circulating in the system (the nominal amplification mode) while the other 652 should work essentially in a nonlinear mode. The current of the electron beam of the last tube 652 is typically one order of magnitude less than the nominal one 651 and the power of the input signal corresponds to the beam power.

Such a tube 652 works in the nonlinear mode on a dropping section of the amplitude characteristic with a drastic attenuation of the source signal, and this attenuation is larger when the signal level gets higher. The mechanism of a nonlinear stochastization of the fluctuations of such an oscillator corresponds to an essentially nonlinear mode of TWT operation at saturation on a site of the amplitude characteristic with a negative slope. The mode of stochastic oscillation is realized by increasing the feedback factor of the feedback circuit, resulting in growing non-linearity in the TWT. In this mode the spectrum of the stochastic signal takes all band of TWT amplification (651 and 652), and the resulting power of the stochastic oscillation at the system output is of the same order as the maximum power which is provided by an amplifier in a mode of amplification of a harmonic signal.

The discussed principles of noise-like radiation generation is rather general and can be realized on the basis of other partial sources, capable to work in these modes. Other sources of noise producing radiation based on other physical operation principles can be considered without any problem. Another variant is the direct amplification of signals of standard low-level wide-band noise sources (or even without any amplification). An example is a standard Impact s-mmw source acting in non-oscillating mode. It is clear from this overview that the realization of noise source, capable to emit broadband radiation in a required range of s-mmw frequencies does not present any special problems for current state-of-the-art techniques in the s-mmw range.

Figure 11A:
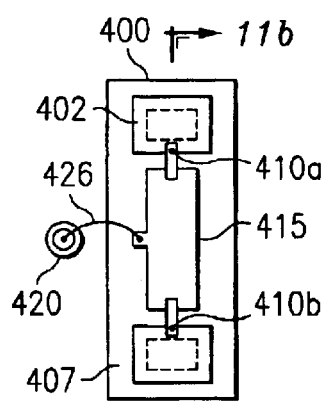
FIGS. 11a–11c are different views on a multi-element monolithic source of "polychromatic" radiation.
Figure 11B:
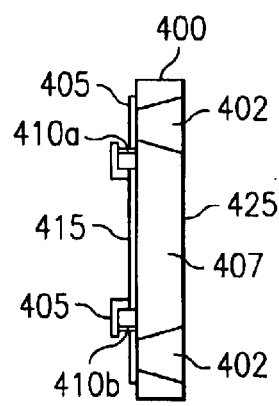
Figure 11C:
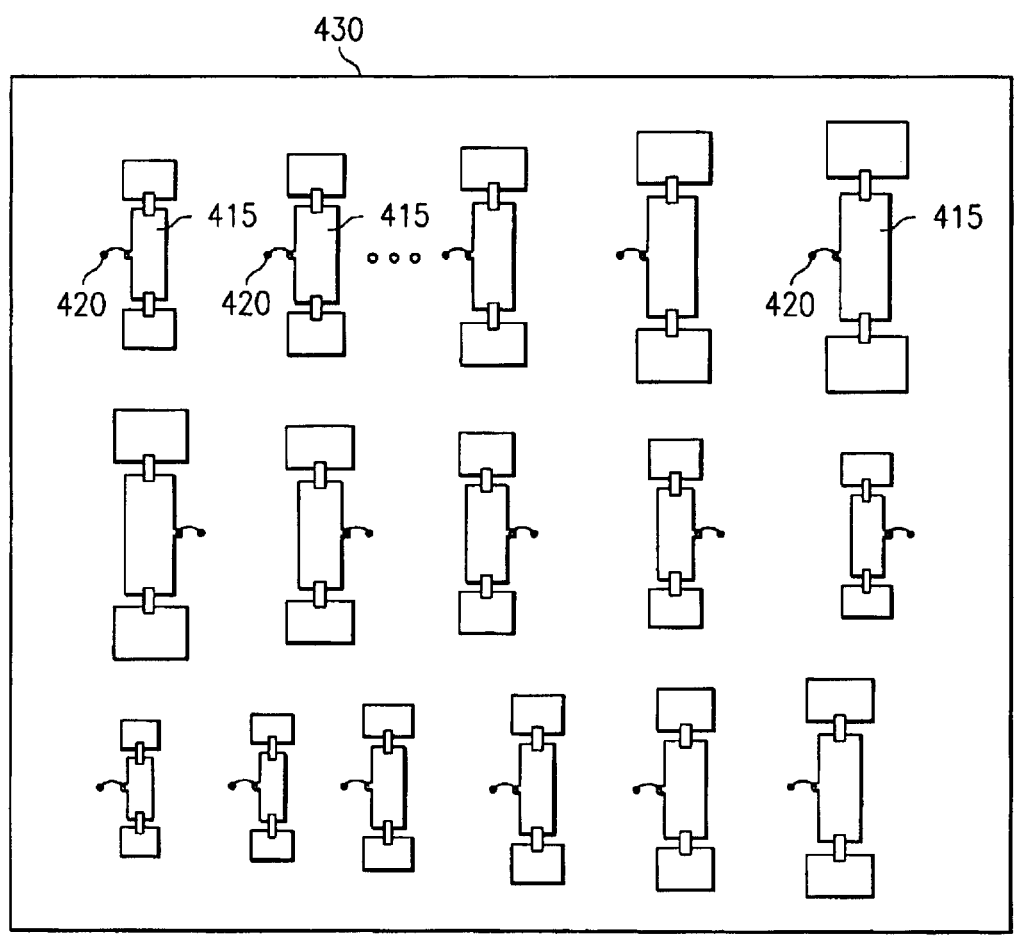

Another type of source is a multi-element monolithic source of "polychromatic" radiation. The capability of integrating IMPATT (or GUNN) diodes sources, each connected with passive resonator circuits on a single chip, also creates the possibility of realizing complex but compact monolithic subsystems at frequencies extending into mmw and even s-mmw range. An array 430 of such elements is shown in FIG. 11c. The frequencies of the individual sources essentially differ from each other, contrary to standard technology approaches. In this system, each radiating element may be fed by its own power supply and, as a consequence, be individually controlled.

Both the IMPATT diode and the resonator/antenna circuits can be fabricated on a top surface of a semi-insulating GaAs substrate. As shown in FIG. 11a, which provides a plan view and FIG. 11b, which provides a cross-sectional view, a resonator/antenna circuit 400 formed on substrate 407 includes via holes 402 that are used to ground one terminal 405 of each diode 410a, 410b. The radiating element 415, which also serves as a resonator for a pair diode, can be a micro-strip antenna. The oscillation frequency and the radiation pattern are determined by the properties of the on-chip circuitry. The bias is fed to the diodes 410a, 410b via a coaxial feed 420 from the back of the ground plate 425. A bond wire 426 needs to be used to connect the resonator 415 to the coaxial (or another type) fold.

Figure 12A:
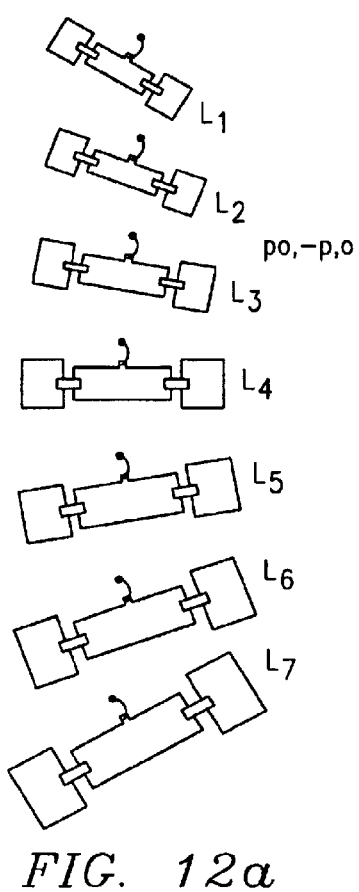
FIGS. 12a–12c show an arrangement of a multi-element monolithic source of "polychromatic" radiation.
Figure 12B:
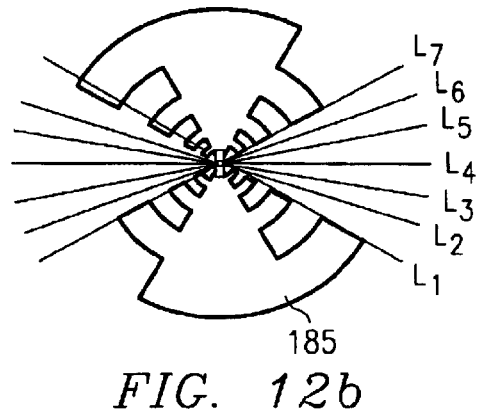
Figure 12C:
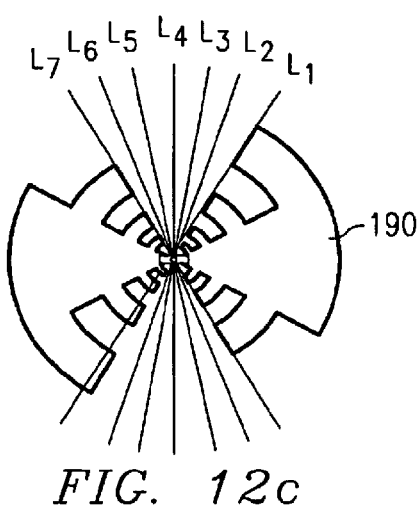

The dc current level controls the emitted power of the IMPATT diode. A "polychromatic" source 12 of radiation based of IMPATT diodes with different emitting frequencies may be fabricated as presented in FIG. 12a, which shows an array emitting the radiation with polarization features matched for a particular receiving element. When maximal signals are required at the receiver side, each diode (emitting at a different frequency) can be preferentially oriented with respect to antenna coupled receiver elements such that frequency and polarization sensitive detection is maximal for the co- or for cross-polarization state. The $L_1, L_2, L_3, \ldots$ are the directions of the best or co-polarized (FIG. 12b) of the antenna coupled receiver 185 and the worst or cross-polarized (FIG. 12c) of the antenna coupled receiver 190 sensitivity of the receiver antenna. Any other required sensitivity can be implemented by selecting the appropriate orientation for each source with respect to the receiver antennas. Each emitting element of the array may be realized as a doublet (or multiplet) spectral line source with embedded circuits for controlling the frequency shift between the doublet components (as will be discussed below).

The integrated circuit technology used to make this type of "quasi-polychromatic" source with controllable and adaptive spectrum is inexpensive and compact, providing for portable systems. This technology opens unique possibilities to have movable and/or masked s-mmw imaging installations such that concealed objects carried by persons can be investigated without the notice of the carriers.

Such a portable source of s-mmw radiation can be used in imaging systems in combination with both any artificial diffuser (which is installed in area of supervision) or even with a natural one (e.g., brick walls or other ones). The latter allows the realization of a multi-frequency imaging approach for enhanced s-mmw images. This technique can be quite sufficient in the majority of the practical cases. Since the source can be compact up to a hand held version, it can be transported virtually any place for a wide variety of applications and situations.

Figure 13:
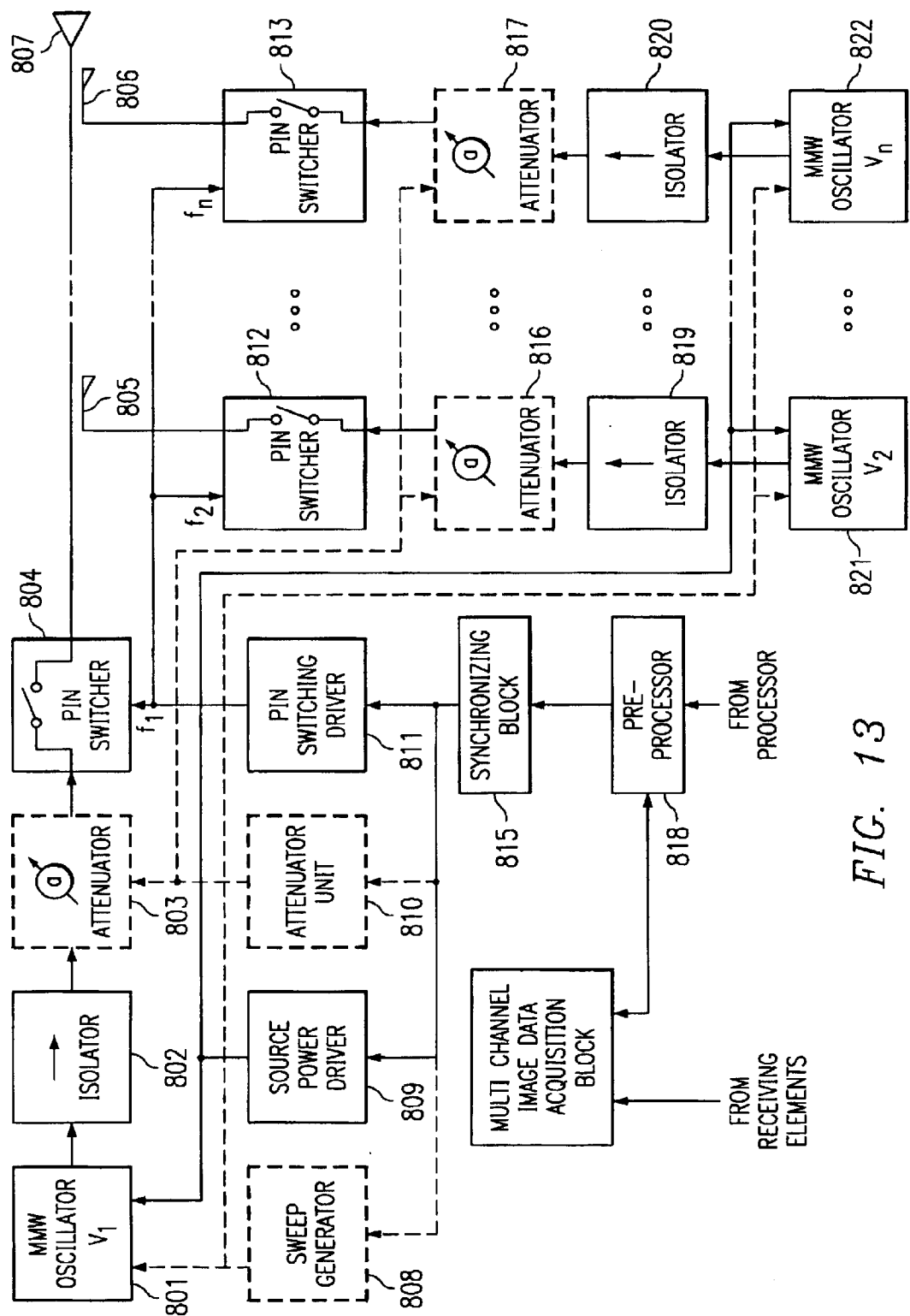
FIG. 13 shows a waveguide realization of s-mmw "polychromatic" point-like source with a controllable spectral density for real-time self-adaptive imaging.

Another embodiment, as shown in FIG. 13, utilizes a wave-guide realization of s-mmw "polychromatic" point-like source with a controllable spectral density for real-time self-adaptive imaging. Waveguide partial sources in the mmw-band (e.g., about 30 to about 300 GHz) and the s-mmw band (e.g., about 300 GHz to about 30000 GHz)

may be successfully used here. Emerging new technologies enable a person skilled in the art to extend the system to other frequency regions.

For simplicity, only a small number of fractional (partial) sources 801, 821, 822 are depicted in the FIG. 13. It is preferred that the set of sources with distinct central frequencies and spectral bandwidths is sufficient to cover the frequency range of interest (up to "polychromatic" range). Each individual fractional source emitting a narrow or limited width spectral sub-range radiation is connected with an attenuator 803, 816, 817 in order to tune the radiation intensity (or corresponding spectral density) of each fractional source individually.

Each attenuator 803, 816, 817 is controlled by the attenuator driver unit 810, which in turn is driven by pre-processing means 818 in according with the algorithm of self-adapting imaging. The information concerning the average intensities and other required parameters of every spectral distinct partial image are real-time entered into the pre-processor 818 via the multi-channel image data acquisition block 122 of FIG. 6 for realizing the self-adapting imaging.

In the case of partial narrow band sources, which are sweepable over a sufficiently wide sub-range (being distinct for the different sources), sweep generator(s) 808 is connected to the sources 801, 821, 822. Each sweep generator 808 is driven in its turn by the pre-processor 818 by means of time duration synchronizing block 815 according to the self-adapting algorithm. A source power driver 809 is coupled between block 815 and mmw oscillator 801.

All the wave-guide outputs of the partial source channels are coupled by means of coupler units 805 and 806 to couple horn 807. In this manner, every spectrally different component of the "polychromatic" s-mmw radiation is directed into free space through the same horn 807. The composite unit creates the same emission origin for each component of the radiation. This feature is preferable for imaging technologies in which equal paths for partial component fields is desirable (e.g., two-frequency imaging, doublet imaging and so on).

In order to prevent radiation coupling between the different frequency channels, they are coupled to the horn by means of isolators 802, 819, 820. The horn 807 should exhibit wide band behavior. Each partial source 801, 821, 822 can also be disconnected from the common wave-guide path by means of the PIN or the MEMS (micro-electromechanical switch) switch units 804, 812, 813 to allow each frequency interval to be calibrated independently. The switch 804, 812, 813 may also be used for implementing an additional AM, if an embodiment so desires.

The intensity of each partial radiation at each frequency sub-range can be accurately tuned by means of the waveguide attenuating elements 803, 816, 817, which are under the control of the pre-processing means 818 through an attenuator unit 810. If only frequency sweeping sources are used, these units (e.g., the attenuator, the sweep generator and so on) should be controlled with the pre-processor 818 in accordance with the self-adapting imaging algorithm. In this case, the attenuator unit 810 should be under time varying control in synchronization with the sweep generator 808 signal for providing the requested tuning of the spectral density of the emitted radiation over whole wide-band spectral range. The maximum spectrum bandwidth of such radiation is not more than bandwidth of correspondent waveguide. If the radiation with a wider spectrum is needed a plurality of sets of sources with corresponding frequency matched waveguide realization have to be used.

Each emitting waveguide partial source 801, 821, 822 of the unit can be realized as doublet or multiplet spectral line of paired sources with individual circuits for controlling the frequency shift between the doublet component. (A doublet is a pair of two closely spaced frequencies. A multiplet comprises several doublet lines which are grouped near each other in some cluster. Doublets and multiplets are described in greater detail below.)

A generalized scheme for controlling the frequency shift between doublet components is presented in FIG. 14. Two VCOs (voltage controlled oscillators) 850 and 853 are coupled through dynamic feedback, which allows their frequency difference to be obtained at mixer 846 and to be amplified by amplifier 848. Using commercially available high speed frequency dividers 849, the generated intermediate frequency (IF) is divided down up to the megahertz region and, after amplification and filtering, its output is sent into the digital frequency discriminator 852. The error voltage from the discriminator 852 is fed into the differential amplifier 855, together with some LF modulation and biasing signal. The differential amplifier 855 drives one of the VCOs 853. The other oscillator 850 is biased by a constant voltage source. The couplers 841 and 842 are used in a waveguide realization for unifying the energy of both VCOs 850 and 853 in one waveguide.

Figure 15:
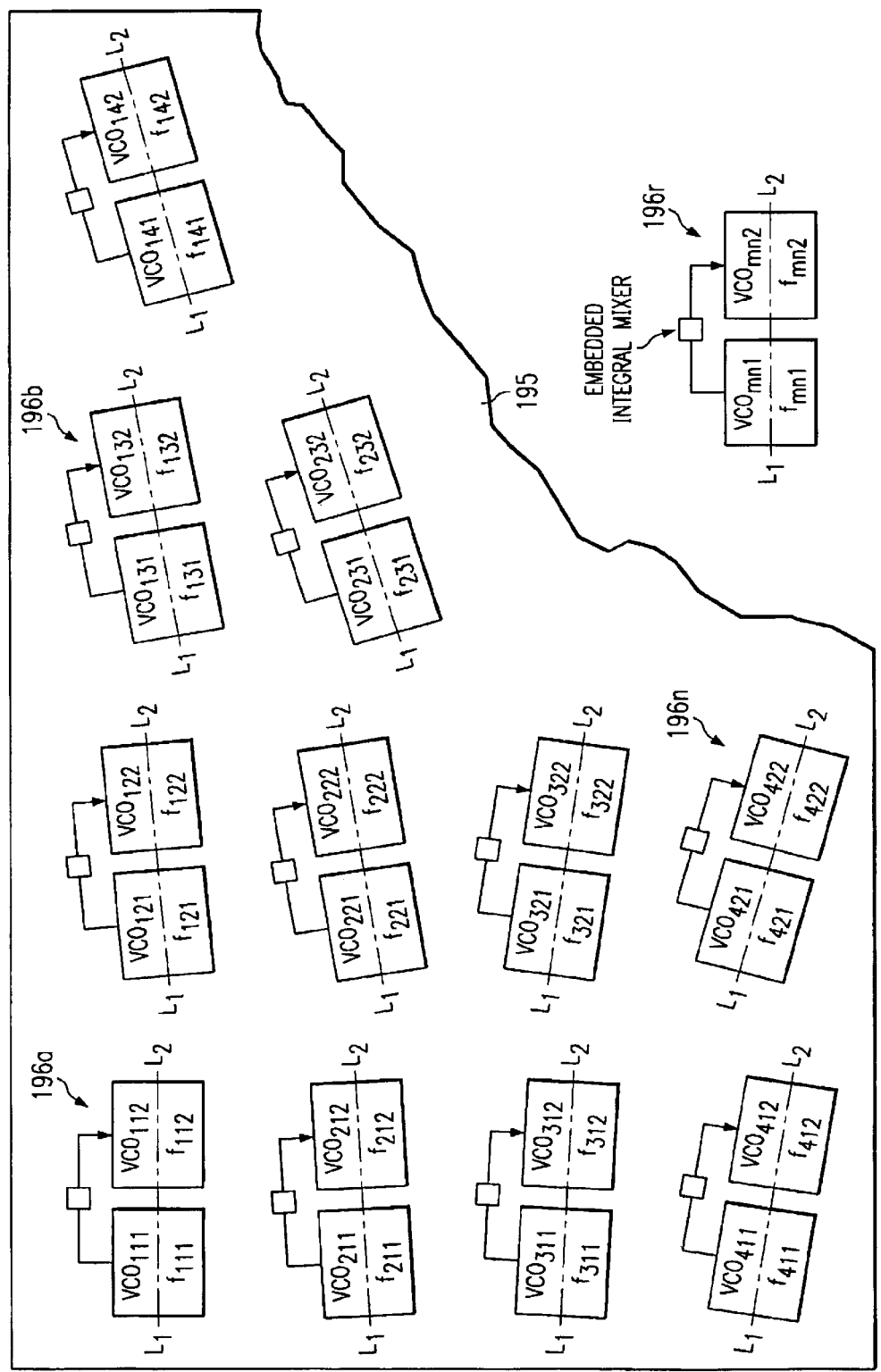
FIG. 15 shows a top view of a monolithic realization of s-mmw radiation composed of doublets with particular polarization states.

For a monolithic realization 195, part of the elements 196a, 196n may be located directly at the plane of paired VCO. This is shown schematically in FIG. 15. Here the IF and LF signals processing scheme may be located out of the emitting plane.

II.bis Pre-diffuser-multiframe

In a further embodiment of the invention another additional possibility (typically for the s-mmw spectral range) for enhancing the visual quality of quasi-optical images is exploited.

A principle of enhancing the visual quality of an image of an object, disturbed by radiation coherent noises, includes the accumulation of multiple speckled images of the object so that each speckle image has statistically independent speckle structures. It has been noted above that changing the frequency of radiation being emitted from the same space point leads to obtaining such statistically independent speckle images and their following accumulation allows the reduction of speckles in the resultant image and, as a consequence, enhances the image visual quality.

An alternative, or additional, approach is to change the space locations of the diffuser radiation scattering element relative to illuminated object without changing the frequency of the radiation. These changes of the diffuser element locations lead to changes of angles of radiation incident on object surface that in turn change relative optical paths of the radiation from the diffuser scattering element up to the nearest points of the object surface. These object's points from the same pixel of the image, are processed through the imaging system within a particular receiving array element that is responsible for the image pixel.

Due to the latter, the phase differences of the radiation scattered by said nearest point will be redistributed causing changes in the speckle structure of correspondent partial image. The phase changes will take place even for the same frequency of illuminating radiation.

To provide a plurality of partial images for processing (e.g., for accumulation to reduce speckle and ringing), the spatially extended array of scattering elements can be used. The phase difference of radiation scattered by different elements of the array are time-varied and should vary over more than $2\pi$. Therefore, the receiving apparatus of the imaging system should utilize an equivalent "exposure" time that is longer than the characteristic time duration of the phase variations.

In this case the distinct partial image will be accumulated in intensity so as to lead to the speckle reduction. Contrariwise, the radiation of different partial images will save mutual coherence (meaning that they will have constant mutual phase shift only) and will be accumulated in radiation amplitude only. The latter is known to lead to obtaining only a new speckle image without any enhancement of its visual quality.

Speckle intensity distribution in the partial image depends on structure features of an object surface (that cannot be changed) and the angle of incidence of the partial radiation (that depends on position of the scatterer at the array plane). In order to obtain multiple speckle images with statistically independent speckle distributions, the system should include a sufficiently large array of the scatterers. Accordingly, typically the array sizes are preferably not less then 0.5×0.5 $m^2$ for practical cases of s-mmw imaging contraband detection.

Whereas changing the frequency of the illuminating radiation is equivalent to reducing a temporal coherence of the radiation, changing the angles of radiation incident in the observable area is equivalent to reducing a spatial coherence of the radiation in the area. Accordingly, the scatterer array may be considered a diffuser destroying spatial coherence of radiation incident. Reduction of the radiation spatial coherence will be more important if the diffuser sizes are larger.

The array may be illuminated by radiation being preferentially polarized in particular plane (or even linear polarized). Depending on the realization of scattering elements, the scattered spatial non-coherent radiation may serve polarization properties of primary radiation. Moreover, the scattering element may have wide-band performance. In this case, the observable object may be illuminated by totally controllable wide-band spatial non-coherent radiation ("white light") with needed polarization state of every radiation components.

Therefore, unlike optical imaging and illuminating systems, the proposed s-mmw systems possess essentially greater imaging capacities for enhancing image quality. The s-mmw diffuser may include specially designed multiple point-like scatterers electronically controlled which scatter incident radiation by independent but controllable manner. Such diffuser really decomposes the radiation over set of multiple partial components with distinct angular propagation in area of observable scene. Every such component may be distinctly coded by modulation signals applied to every distinct point-like scatterer of the diffuser.

It should be noted that in the proposed approach, non-coherent imaging may be realized by simply digitally summing the partial images containing the partial radiation components scattered by spatially different scatterers of the diffuser. In this case, the information about mutual phase between partial image's radiation components will be inherently lost as it reacquired. The procedure of summing the partial images by digital means is equivalent to non-coherent accumulation of radiation by integrating analogue receiver apparatus. Of course, the number and kind of the partial images have to be not more then it is necessary for truth detection goals. The partial images accumulation in the aforesaid procedures both digital and analogue types may be applied jointly in more or less degree in according to the goals of particular imaging application.

In a further embodiment of the invention another additional possibility (typically for the s-mmw spectral range) for enhancing the visual quality of quasi-optical images is exploited.

Because the basic principle of enhancing the image quality consists in the accumulation of multiple statistically independent speckled images, which contain deterministic spatial information about the imaged objects, any additional approach in independently obtaining such images will contribute in complementarily way to the realization of the goal.

A method of shortly changing a foreshortening of observed objects relative to the input pupil of the imaging systems might be successfully used for it. Even small changes in orientation of the object's complex surface relative to said input pupil may lead to essential redistribution of relative phases of radiation fields scattered by different surface parts (different for different spectral intervals that is able additionally to increase the possibilities of multi-frame technique), that will cause changes in spatial speckle structure of corresponding partial images.

Because true spatial information about an object in slightly reoriented images of the object will be practically the same (when the frame rate is sufficiently high) and, at the same time, their speckle structures will be distinctly different, the set of such images (technique of fast frames) is a complementary one for the procedure of enhancing the resultant image. This technique is attractive when the system allows fast recording of multiple frames for contraband detection due to the fact that any human carrier of the contraband practically always makes involuntary body movements, even while standing still, and, of course, when in motion. These movements allow a set of snap partial images (frames) with different speckle distribution for the nearest foreshortening of an observed object. The rate of obtaining of such frames of the image should be rather high, for providing of snap of rather small changes of object foreshortening. These conditions are acceptable for s-mmw imaging apparatus where the acquisition rate may be higher than 1 $\mu$s per frame.

In this case, the possibility of further enhancement of vision quality of the resultant images will complementarily appear. Moreover it is quite possible to force a human contraband carrier to perform the desired movements in an area of observation, including, for example, their forced turn in front of the imaging system due presence of special traffic-directing fences along proposed person movement through the area of observation.

Any joint usage of adaptive, temporally and/or spatially non-coherent illumination (as a matter of fact a "white" source) in combination with multi-frame imaging techniques will yield a multitude of enhanced image quality effects due to the mutual statistically independent characteristics of the partial images. This usage is utilized in some embodiments of the present invention. The adaptive complex s-mmw illumination radiation of these embodiments yields high visual quality images due to the fact that firstly an increased number of independent partial images may be available and secondly that their combined usage can be controlled by digital processing means as well.

This combined approach contrasts with prior art systems because the prior art systems obtain only partially some coherence destruction, and this in a much more complicated and expensive way.

III. Diffuser

As discussed above, the preferred embodiment of the present invention utilizes an electronically or optically controlled diffuser 14. As shown in FIG. 2, coherent radiation 24 from source 12 is directed towards the non-movable but electronically (or optically) controllable diffuser 14 which is preferably intended to destroy spatial coherence of radiation incident on it. In this context, non-movable means that the diffuser 14 does not need to rotate as a whole for achieving the reduction of the spatial coherence. Any essentially movable unit, especially a bulky unit, dramatically limits the number of applications that can use the imaging system. As a result, it is desirable to avoid movable units, as is done in this embodiment.

As was discussed above, for applications that employ multi-frequency imaging, it may be difficult to find a suitable wide-band diffuser. If the range of spectrum of the radiation being used for the illumination of an object is sufficiently wide, rotating diffusers made from corrugated metallic surfaces become very difficult to fabricate such that they are efficient over the whole spectrum. For radiation with wavelengths that are distinct from characteristic sizes of local roughness of the corrugated surface, the diffuser will mainly exhibit mirror-like reflections. To overcome this problem, a novel kind of antenna-array diffuser may be used as explained below.

Any approach for realising a diffuser which is a non-movable and concurrently able to destroy the spatial coherence of spatially coherent multi-frequency radiation incident on the diffuser is very attractive for a majority of s-mmw imaging applications. The preferred approach is to employ a multi-element array of conductive structures, which have multiple ports (or only single port) loaded by time-varying impedances. In this context more generalized terminology of loaded scatterer, which is defined as an object having one or more terminal pairs (or ports) to which impedances are connected. Depending of the size of the scattering object, one can refer to a lumped scatterer or a point scatterer. A particular kind of scattering object is a conductive structure. A spectrum of the s-mmw fields, scattered by the structures, exhibits a particular composition. Typically, the spectral line(s) of the incident radiation in combination with additional spectral-lines are shifted in a well defined way relative to the primary spectral line(s). If said impedances are periodically changed in time then values of the frequency shifts are multiples of the frequency of the periodical impedance variation.

If one takes antennae as the conductive structures, such that a load is connected across a pair of conductive elements of a correspondent antenna, then the diffuser can be considered as an array of antenna coupled loads whose impedances are modulated in a time-varying manner. The scattering properties of the diffuser are typically defined by the type of antenna, which may be flexibly adapted to a concrete application. In particular, when one chooses quasi-complimentary geometries for the antennas, they operate over a very broad spectrum and hence ideally suited for multi-frequency imaging.

Figure 16:
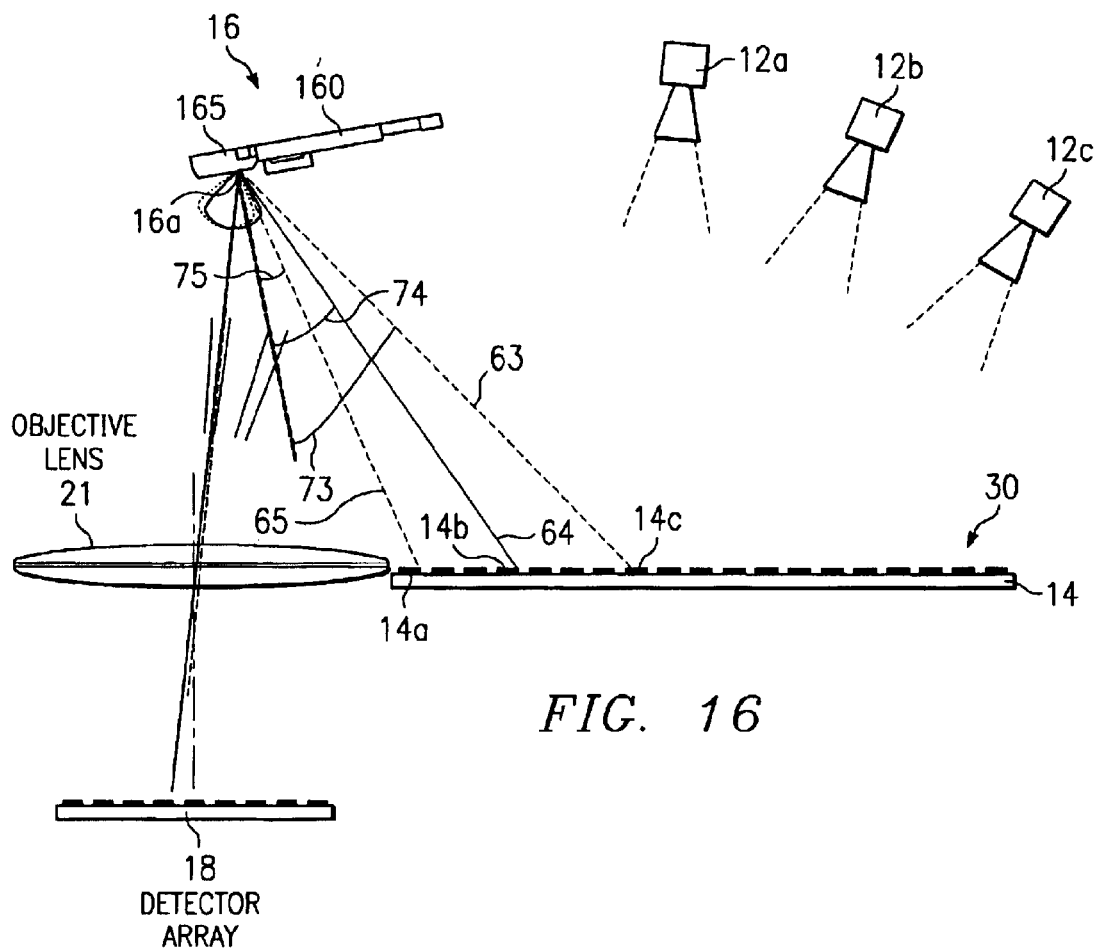
FIG. 16 shows schematically the topological lay out of the set-up for angular encoding of the radiation scattered by the diffuser towards the object.

FIG. 16 illustrates a diffuser array 14 that is based on this operation principle. In this example the diffuser array 14 is a two-dimensional array. The elements of array 14 are preferably impedance loaded antennas 30, one such antenna being shown in FIG. 17a. The frequency bandwidth of these antennas 30 is selected in accordance with the radiation of the s-mmw source 12 (or sources, if more than one source is used). The incident spatially coherent radiation 24 (FIG. 2) is converted in scattered spatially non-coherent radiation 26 by the electronically controllable elements of the diffuser array 14. The scattered radiation is primarily directed towards the object 16.

Figure 17A:
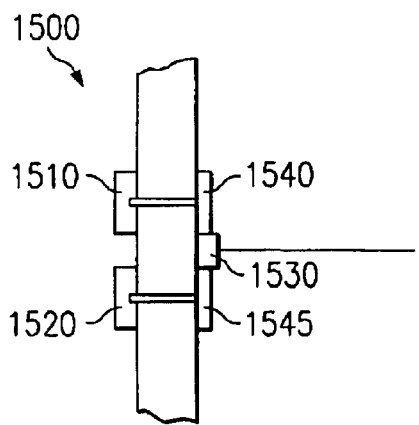
FIGS. 17a–17c are cross-sectional views of an antenna coupled element of a diffuser array.
Figure 17B:
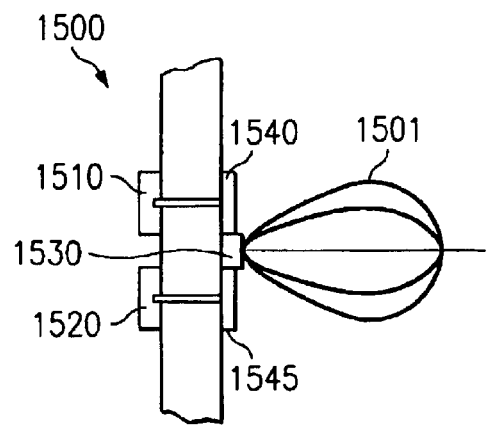
Figure 17C:
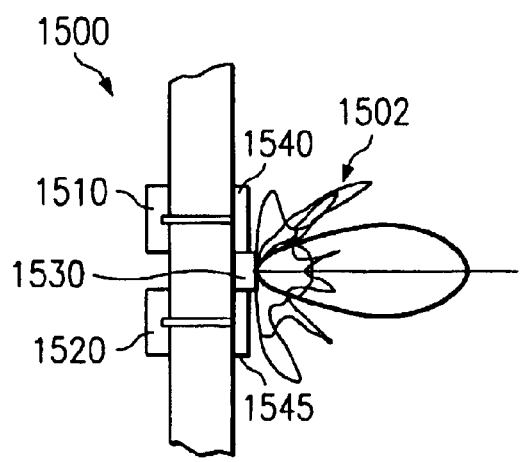

FIG. 17a illustrates a cross-section of one impedance-loaded antenna element 1500 (labeled as element 30 in the array 14). FIGS. 17b and 17c show the same antenna element 1500 along with typical radiation patterns, as will be discussed below. In this embodiment, each impedance-loaded antenna comprises two conductive antenna parts 1540 and 1545 and is equipped with two contacts (or ports) 1510 and 1520, which may provide a bias (when it is needed) and/or a LF (low frequency) modulation signal for driving a load impedance of the scattering element. When the impedance of the load (which can be some nonlinear element) 1530 is fully matched to the impedance of antenna element 1540/1545, the incident radiation is scattered in some "specular" way (in accordance with the antenna pattern) as shown by the scattering indicatrix 1501 in FIG. 17b. In the case where the load is completely mismatched, the scattering indicatrix 1502 being primarily "specular" becomes essentially more "diffuse". This latter case is shown in FIG. 17c. Because such changes of scattering properties of the diffuser elements in time can be realized independently of each other by means of independent modulations of their loads, the radiation scattered by the whole diffuser appears to be diffuse and spatially non-coherent.

By switching the load between matched and unmatched impedance values, the radiation field scattered by the element 1500 can be controlled and modulated. Applying an electrical or optical modulating signal to the combined scattering element 1500 can perform the impedance switching.

The antenna scattering patterns depend on the magnitude of the impedance of the antenna load 1530. This impedance can be matched or mismatched with the antenna 1540/1545. Moreover, specific impedance values (including reactive loads) are known in the art to be able to decrease the level of scattered radiation, scattering in particular directions, up to negligible values. This effect is similar to techniques used in radar and satellite applications where the back scattering cross section of coherent radiation can be controlled by driving the antenna load.

The impedance load 1530 of the antennas 1500, and the principle of their modulation, can be different in nature. As examples, the loads can include Schottky diodes or Bismuth bolometers, or even two-terminal to three terminal micro-electromechanical switches (MEMS). The loads can also go from photo conductor up to phototransistor. In practical implementations the elements of the diffuser will be similar. Accordingly, while specifically included as an aspect of the present invention, it is unlikely that a combination of bolometers, P-I-N diodes and photoconductive elements would be commercially practical within a single diffuser 14.

Different approaches exist for realizing the modulation of the loads of the antennae. The bolometer resistance, for example, can be changed due to resistive heating and cooling by a modulated (e.g., LF) electrical signal, for instance, applied to the load 1530 through the antenna ports 1510 and 1520. The modulation signals may be applied to the antenna elements through coils designed such that electrical modulation signals are perfectly transmitted and the millimeter wave radiation signals perfectly blocked.

Another approach of the load modulation can be realized with the principle of modulating a photo-conductive load by optical modulation signals, which can illuminate the loads through correspondent holes in the array substrate. The principle of optical modulation provides an advantage in that the circuit does not require any LF electrical networks to be connected to the antenna elements. Such networks can affect the RF performance of radiation scattering elements (antenna coupled load) and cause some limitations on the topological properties of 2D array configuration when both the scattering elements of the array and correspondent LF circuit leads have to be located at the same plane. The latter takes place when all elements of the array are disposed on the same side of a dielectric substrate.

When no modulation signals are applied to the elements of the diffuser array 14, the spatial coherence level of the radiation emitted by the s-mmw source will be unchanged and remain very high. In that case, the rough surfaces of the object are known to introduce random distortions of intensity levels in the image at the receiver array plane due to the speckle effect. By distinctly modulating the impedance 1530 of the differently located elements 30 (1500) of the diffuser array 14 the back-scattering cross sections of the different array elements are distinctly modulated and hence this embodiment allows the destruction of the spatial-coherence of the radiation and, as a consequence, the minimization of the speckle distortions in any obtained s-mmw image.

The modulation signals for different components of decomposed radiation (including radiation decomposed over different angles of component propagation) can be ordered in some defined manner to encode information on physical features of said radiation components. Such information can be very important for true object detection because the surface of an observable object (and/or its internal structure) will scatter the radiation components with distinct physical features in a distinct manner. Partial images of the object generated by some such components (or limited set of such components) may contain characteristic details on the object sufficient for true object recognition. The concept of encoding and decoding information within the radiation signals will be considered in greater detail below.

In the preferred embodiment, the coherence features of the object illuminated radiation are strictly under (opto) electronic control. The low frequency modulation of loaded antennas 30 that are spatially distributed provides a much more effective and essentially less expensive approach for the destruction of radiation spatial coherence. This statement is especially true compared with prior art systems where, e.g., a mechanically rotating surface of roughed metal is used or where an extended array of s-mmw sources is provided, each emitting s-mmw radiation with a slightly different frequency.

In the preferred embodiment of the invention, the principle of modulating the load impedance of wide band antennas is used for controlling the level of the radiation spatial coherence scattered by the antenna array. Controlling the scattering properties of the diffuser elements may be optimal for various characteristic impedance of the load mainly depending on type of antenna employed. Loads that exhibit a resistance, a capacitance, an inductive or complex impedance, or even a negative resistance can be used as an antenna load. Some examples for the loads are Schottky diodes, P-I-N diodes, MEMS (micro-electromechanical structured)-switches and bismuth bolometer resistances. The impedance values can be modulated by harmonic or two-state (binary) signals. In the case of the bolometers, the resistance change is achieved by heating and cooling with a power-modulating signal.

The radiation 26 (FIG. 2) scattered by such antenna array 14 will contain spectral components, which are shifted relative to the carrier frequency of incident radiation. In an ideal system, these frequency shifts are strictly equal to the frequencies of the modulating signals applied to the different antenna coupled loads. A multi-element array 14 of impedance loaded antennas with different modulation frequencies for spatially distinct elements 30 is able to scatter spatially non-coherent radiation even if the different antenna-coupled loads are modulated with only slightly different frequencies of modulation signals. The later is especially valid if the receiving apparatus of the imaging system can provide duly temporal integration of the received signals. The integration procedure, which can be realized in different ways, aims to eliminate any inter-modulation products of different spectral components of the electrical signals. The latter can be important if only energy of the spectral components is responsible for energy of the correspondent partial images.

Generally the modulation signals may exhibit different spectral signatures. In any case, the induced frequency shifts should be sufficiently smaller than any intentional existing frequency differences between different spectral components of the incident radiation in order to avoid any destructive frequency overlapping of the spectral components. This means that after the radiation is scattered on the diffuser array, the produced spectral components of the scattered radiation can be reasonably resolved by the frequency selective means (e.g., filters or Fast Fourier Transform) of the receiver apparatus.

Each image produced by a particular spectral line of the radiation illuminating the diffuser exhibits an enhanced visual quality as the radiation of primarily totally coherent radiation of the spectral component is transformed into the spatially non-coherent radiation after its scattering by the diffuser.

The possibility of distinct modulation of radiation components scattered by different elements of the diffuser allows the realization of a principally novel imaging technique based on encoding and decoding information on angles of propagation of multiple partial components of object illuminating radiation. This modulation principle can be extended to encode/decode information upon any physical features of radiation components (e.g., carrier frequency, polarization state and so on) as will discussed below. It allows essentially enhanced detection capabilities of s-mmw imaging contraband detection systems.

When the spatial spread over the array and the values of the modulation frequencies are well chosen and dynamically controlled, even more new imaging possibilities appear. One can assign to each antenna or cluster of closely spaced antenna distinguishable modulation frequency characteristics. This technique is useful for encoding and decoding of information, as will be discussed below.

Other modulating techniques may alternatively be used for realizing non-coherent illumination of the observation scene. Amongst these techniques exist methods of modulating resonant scatterers that cannot be used with non-resonant ones. Since a resonant scatterer has a high quality factor Q, large changes in scattered radiation will result even if only small changes are induced in one of the following tuning procedures: (a) small tuning of the reactance of the antenna, (b) small tuning of the scatterer dimensions, or (c) tuning of the scatterer's illuminating radiation frequency.

To utilize tuning procedure (a), the tuning reactance may be changed either mechanically or electrically. To utilize procedure (b), any vibration (including a usage of acoustic wave generators) of the scatterer allows the modulation of scattered radiation. Such a scatterer might be made mechanically resonant for the modulating frequency as well as resonant at the s-mmw radiation frequency. For tuning procedure (c), the frequency of the illuminating radiation should be swept in time. Only a small frequency deviation of the order of 1/Q is needed for modulating the scattered radiation of each antenna.

When the multiple high-Q scatterers are sequentially tuned in time, then the array may be used for realizing of non-coherent illumination. Careful choice of tuning parameters for each set of spatially distributed multiple scatterers allows the creation of a diffuser instantly scattering only in limited and spatially distinct points of its surface. Scanning the tuning parameters of the high Q-scatterers over the whole area of the diffuser and sequentially in time lea&s to sequentially scattering the radiation by all spatially different points of the diffuser. Due to scattering radiation sequentially, the information about mutual phase of partial radiation scatterer by spatially distinct point will be lost. Of course, the receiving apparatus should have signal integrating circuits over the time of scanning.

Figure 18A:
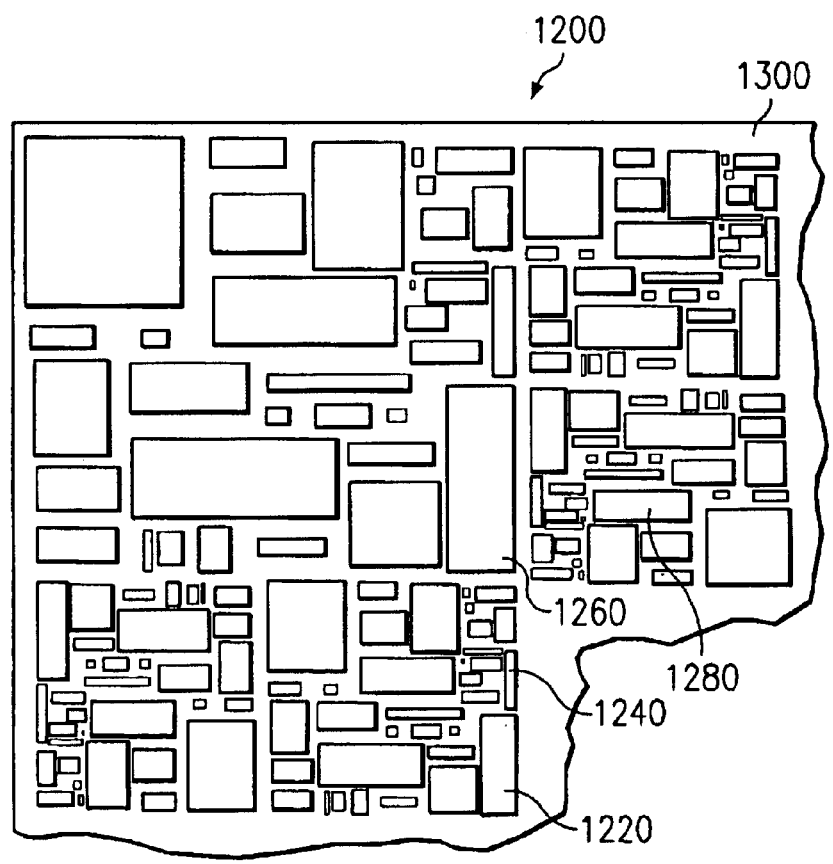
FIG. 18a is a top view on a high-Q resonant antenna set diffuser for destroying the spatial coherence of radiation.
Figure 18B:
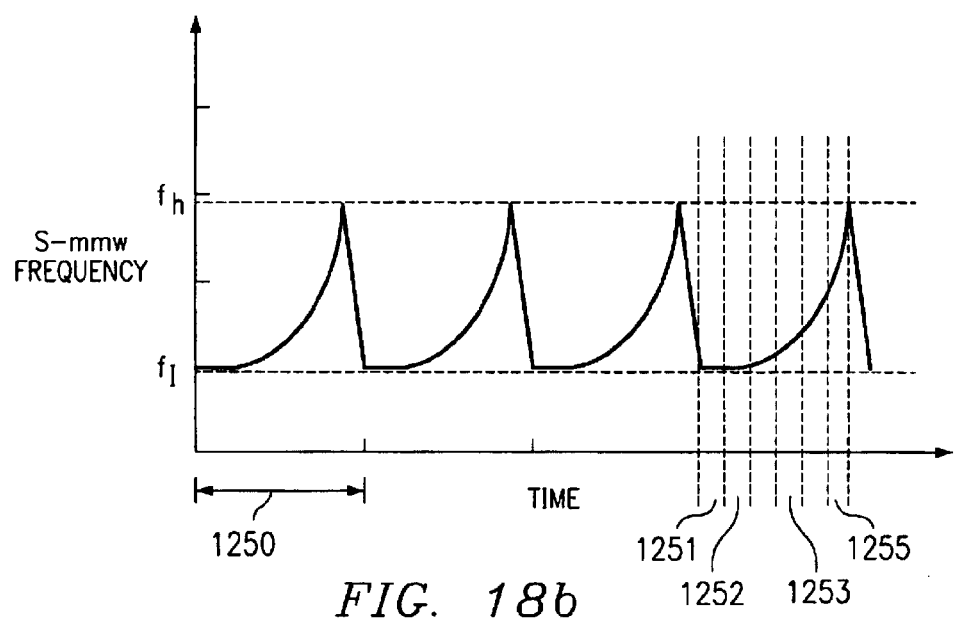
FIG. 18b is a graph showing temporal evolution of source sweeping over frequency range of antenna elements of diffuser

FIG. 18a illustrates a possible realization of this type of diffuser 1200. A set of randomly located rectangular passive high-Q antennae 1220, 1220, 1240, . . . , 1280 on a thin dielectric substrate 1300 with distinct central resonance frequencies is illuminated by radiation the frequency of which is varied in time between a lower limit $f_l$ and a higher limit $f_h$ (see FIG. 18b as well). In the preferred embodiment, the spectral range of the scanning is more than the range of the antennae central frequencies. This simple realization generates non-coherent illumination. This arrangement should provide a sufficiently high Q performance of partial antennae. If the frequency range of scanning is limited, only the spatial coherence of the scattered radiation is substantially reduced. If, however, the frequency range of scanning is sufficiently large, then the scattered radiation will be both spatially and temporally only partially coherent.

When the integration time at the receiver side is as large as the scanning time 1250 of the source, a single image with reduced spatially and temporally coherent noises is generated. If the total integration time 1250 is split in to different time slots 1251, 1252, . . . 1255, a number of partial images can be received at the receiver side. Each of these partial images will have a smaller reduction of the speckle noise than the image obtained after a full integration period. But when the resonant frequencies of the antennas are geometrically well organized, partial images obtained after partial integration can be identified featuring substantial glint noise. When the principle of weighted summing is applied here, the partial images substantially destroyed by the glint effect can be eliminated.

Figure 19A:
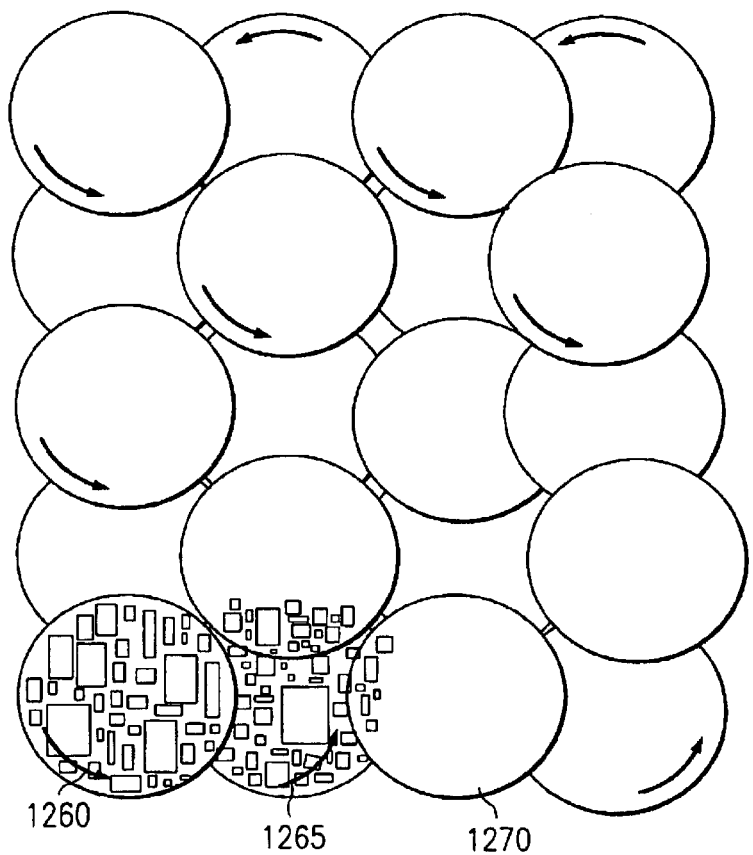
FIG. 19a is a top view on a high-Q resonant antenna set diffuser comprising independent rotating subarrays.
Figure 19B:
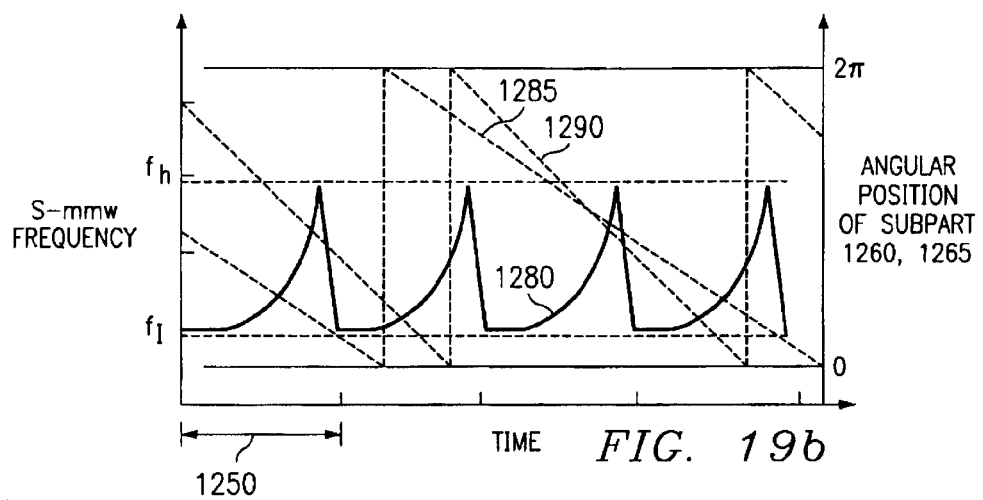
FIG. 19b is a graph showing the combined temporal evolution of source sweeping through its frequency range and the angular position of the rotating subarrays.

A further reduction of the spatial coherence can be obtained when the diffuser of passive high-Q antennas is divided in to a few parts 1260, 1265, 1270, which can independently rotate with respect to each other as shown in FIG. 19a. The whole diffuser area is at every instance in time exposed to the s-mmw radiation. By having at least two levels in the z-direction perpendicular to the surface of diffuser surface, all the diffuser subparts can rotate freely with any obstruction. When the sweeping cycle for the s-mmw source is a few times repeated while the subparts of the diffuser rotate, the spatial coherent noises of the obtained image might be further decreased, as the different subparts of the diffuser were illuminated in other geometrical positions at the same moment in time of each periodic cycle. This is achieved when the rotation of the subparts and the sweeping of the source are asynchronous (e.g., out of phase) as illustrated by the frequency sweeping curves 1280, and rotation curves 1285, 1290 of the subparts 1260, 1265 of the diffuser in FIG. 19b. These subparts can rotate slowly as only a few snapshots during the spectral sweeping of the source are required. The rotation of the small disks is not like in the case of the bulky mechanical rough disk. Here one only waits to obtain N positions of the disk to obtain N-times more statistically independent images.

In another embodiment, a simple realization of a spatially coherence destroying diffuser is based on the usage of elements allowing electrically changing the distance between a particular radiation scattering element of the diffuser and the total diffuser substrate. The range of the distance changes is not more than half of longest wavelength $\lambda_{max}$ of used wavelength spectrum.

Figure 20A:
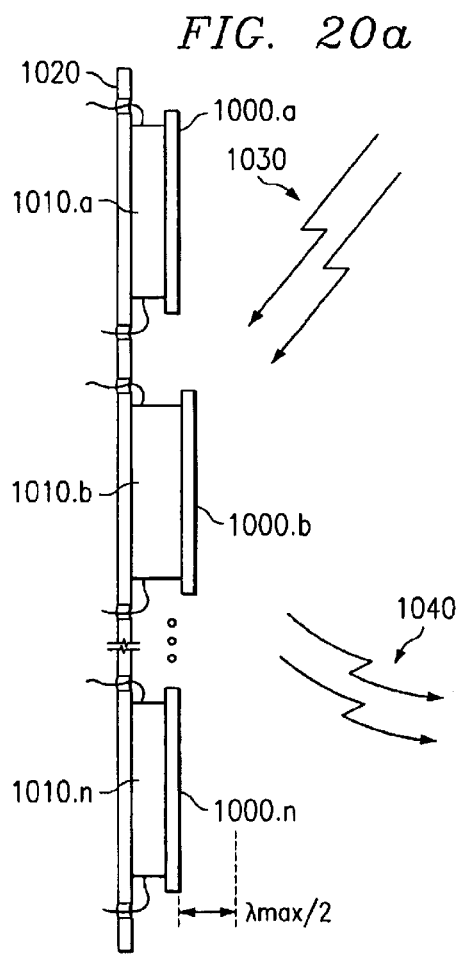
FIGS. 20a and 20b are side views of spatial coherence destroying diffusers based on mechanical displacements (piezo-electric driven actuators for FIG. 20a and electro-magnetically controlled spring-coils actuators for FIG. 20b).

One possible realization is shown in FIG. 20a. The scattering elements 1000.a, 1000.b, . . . , 1000n, or a set of them, are disposed on piezo-electric actuators 1010a, 1010b, . . . 1010.n that are able to change the position of the radiation scattering elements perpendicular to the substrate 1020.

The actuation of the piezo-electric elements is achieved by means of time varying voltages, the maximum temporal change of these signals not being faster than the response speed of the piezo-electric actuators. The incident s-mmw illuminating radiation 1030 is scattered by each scattering element with different phase retardation, resulting in the phase disturbances in the illumination 1040 directed versus the object.

The accuracy of the location of the scattering elements is not important at all. Hence the cost of such systems may be very low.

Figure 20B:
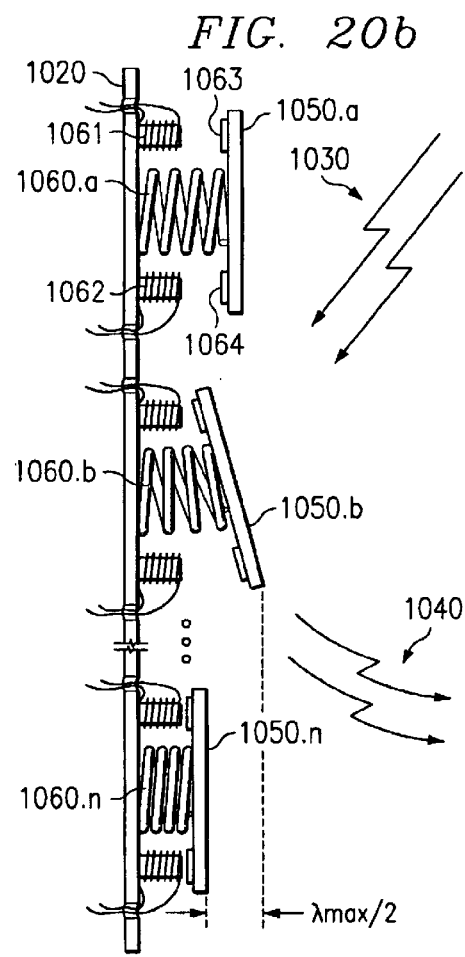

Another possible realization is presented in FIG. 20b. This implementation is a relatively inexpensive variant that can be used for spatially non-coherent imaging goals in s-mmw range. The radiation scattering elements 1050a, 1050b, . . . , 1050n are connected with the substrate 1020 by means of spring connections 1060a, 1060b, . . . , 1060n providing the spatial displacements over required limits.

The scattering elements mechanically attached to the springs can be displaced by means of electromagnetically controllable coils 1061, 1062, . . . actuated by a time varying injection current. When a current is injected, the magnetic material parts 1063, 1064 attached to the backside of the scattering element 1060a, are attracted to the coil elements 1061, 1062. Moreover such replacements may be realized not only parallel to the plane of substrate but also under some angle by actuating the coil belonging to the same scattering element independently. The latter additionally allows changing even the angles of reflection.

FIG. 21 shows another diffuser that is able to destroy the spatial coherence of s-mmw radiation. This embodiment uses a set of transmitting or reflecting cells 1100.a, 1000.b, . . . , 1000.n containing liquid crystal (LC). Low frequency voltage signal sources 1120.i, 1120.j, e.g., being distinct for each cell, are able to drive dielectric properties of the liquid crystal inside the independent cells. The changes in properties will be made in an independent and random manner that causes the independent modulation of the transmitting features over the whole aperture of such composite device for s-mmw radiation. Spatial coherence of s-mmw radiation beam after ones interaction with the diffuser will be destroyed. Possible time and geometrical features of such diffuser are defined by the design of the cells and the kind of liquid crystal that is used. Such diffuser may be used as an effective means for enhanced quality s-mmw imaging.

In the preferred embodiment, the liquid crystal can be modulated between a state of high scattering and high transparency. Two examples are described. Other liquid crystal phases, e.g., those showing the same modulation of scattering behavior, can be applied.

A first preferred mode is the dynamic scattering mode (DSM) in nematic liquid crystals (NLC), the simplest form of liquid crystal structures. These NLC require relatively low resistivity material (e.g., <10 GΩ·cm) and favor negative dielectric anisotropy. The NLC orientation is influenced by ionic current flow and dielectric torque. At a threshold voltage, a striped pattern known as the Williams domains appears. Further increasing the voltage generates the DSM, a turbulent state that scatters light strongly. The DSM is a form of electrohydrodynamic instability. This DSM also appears in smectic-A phase (which features an additional positional order with respect to the orientational order of NLC) and has the advantage that the electrically induced scattering texture is stored when the voltage is removed. Moreover, the scattering texture can be electrically erased with higher frequency voltages on the order of kHz.

Another preferred LC-diffuser embodiment is the polymer-dispersed liquid crystal (PDLC), also known as the guest-host effect. It consists of a distribution of microdroplets in a polymer matrix. The refractive index mismatch between the liquid crystal droplets and the host polymer is the physical mechanism responsible for such light scattering in the voltage-off state. The nematic droplet size, which can be controlled during the polymerization process, can be adjusted to provide a strong scattering effect. An applied electric field orients the nematic droplets such that with suitable conditions the scattering virtually disappears. When the voltage is removed, the nematic relaxes and the droplet orientation becomes random. The resulting refractive index mismatch reasserts the scattering state. A small droplet implies fast viscoelastic relaxation, which is achieved in PDLC without the mechanical problems of a thin nematic cell. Large-area PDLCs (on the order of square meters) can be fabricated with PDLC-technology. Strong scattering in the millimeter wave spectrum requires droplet diameters on the order of millimeters. The mismatch between the polymer and the liquid crystal should be large, implying a high LNC birefringence. The clear state is dependent on closely matching the NLC ordinary index with the polymer matrix over the required temperature range.

One aspect of s-mmw radiation for the illumination of the object under investigation is the diffuse character of the radiation. As discussed above, an array of modulated impedance loaded antennas can produce diffuse scattered light. On top of this the spatial coherence is destroyed. A simple solution for obtaining diffuse multi-frequency radiation is a roughened surface 575 as illustrated in FIG. 22, which can operate in reflection or transmission depending whether the device is coated by a reflective metallic layer or not. Unfortunately, this prior art diffuser is not suitable for diffusing broadband radiation as the surface roughness is interpreted for each frequency differently. Microscopic details, sensed by a large frequency component, are not seen by a small frequency component. Hence the diffuser does not operate efficiently over a broad frequency band.

Figure 23B:
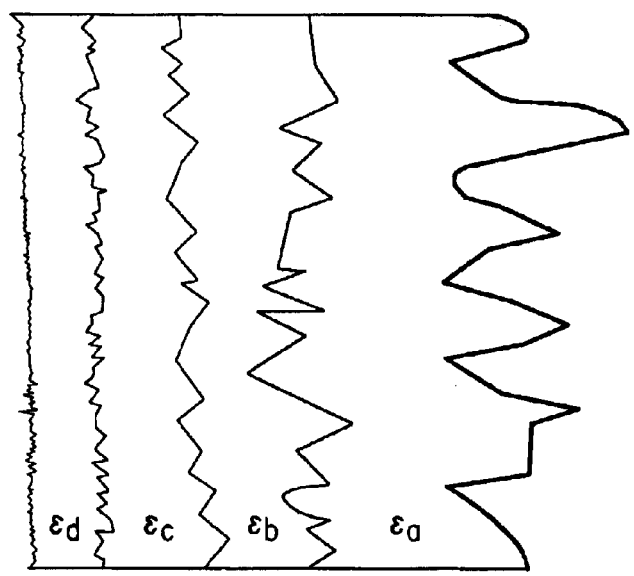

FIG. 23a shows a multi-layer diffuser operating in reflection mode. The backside 300 is a corrugated metallic layer, reflecting broadband s-mmw radiation. The other set of layers 305, 310, 315, 320 preferably comprise transparent materials. Preferably two consecutive layers consist of dielectric materials with sufficient but not too big dielectric differences in order to obtain sufficient radiation traveling through all the layers and sufficient diffusing. In the preferred embodiment, the layers are transparent dielectric materials such as Polycarbonate, polyolefine, polyethylene, polypropylene, rexolyte, a polyester material such as DUROID™, which is commercially available from Rogers Corporation, a polyester film such as MYLAR™, polystyrole, synthetic resinous fluorine-containing polymers such as TEFLON™, a proprietary homogeneous light-permittivity and lossless material such as STYCAST Hi-K™, silicon, germanium, or combinations thereof.

In the preferred embodiment, the size of the roughness should increase from the front side 320 towards the backside 300. In that case, first the largest frequency signals will be immediately diffused on the front layers whereas the smallest frequency signals will transmit through this first layers. As the smaller frequency components of the s-mmw radiation transmit further through the multi-layer structure, the probability that the radiation is scattered becomes greater. The corrugated metal layer 300 accumulates and reflects all the radiation after different levels of scattering, leading to a wide angle and diffuse broad spectral illumination of the object. In essence a multi-layer diffuser operating in reflection mode makes more economical use of the multi-layer structure than one operating in transmission mode (see FIG. 23b) due to the double pass in the reflection operation.

Figure 24:
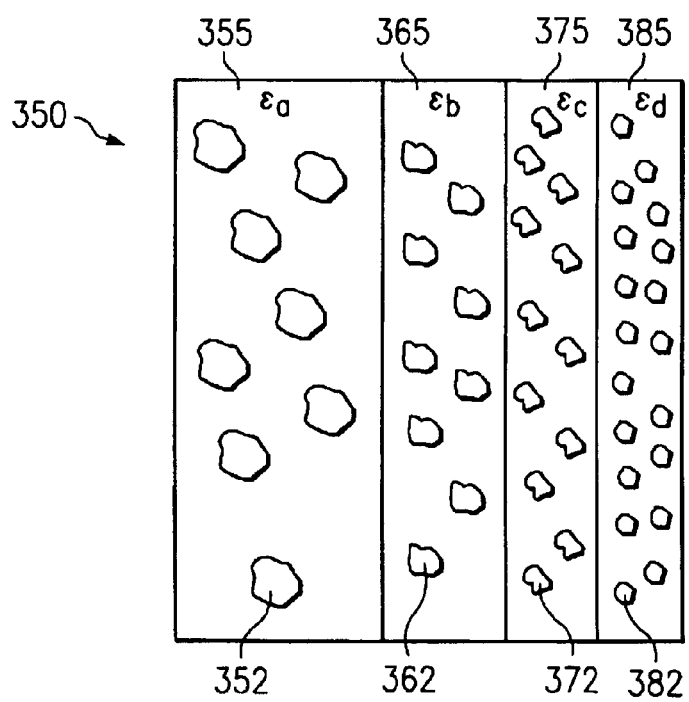
FIG. 24 is a cross-sectional view of a preferred multi-layer diffuser consisting of particle-host configuration with layers of gradual scaling of particle size.

Another implementation of a wide band diffuser is shown in FIG. 24. The multi-layer structure once again includes a reflecting backside mirror 350. The layers on top are heterogeneous layers comprising host materials 355, 365, 375 and 385 and guest materials 352, 362, 372 and 382. As shown in FIG. 24, each guest material is disposed within a respective one of the host materials. The size of the particles 352, 362, 372, 382 at each level is in a well-defined geometrical range in accordance with the frequency band of the wide band radiation. Hence the different frequency bands of the radiation scatter at different levels of the heterogeneous multi-layer. The particle size ranges increase from the front side 385, 382 towards the backside 355, 352. The same diffuser device can be converted in a transmission mode operation by removing the metal layer. Transparent dielectric materials such as polycarbonate, polyolefine, polyethylene, polypropylene, rexolyte, polyester material such as DUROID™, which is commercially available from Rogers Corporation, a polyester film such as MYLAR™, polystyrole, synthetic resinous fluorine-containing polymers such as TEFLON™, a proprietary homogeneous light-permittivity and lossless material such as STYCAST Hi-K™, silicon, germanium, and others are preferably used as the dielectric host material. Combinations of these materials can also be used.

The refractive index of the guest material, the size of the particles are optimized for some wavelength spectrum and for a given host material based on the Mie scattering theory, valid for scattering by particles which are of the same order of magnitude or larger than the wavelength of the s-mmw spectrum considered for optimization. An optimum should be found between the total scattering coefficient and the anisotropy of scattering. The particles should not have a small imaginary refractive index such that absorption remains limited. It is obvious that the different layers 355, . . . , 385 can consist of the same host material. The same can be said from the particle material.

The present invention further contemplates an embodiment, which combines the features illustrated in FIGS. 23 and 24. In this case, both implementations, i.e., a graded surface roughness as well as graded particle size, are combined to further increase the diffuser efficiency.

IV. Coding/Decoding

One of the basic advantages of the proposed approach for contraband detection is in the usage of novel principles of MMW imaging by entirely exploiting the technical capabilities of s-mmw receiving/emitting apparatus for extracting detailed and essential information about the concealed contraband. It is well-known that the scattering properties of any object essentially depends on angle of incidence of the radiation with respect to the object surface, radiation polarization state, the carrier frequency and other physical radiation features. It is advisable and preferable to be able to collect at the receiver side great available volume of multi-parameter scattering data derived from the interaction of the s-mmw radiation with the surface and internal structure of the contraband. The preferred embodiment of the invention allows primarily decomposing the object illuminating radiation over multiple radiation components exhibiting different physical radiation features, which are, at least, not the same for distinct said radiation components and analyzing the multi-parameter dependent scattering data at the receiver side.

In certain embodiments of the present invention, the ability to encode information about the composed radiation and its constituent partial components (or simply partials) provides an advantage. The encoding can take place either at the source 12 (FIG. 2), e.g., where the information on carrier frequency or/and polarization of the source emitted radiation may be encoded or at the diffuser 14, e.g., where information on angles of propagation of radiation component may be independently encoded or both for complementary encoding. The encoded information is typically decoded at processor 20.

In one aspect, the present invention provides generating radiation that includes multiple phase-independent partial components exhibiting distinguishable physical features. As examples, these features may include the angles of partial components' propagation(which is equivalent with the angle of incidence of the partial component on the surface of observable object), radiation carrier central frequency, or its polarization. As was discussed, each of these features provides information about the object being irradiated and this information can be used to enhance the visual quality of the object and/or to recognize one correctly.

The radiation is encoded to label different ones of the multiple partial components. This labelling, for example, can be accomplished by modulating each of the partial components differently or by implementing doublet spectral lines with a labelled frequency shift, as will be discussed in a preferred embodiment below. After the radiation is reflected and scattered from the object being imaged, the radiation can be detected and converted into electrical signals. The information relating to features of the multiple partial components can then be extracted from the electrical signals after decoding. The decoded electrical signals can further be converted into a set of so-called partial images. Each partial image is responsible for a particular combination of physical features of the radiation.

As a first example, it is possible to encode the angles of incidence of the radiation components on the surface of observable object. Referring to FIG. 16, in the preferred embodiment, the diffuser 14 is a spatially extended two-dimensional array of scattering elements whereby each distinct diffuser element has a particular angular position relative to the surface of the object 16. FIG. 16 shows different angles of incidence 73, 74, 75 between scattered rays 63, 64, 65 of three different diffuser elements 14a, 14b and 14c of array 14 and a point 16a on object 16.

Accordingly, one can assign to each diffuser element 14n or cluster of closely spaced diffuser elements a distinguishable modulation frequency characteristic. In the limit, each antenna coupled diffuser element-would have its own distinguishable modulation frequency, although this feature would tend to be overkill. The size and spread of the clusters can be dynamically adapted in order to achieve dynamically enhanced image quality or zooming functions. In this example of angle encoding where each diffuser element or cluster of elements has its own modulation characteristic, a twofold advantage appears, namely, simultaneous destruction of spatial coherence and the encoding of different angles of incidence.

When the spectrum of the radiation being multiply decomposed and further scattered by observable object, can be resolved by the receiving apparatus of the imaging system, the radiation components scattered by distinct areas of the diffuser can be distinctly identified in each pixel of the received image. That allows practically checking a whole set of information about the object and/or person under investigation. Each other physical feature of radiation is first scattered by the diffuser array and then by the observable object. In this manner, various characteristic polarization states, incident/propagation angles or carrier frequency information can be coded in distinct shifted spectral lines.

Hence, due to the technique of individual encoding (e.g., modulating) of such radiation components, multiple partial images of concealed objects, whereby every image is generated by the particular radiation component, may be acquired independently from each other by receiving apparatus of the imaging system. These partial images can then be sent to memory of digital processing means for following processing (individual and/or cooperative). Hereby all multiple partial images may be obtained in parallel and in real time.

The proposed approach provides a lot of novel possibilities in s-mmw imaging techniques and further image processing that will be discussed below. For example, the proposed s-mmw imaging techniques provide a method to widely and adaptively change the properties of object illuminating radiation both during the time of imaging procedure (adaptive synthesized illumination) and even after the imaging (adaptive image post-processing).

The latter is achievable due to the generation of an extended set of partial images with distinct physical features during the illumination process. Each such partial image may exhibit a speckle structure and, as a result, bad visual quality. But the result of summing such multiple images, as discussed above, exhibits enhanced visual quality image with essentially reduced speckle structure. These summing procedures (or, more precisely, weighted accumulations) may be performed by a processor by digital methods if received signals responsible for distinct partial images are sampled and stored in digital memory.

Because any weighted combination of partial images may be constructed, any kind of image may be artificially synthesized. For example, if only such partial images are summed, which are generated by radiation components exhibiting all the same physical features except only one, then the resultant weighted sum image will show enhanced visual quality and simultaneously will be the image being produced by the radiation with some distinctly defined radiation features. The latter can be important because such enhanced visual quality image might separately disclose distinct peculiarities of concealed objects (e.g., weapons, mines, or others) that extremely increase the probability of its true recognition.

Figure 25A:
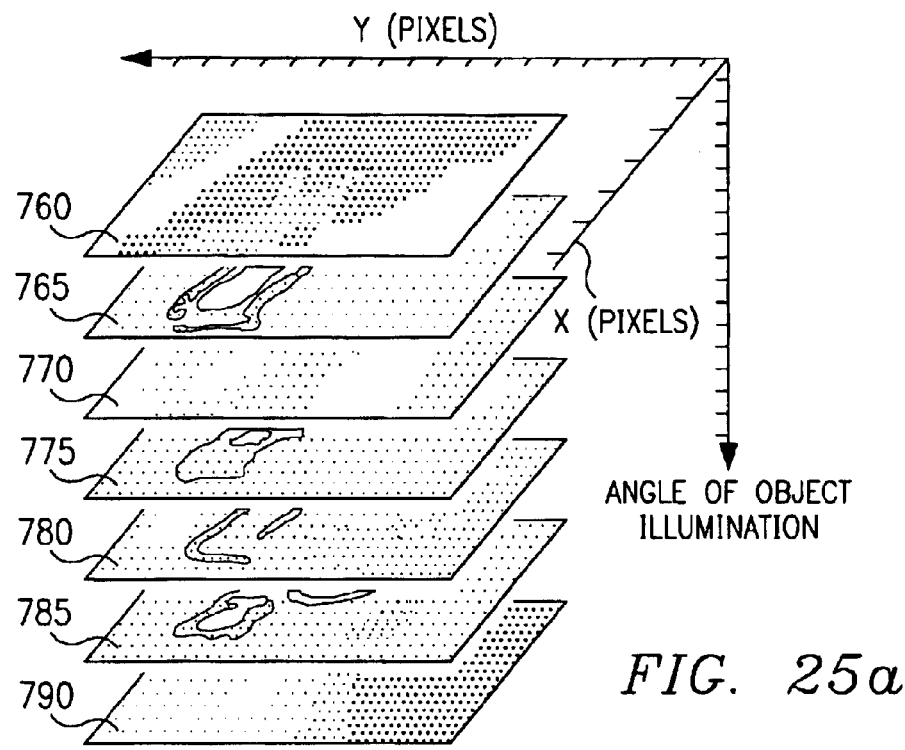
FIGS. 25a–25b show the principle of angular decomposed imaging obtained for narrow-band linearly polarized illumination of concealed object.
Figure 25B:
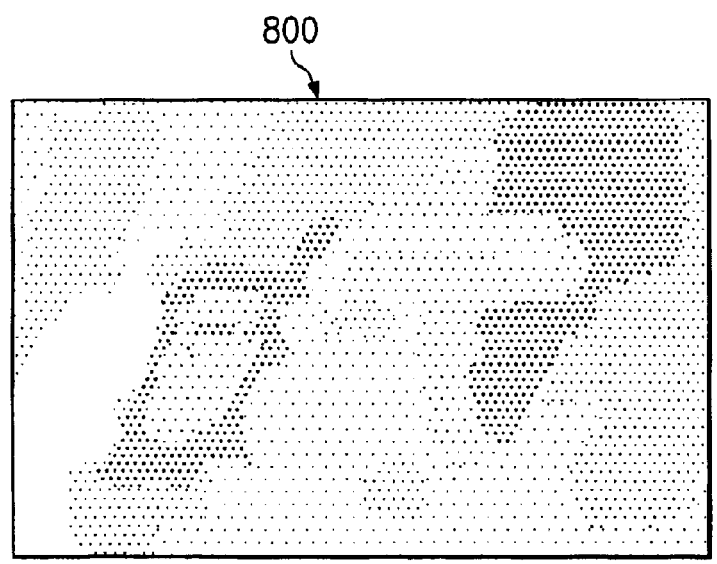

For example, as illustrated in FIG. 25a, if the diffuser is illuminated only by narrow spectral band linearly polarized radiation, then partial images 760, 765, . . . 790 may be produced by radiation components exhibiting the same radiation carrier frequency and polarization state but exhibiting different angles of incidence with respect to the surface of observable object. In this case, the summed image 800 of the partial images 760, . . . , 790 will be physically equivalent to the image produced by monochromatic linearly polarized radiation, which is spatially non-coherent near the surface of the object. It is common knowledge that such spatially non-coherent image 800 will show enhanced visual quality with substantially reduced speckle structure. At the same time it will be a precisely defined polarized one-frequency image comprising the object information (object imaging details), which may be only visible on considered image exhibiting said specific polarization and carrier frequency.

Figure 26:
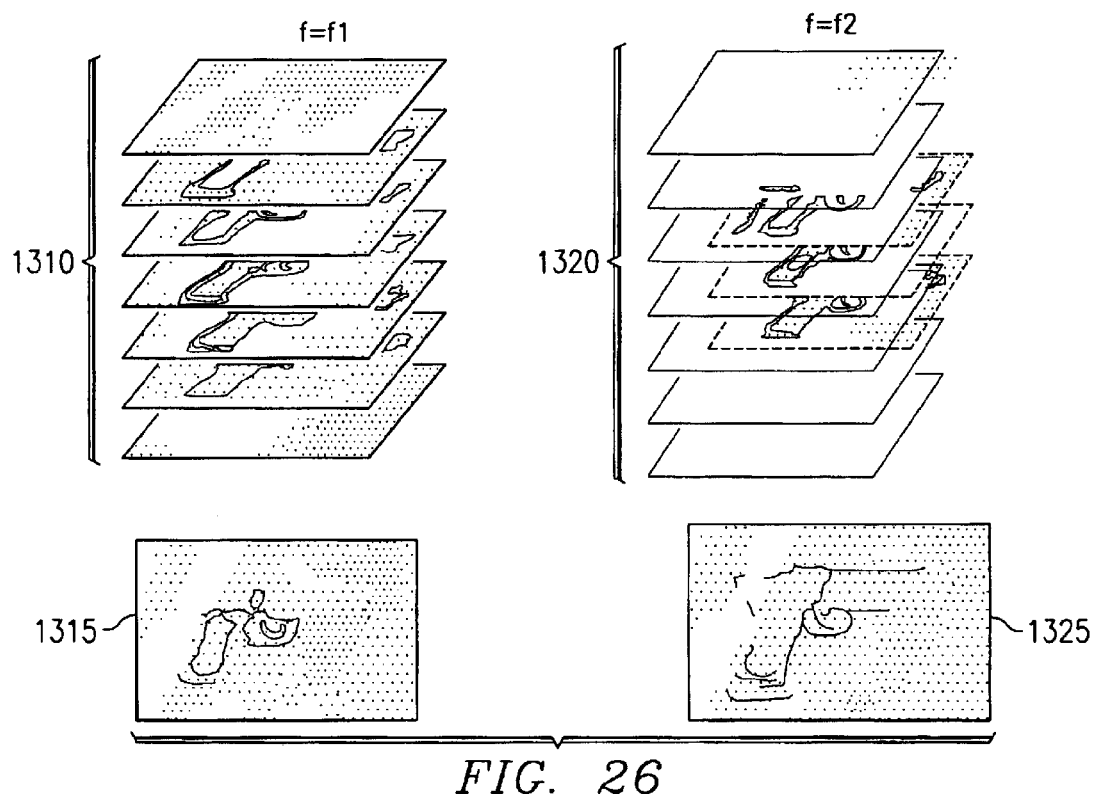
FIG. 26 shows schematically the principle of angular decomposed imaging obtained for multi-frequency illumination of concealed object.

If the diffuser is illuminated by radiation exhibiting another carrier frequency, then another non-coherent precisely defined one-frequency image 1325 (see FIG. 26) will be synthesized based on the stack 1310 of angular decomposed images for this carrier frequency or/and polarization state of the radiation. The synthesized image 1325 at this frequency may reveal another intrinsic set of object image details than the image 1315 synthesized from the stack 1310 on angular decomposed images. Because the diffuser may be illuminated with multi-frequency radiation, whereby every one-frequency component is individually encoded (e.g., modulated), then the correspondent one-frequency images may be individually selected by processing means just by choosing the correspondent partial images 1320 from the whole set of such images being received simultaneously.

If the partial images may be combined in one or another way, then other kind of images will be artificially synthesized. For example, if summed images comprises partial images, generated by radiation components exhibiting distinct carrier frequencies but scattered by the same diffuser element, then these resultant sum images will be equivalent to the multi-frequency image of the object illuminated from one spatial localization of said diffuser element. By choosing other "virtual" points of the diffuser array, scattering the multi-frequency illumination, similar one scattering-point multi-frequency images may be synthesized. Finally if all partial images will be summed the resultant image will be physically equivalent to the image of the object being illuminated by "white light", i.e. the radiation which is temporally and spatially totally non-coherent. Such image will exhibit excellent visual quality and absence of any speckle structure.

Some specific details of the imaging based on the principle of decomposition of object illuminating radiation are schematically shown in FIGS. 27a–27d. These figures are intended to show the mechanism of angular decomposition of narrow-band primarily coherent radiation. These illustrations may be easily extended to the case of multi-frequency and multi-polarization radiation.

Figure 27A:
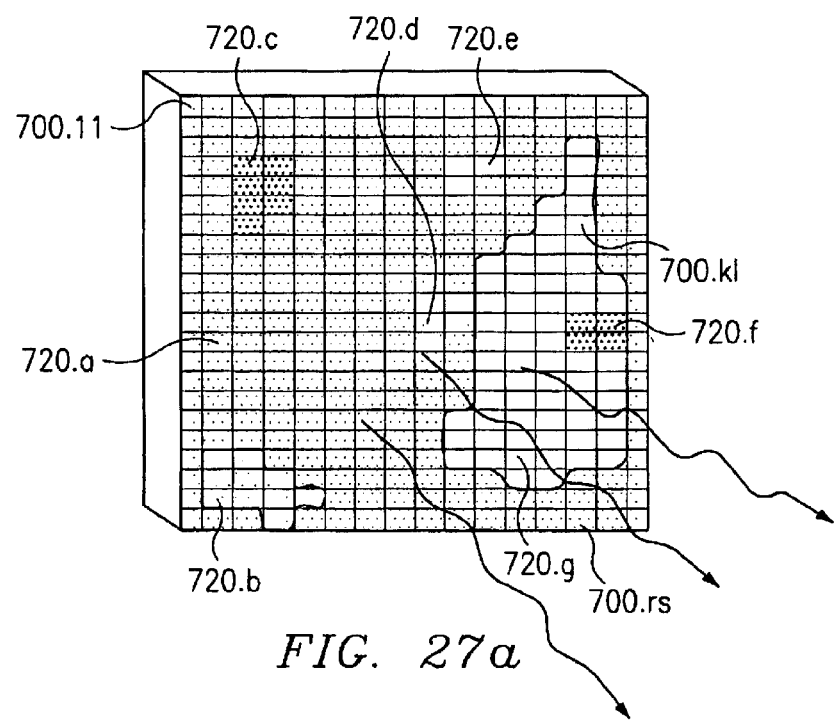
FIGS. 27a–27d show angular encoding by means of electronically controlled diffuser.
Figure 27B:
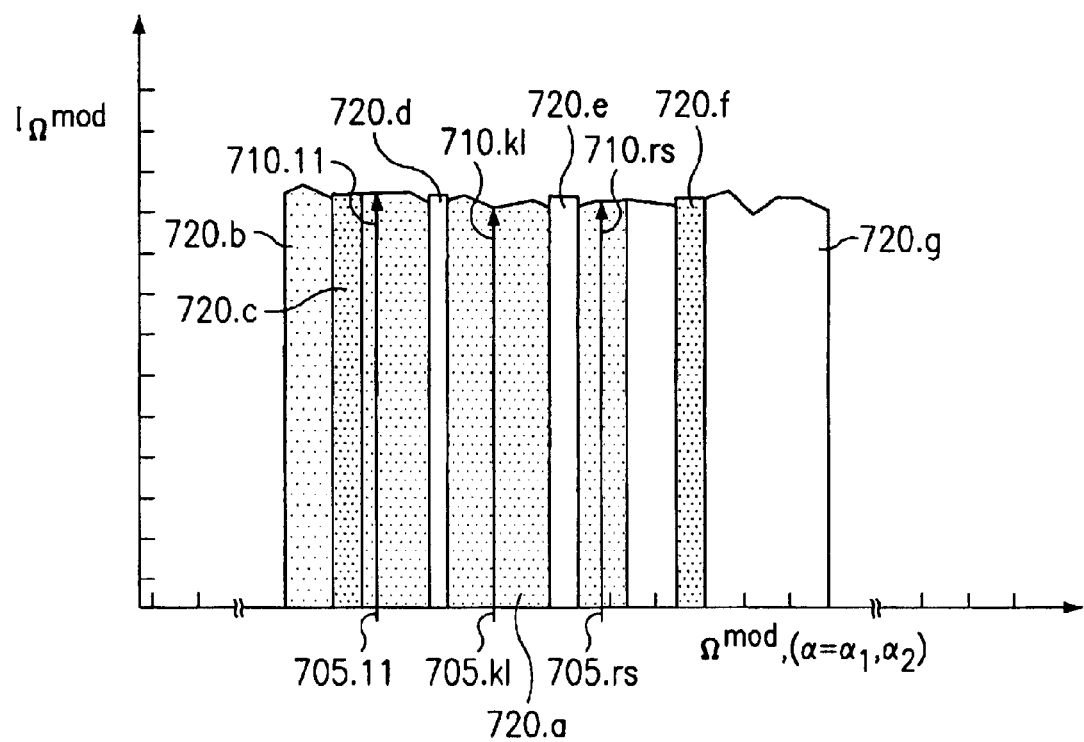

Coherent linearly polarized radiation source 12 (FIG. 2) is used here for homogeneously illuminating the electronically controlled diffuser 14. Independent scattering elements of the diffuser decompose the coherent radiation, being incident on them, over independent radiation components. Because the scattering diffuser elements 700.11, . . . , 700.kl, . . . , 700.rs have distinct spatial localization relative to illuminated object, correspondent partial radiation components will exhibit distinct angles of incidence with respect to surface of the object. When scattering properties of distinct diffuser elements are modulated with different frequencies 705.11, . . . 705.kl, . . . , 705.rs, then the carrier frequencies of scattered components will have distinct AM frequency sidebands being precisely and individually shifted relatively to primary carrier frequency of the incident radiation, as illustrated in FIG. 27b.

Figure 27C:
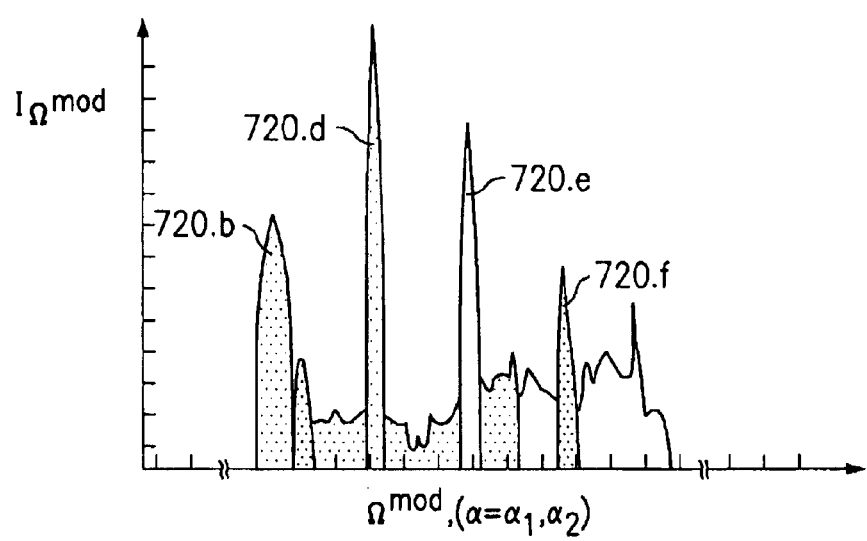
Figure 27D:
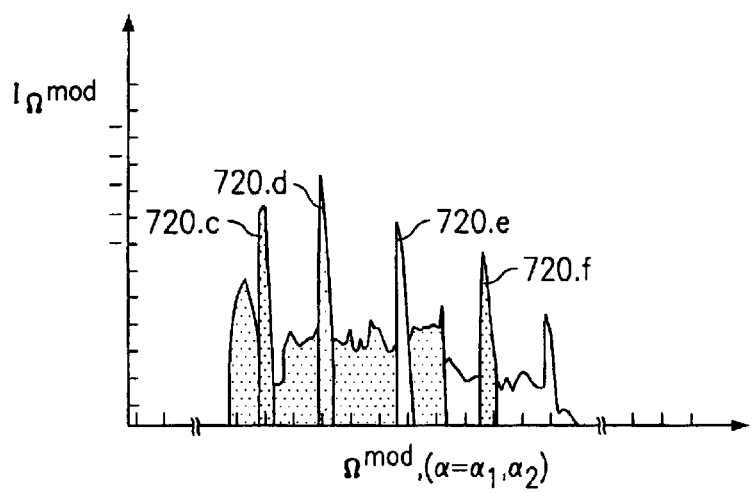
Figure 28A:
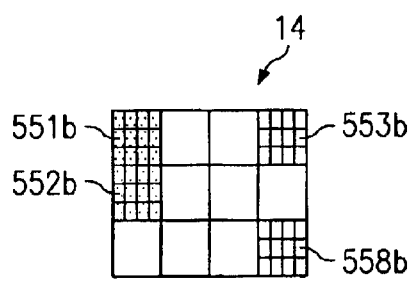
FIGS. 28a–28b shows schematically the principle of clustering the diffuser elements in modulation frequency intervals.
Figure 28B:
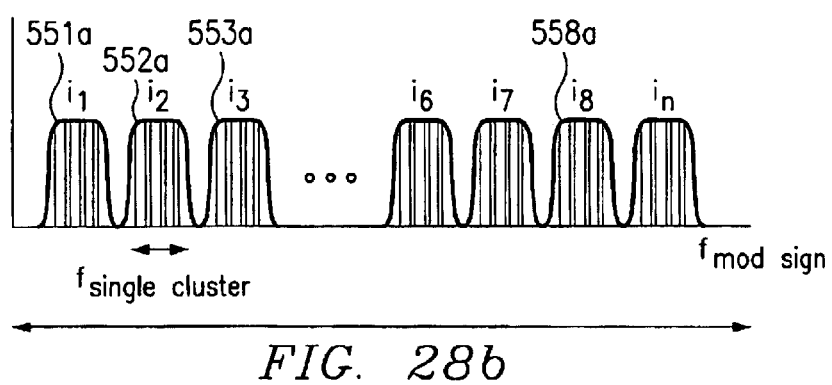

The diffuser is designed in such a way that the wave-front amplitudes 710.11, . . . , 710.kl, . . . , 710.rs of the generated-components of angularly decomposed radiation are equal to each other within the observable area. Correspondent spectral composition (only for one AM side) of the object illuminating radiation being decomposed over the incidence angles is presented in FIG. 27b. Here, every spectral component is the component of the angular-decomposed radiation which illuminates the object from particular diffuser point (e.g., the point-like scatterer), which may be strictly labeled by correspondent modulation frequency. The areas of spectral localization of the components at spectral plots 27b, and areas of space localizations of the correspondent scattering elements at plane of the diffuser which are responsible for generating the components are shown by the same grey-scale levels 720a, . . . , 720g for better illustration. After interaction of the modulated radiation with the object, the total spectrum of modulation signals is retrieved at each pixel, as illustrated in FIG. 27c. At some frequency components, 720b, 720d, 720e, 720f the amplitudes of the scattered radiation are extremely peaking with respect to the average of the other spectral components, indicating the possibility of glint effect induced by the corresponding radiation scattered by some set of scattering elements of the diffuser array. The same spectral information can be retrieved in the signals averaged over all the elements of the diffuser array. The peaks in the spectral regions 720c, 720d, 720e, 720f possible refer to strongly reflected parts induced by the some set of the scattering elements of the diffuser array after interaction with metallic parts of the object When the principle of ordering the diffuser elements in some set of cluster elements is used, the number of the distinct angular partial images may be effectively reduced. This principle is illustrated in FIG. 28. A group of scattering elements 551b, . . . , 558.b belonging to the same frequency interval $f_{i,n}$ 551a, . . . , 558.b are shown. The spectral composition of different frequency intervals 551b–558b is indicated on the diffuser array 14.

It is preferred that the scattering elements belonging to the same frequency interval 551b–558b are geometrically clustered (e.g., closely located elements) on the array such that the angular information content of the radiation scattered by each cluster is more or less precisely defined. Naturally the elements being relatively distant will belong to distant clusters. The accuracy of the angle information depends on the number of scattering elements belonging to the cluster. A good spatial organization of the frequency clusters enables the association of a different averaged angle of the propagation (or equivalently an angle of incidence relative to the object's surface) with each frequency cluster.

Figure 29:
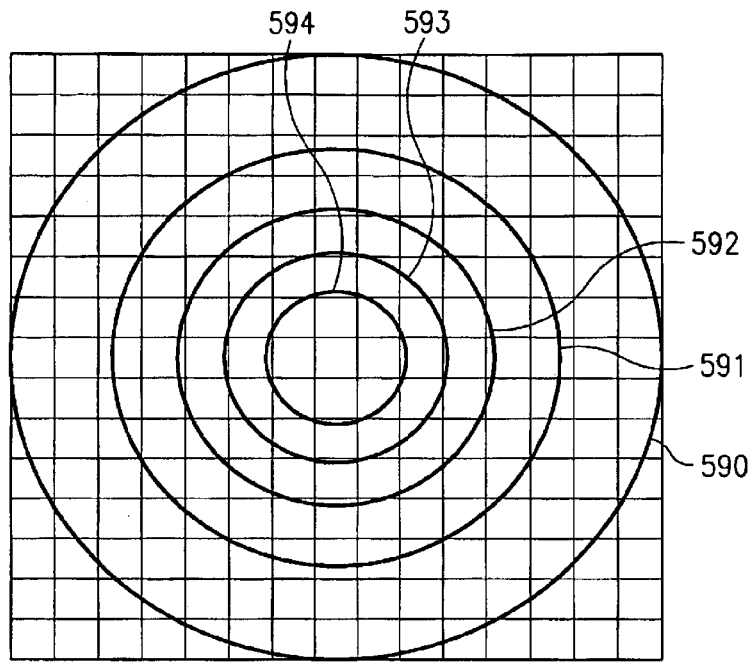
FIG. 29 shows schematically the principle of concentric clustering of the diffuser elements in modulation frequency intervals.

Another preferred configuration for the clustering of the diffuser elements in distinct spectral intervals is shown in FIG. 29. This configuration is of the concentric type. In this example, all diffuser element belonging to the same area between two concentric circles 590, . . . , 594 are grouped to define a certain angle.

The frequency selection at the receiver side is conceived such that all of the frequency signals belonging to the same frequency interval are processed as one signal. In this manner different partial images are produced for the different frequency clusters, e.g., for the different angles of incidence. The degree of spatial coherence of radiation produced by each frequency cluster depends on the sizes of the cluster and may be high enough if the sizes of cluster are not large.

However, the number of angle codes (e.g., the number of frequency clusters) and the spatial coherence level (e.g., the spatial extension of the cluster) can be dynamically adapted for current detection task on the basis of a real-time adaptive analysis of information content of the produced partial images. Thereby, the whole set of such dynamically generated partial images will yield high visual quality after weighting such image. This feature is useful for s-mmw imaging since the type of reflection (e.g., specular or diffuse) of the radiation by an object surface depends on the angles of radiation incidence. Since the different angles of incidence can be individually and/or jointly analyzed in real time, the angular orientation of the surface parts of the objects yielding specular reflection can be easily determined.

Summing (or accumulating) multiple partial images formed by the radiation components being independently scattered by diffuser elements will lead to synthesis of an image that is physically equivalent to an image formed by quasi-monochromatic (narrow-band) radiation with reduced spatial coherence. Therefore, if the sizes of the diffuser are large enough and the whole set of partial images generated by the diffuser are summed, then equivalent radiation can be considered as spatially totally non-coherent. If only part of the images from the whole set of them will be summed, the radiation will be only partially non-coherent (with finite radius of spatial coherence) with some speckle structure being reduced. The latter images may be interesting for the goals of specific image processing because the equivalent radiation may be synthesized as being propagated from finite solid angle and, as a result, may have some particular averaged angle of incidence of such radiation on the object surface. Thereby the correspondent image will have enhanced quality.

Different points of an object's surface (or/and internal structure) will reflect the radiation components, which have different angles of incidence on the object surface, by different manner and this fact can be precisely checked by the receiving apparatus of the proposed imaging system. In effect each sensitive element of the receiving array "looks" at only one particular point of object surface so that every such element will receive the radiation components reflected only by the particular point which can be distinctly processed. Now any relative changes in amplitudes of the radiation components which are reflected by particular point, will be strictly defined by scattering properties of object surface at the point.

For example, some radiation components may have strong specular reflections from the surface point (due to mirror-like reflection at particular angles of incidence—so called glint effect) and therefore exhibit extremely strong signals at output of the correspondent receiving array element. In the proposed imaging system, the disturbing signals that are responsible for the radiation components may be simply extracted or decreased at the stage of signal processing (or decoding) procedure since they have distinct frequency localization. Other components at the same pixels or in other pixels may have diffuse scattering and may not be subjected to any further processing. The possibility of selective extraction of disturbing signals without any influence on other information signals of the image is a basic feature of the novel s-mmw imaging approach which creates new realities for image processing.

So the approach allows, from one side, to effectively delete the disturbing signals caused by strong specular reflection in each weighted sum image, from another side, to exploit such signals for determination a current space orientation of the object relative to imaging system and for defining and predicting the trajectory of the object.

Figure 30:
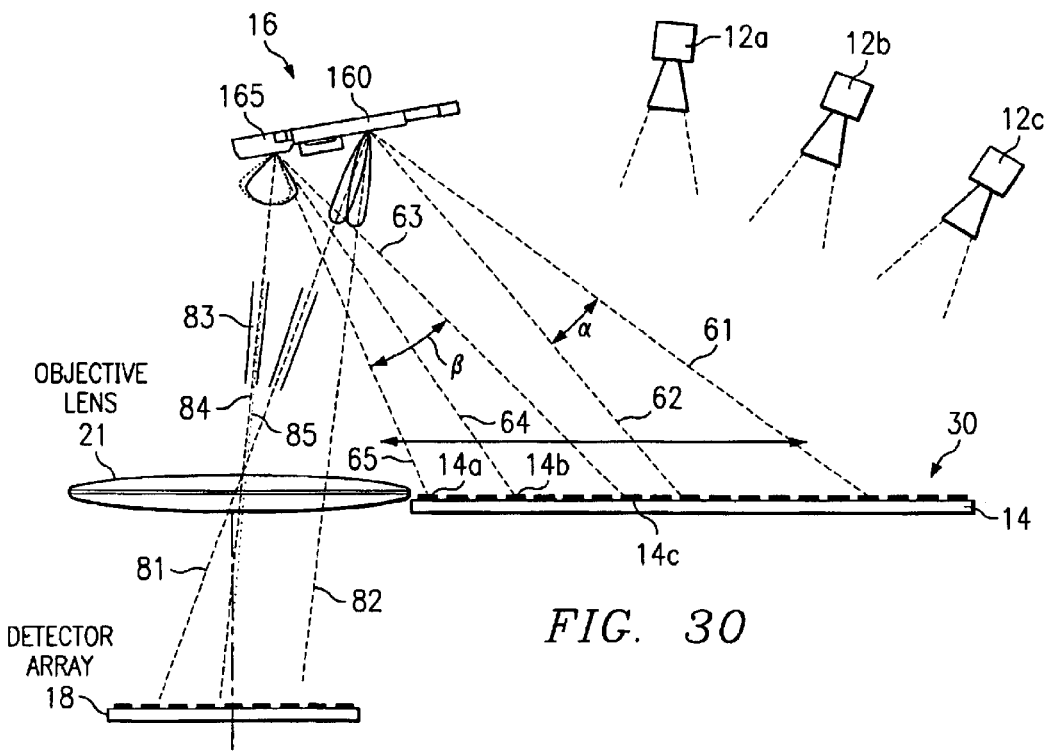
FIG. 30 schematically illustrates the different kind of scattering of the illuminating radiation on the concealed object surface.

This concept will be discussed in further detail with reference to FIG. 30. FIG. 30 is similar to FIG. 2 in that it includes AM s-mmw radiation source 12 and directs radiation toward diffuser 14. In this case, source 12 is formed from three separate sources 12a–12c. Radiation from diffuser 14 is directed to object 16 where, after being focused by lens 21, it is received at detector array 18.

Mirror-like subparts of the object 16-can degrade the total image quality by producing bright, localized spots in the image. This is known as the glint effect. Such excessive brightness can easily cover details of the object 16. As shown in FIG. 30, rays 61 and 62 impinge upon a specular reflection region 160 and are converted into rays 81 and 82, which produce bright spots on the receiver array 18. The scattered rays 63, 64 and 65 impinge upon a diffuse region 165 of the object 16 and are converted into much less intensive rays 83, 84, 85. When these rays reach the detector array 18, they are not observed due to the dominating field intensity produced by rays 81 and 82. Such glint effect due to the geometrical characteristics of the object 16 can be eliminated when scattering element 14a is properly clustered in a set of modulation frequencies for encoding of angular information. This technique provides the possible decomposition of the signal of every pixel of a received image over partial signals being responsible for correspondent partial images, produced by different radiation component exhibiting distinct angle of component propagation each of which is simultaneously recorded at different angles of incidence.

Further, by adding a frequency selection circuit (not shown), which is able to select different spectral components of the decomposed radiation, the control over any resultant image may be provided by effectively processing multiple images and signals within any pixels of such images. Any strong signals exhibiting some disturbing effect may be distinctly deleted or reduced in according with criteria of applied processing algorithm. It may be down for every pixel of every partial image due to employed modulation technique.

Figure 31:
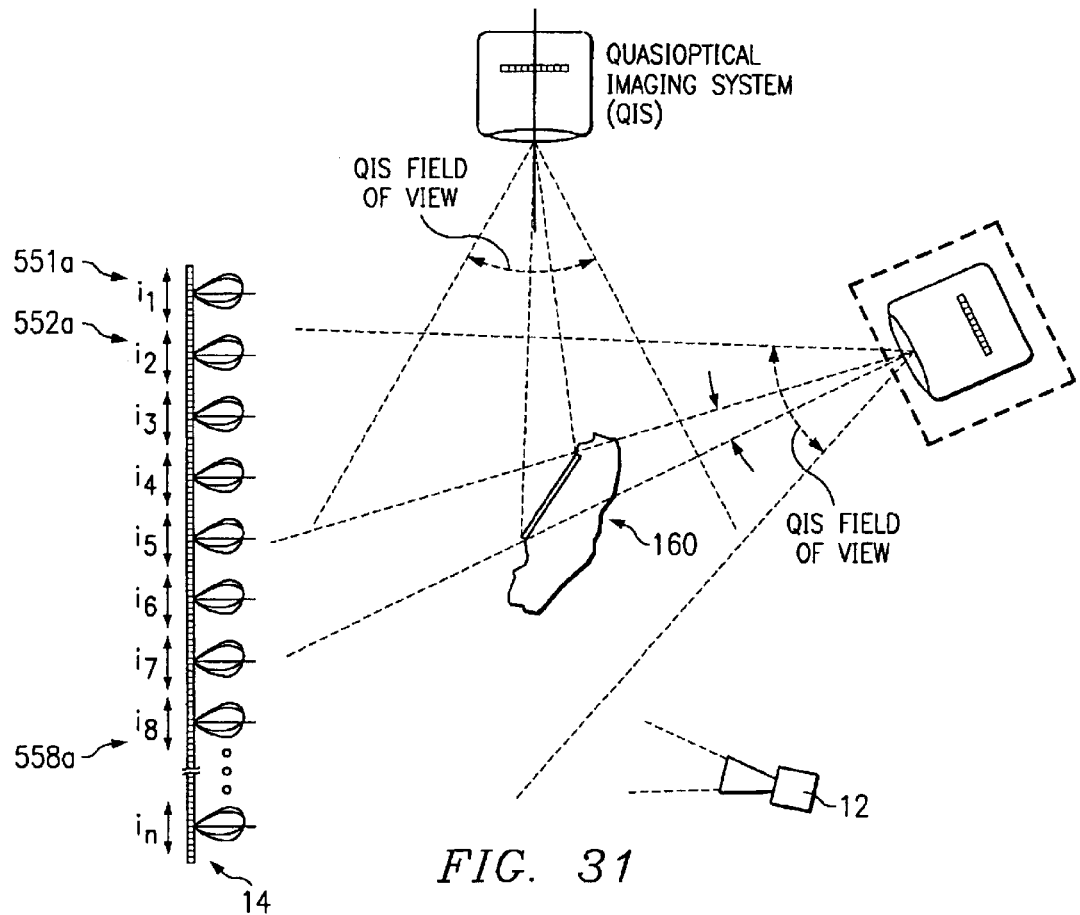
FIG. 31 shows the imaging set-up featuring angular encoding by means of the diffuser array.
Figure 32:
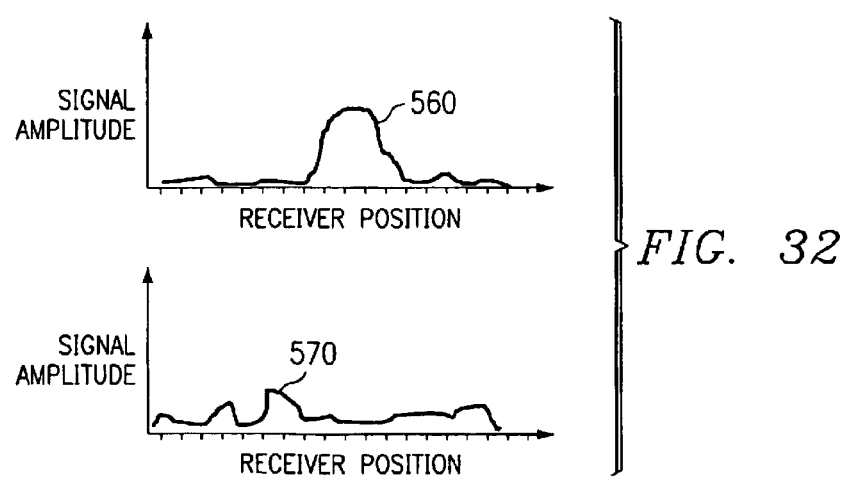
FIG. 32 illustrates the difference between mirror-like and diffuse image signals along a linear subarray of the detector array.

When the localization of the different modulation frequency characteristics is stored in computer memory, one can deduce the geometrical characteristics of the object and its orientation. When some specific modulating frequency interval(s) are well localized and produce highly peaked signals in the detector array, one can deduce for example that the scattering elements of the frequency clusters 555a–557a (see FIG. 31) are located such that their corresponding radiation was predominantly scattered on a mirror-like surface 160 of the object 16. A typical detector signal for that case is represented by curve 560 in FIG. 32. Signals from the frequency clusters 551a–554a, 558a–559a, however, is reflected on diffuse parts of the object and results in broadly spread detector signals illustrated by curve 570 of FIG. 32. This modulation technique allows the reduction of any influence of disturbing signals on the quality of resultant image by means of aposteriory image processing.

Figure 33:
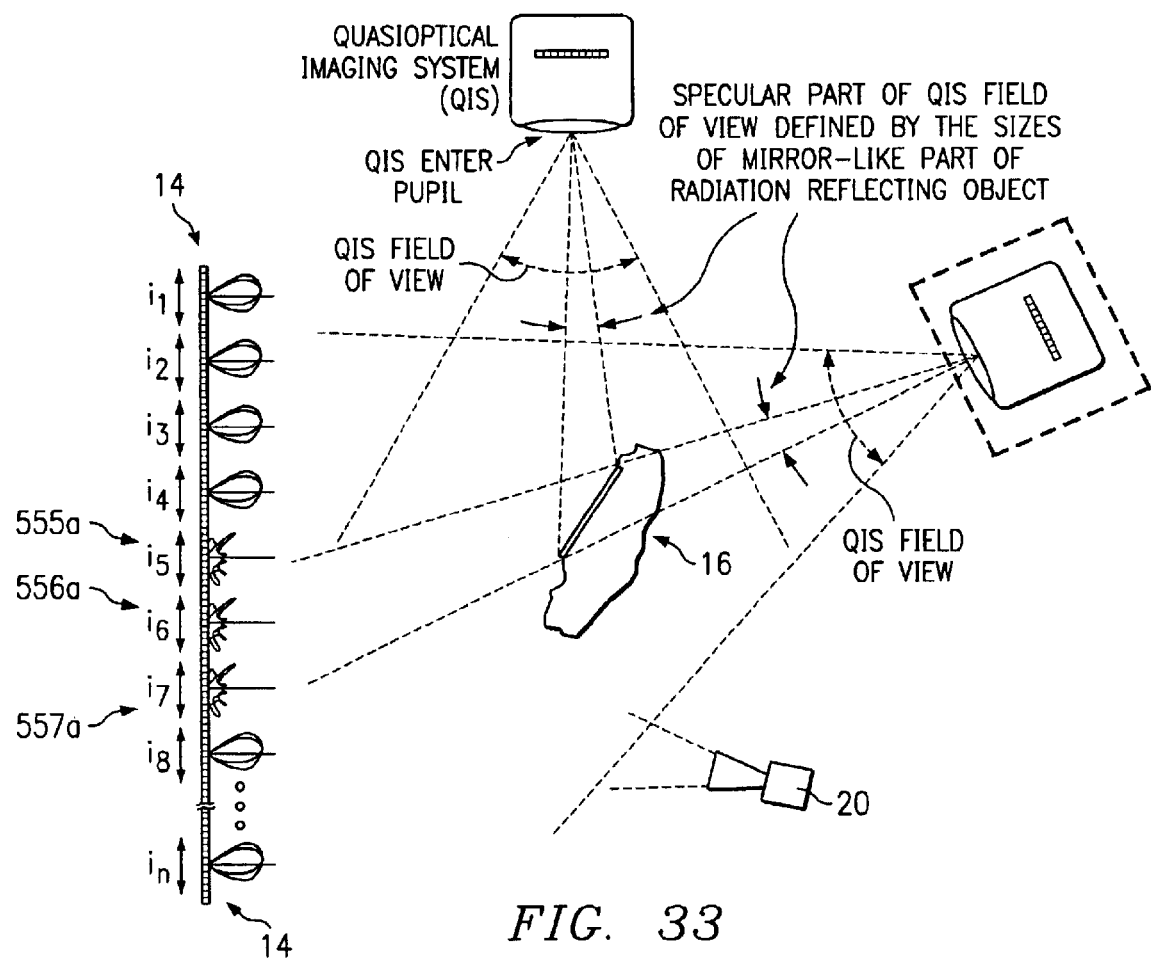
FIG. 33 shows the imaging set-up featuring angular encoding by means of the diffuser array.

The glint effect can be eliminated not only by the use of processing procedures but also by feeding information back to the radiation source (source 12 and/or diffuser 14). In this method, the glint effect can be reduced when the impedance loaded antennas belonging to the frequency intervals associated with mirror-like reflections of the object are brought into a mismatched state by applying the appropriate bias to the elements such that highly diffuse reflected radiation is produced by these elements of the diffuser array. An example of this result is indicated in FIG. 33.

In the case where the diffuser 14 is based on vibrating elements for eliminating specular reflection, the elements creating strong specular signals may be automatically oriented for the time of a particular imaging by such manner that radiation scattered by them will propagate past an observable object or, at least, will not enter the pupil of the imaging system. For a majority of diffusers of another type some, analog approaches of real-time eliminating of the glint effect may be effectively exploit as well.

So in any case there appear possibilities to know an orientation of the object relative to the enter pupil of the imaging system, check and predict a possible dynamics of the object or human carrier of the object. This fact can be very important because it allows the system to confirm or deny, any hypothesis about peculiarities of the object at the various stages (in a time and in a space) of its dynamics.

The latter is useful when the dynamics of the object are of concern and more or less predictable. The approximate trajectory of any object in the field of view may be known or defined artificially, for example, by organizing a predefined trajectory of person's movement in the observed area. Since the suspicious object on the body of human carrier is not generally movable relative to the body, the possible appearance of the partial images may be predictable with high probability. If this hypothesis is confirmed in majority steps of trajectories, the hypothesis can be defined as true. This addition detection possibility is able to sufficiently decrease the level of false alarms in contraband detection.

Additionally, it should be noted that scattering properties of the diffuser elements typically define the operation capabilities of the illumination system and the imaging system in general. The proposed approach to realize a diffuser allows flexible adaptation of the features of the diffuser to the application task. Scattering properties of the diffuser strongly depend on basic antenna type of scattering element the properties of which may be widely adapted (including operation frequency band, antenna pattern, polarisation sensitivity and so on). Moreover the whole diffuser array may consist of some sub-array exhibiting distinct scattering features that may be urgently useful for some applications.

In an alternate embodiment, the s-mmw source radiation incident on the scattering array is frequency modulation modulated. This modification allows realization of larger frequency shifts for distinct partial components with respect to the AM (amplitude modulation) features introduced by the scattering array. By introducing FM (frequency modulation) techniques, additional features of the objects can be analyzed by further spectrally decomposing the illuminating radiation over other radiation attributes and essentially increasing the volume of physically independent information attributes about the object under investigation. Moreover FM techniques may exhibit enhanced signal to noise ratio of detector/receiving apparatus compared with AM modulation only.

Figure 34:
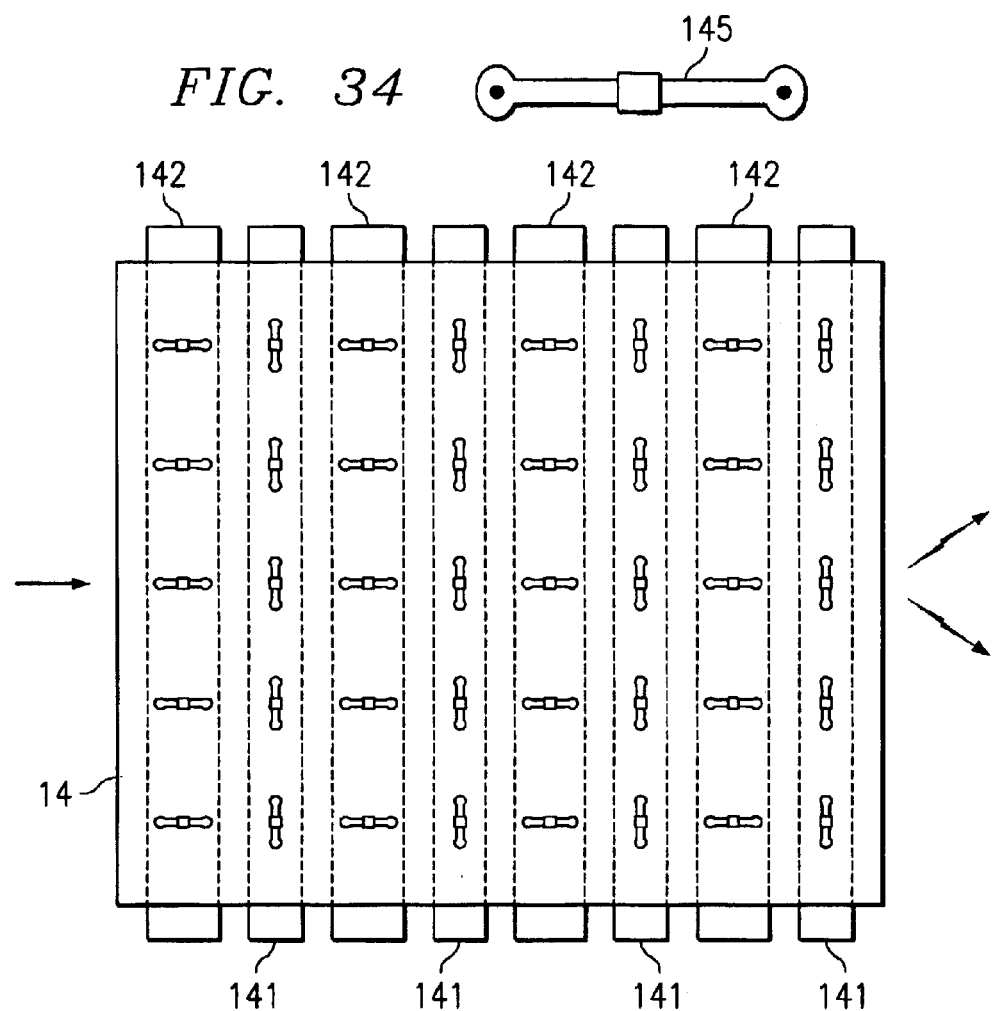
FIG. 34 is a top view of a coherence destroying diffuser array comprising sub-arrays featuring distinct polarization sensitive antenna elements.

Referring to FIG. 34, a realization of this kind of diffuser is shown. The diffuser 14 comprises two sub-arrays 141, 142 having complementary polarization features. In this example, the two sub-arrays are interleaved columns of resonance dipole antennas 145. Such an array may additionally create two independent non-coherent beams with orthogonal polarization features if the elements of the sub-array are spectrally clustered by distinct manner and radiation beam that is incident on the diffuser exhibits linear radiation. Informative high quality synthesized images can be created by means of (or y) weighted digital aggregation of multiple partial images. Alternatively, these images can be created partly by analog and partly by digital techniques. Properly weighting of partial images having statistically distinct speckle distributions may eliminate coherent noises of imaging system. Therefore only those partial images will be aggregated which have the same set of radiation physical features (or within some range of changes of some features from such set) being of interest for the goal of imaging observation (for example such set may include particular polarization state, particular carrier frequency and angle of radiation incident on surface of observable object which can change within some range).

Aspects of the proposed imaging technique inherently exhibit novel possibilities for enhancing image visual quality for different physical properties of illuminating radiation by means of image processing. Because all partial images can be individually accessible, those partial images that will create obvious destruction of the resultant sum image can be simply extracted from the correspondent set of summed partial images. For example, such destructive partial images may be generated by the radiation fields being specularly reflected from flat surface parts of observable object (result of appearance of so called glint or glare effect) and the partial images may be excluded from the resultant set.

Moreover, only in those particular pixels of the image which are really destroyed by the glint effect, only the signal components being responsible for the said glint effect may be selectively deleted (or essentially reduced). Such principally novel possibilities of image processing make the imaging technique very attractive for different application including, of course, contraband detection.

The procedure of such aggregation is an interactive one and should continue up to the moment when a level of noisy coherent speckles and other factors disturbing a quality of the resultant image will be decreased to a desired level. Such an enhancement procedure may be realized for revealing important details of the concealed objects.

In the proposed imaging system, the procedure enhancing an image quality may be performed both in time of illumination or even after the illumination only on the basis of manipulating by the partial images previously stored in memory of the processing means. The number of distinct radiation components and the law of radiation decomposition will be defined by current needs of contraband detection procedure and may be changeable electronically in real time (e.g., from 2–3 up to 1000 components and even much more). Sometimes reducing the number of the generated partial images only to a value being only enough for current application goals is important. It allows the simplification of the receiving apparatus, increase the processing and imaging rate and employ the processing means with usual hardware possibilities.

Generally the proposed imaging approach allows the artificially changing of spatial and temporal coherence of synthesized radiation, its polarization state, angles of preferable illumination and even geometry of illumination of "virtual" s-mmw source. As it was mentioned due to the fact of primarily decomposing the illuminating radiation over multiple multi-parameter radiation components, which can be distinctly received and recorded, any resultant images may be obtained by means of summing (or weighted overlapping) of multiple partial images which are formed by said radiation components independently from each other. Moreover, this multi-parameter partial image summing may be repeated for different positions of the moving person/object in accordance with the trajectory of each of them relative to the imaging system enter pupil in the whole observed space. The information steadily gathered during the trajectory allows controlling the image visual quality in a unique and very effective way, increasing drastically the level of true recognition (and detecting) of the observed objects.

The optimal multi-features composition of object's probing radiation may be adaptively generated depending on the specific application. For the detection and imaging of specific objects concealed (under specific conditions), experimental training sessions can be organized to determine the scattering properties of the specific objects and derive the optimal imaging procedure (e.g., optimal combination of illumination parameters, optimal value of spatial and temporal coherence). These specific imaging procedures can be stored in computer memory and launched in the case of particular a priori known concealed objects.

When a more universal imaging system is envisioned, e.g., when a plurality of a priori unknown objects need to be detected, it is of great interest to employ the radiation decomposed over so many radiation features as possible to allow an in depth analysis and synthesis of the partial images.

Figure 35:
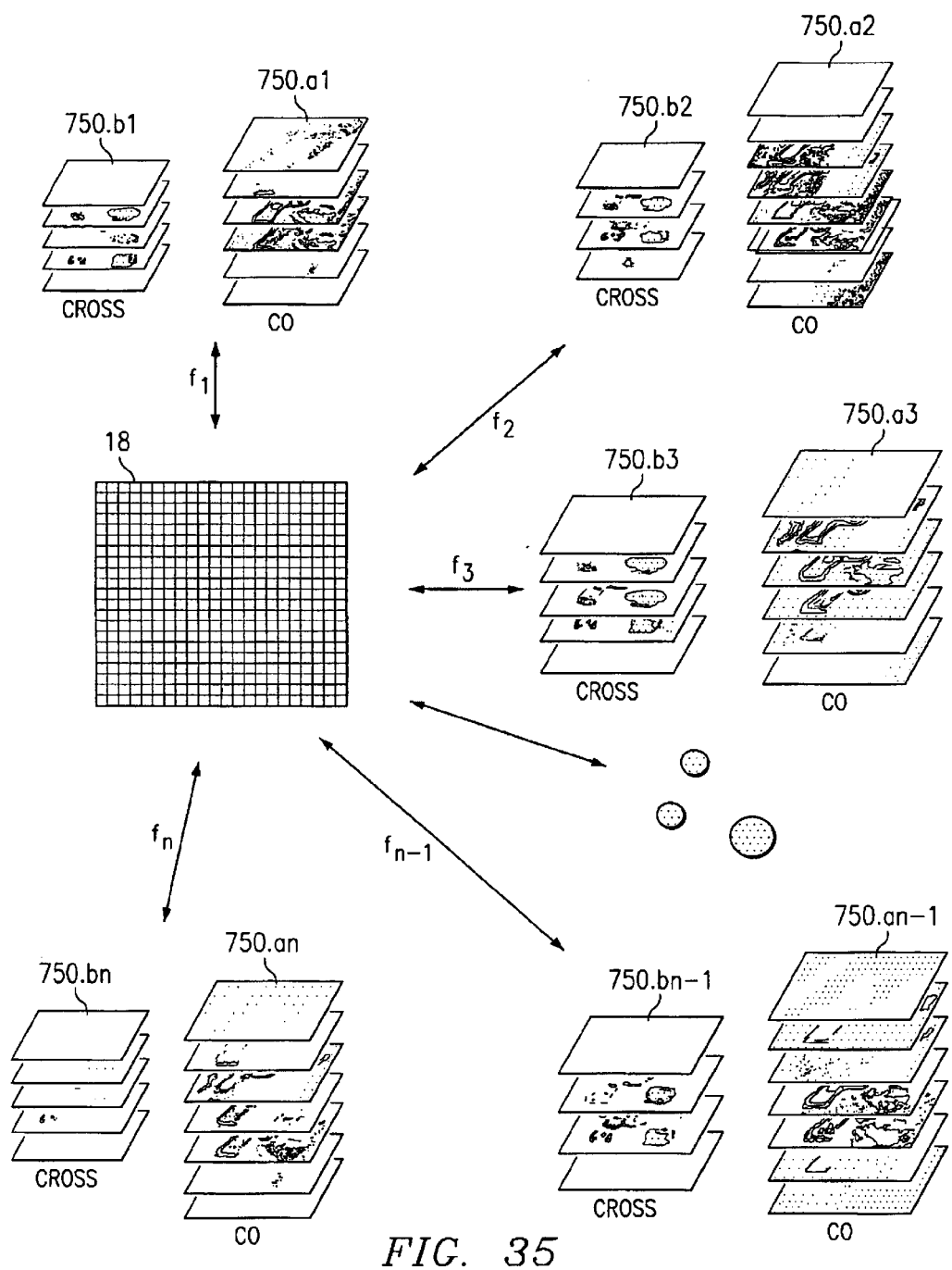
FIG. 35 is a synthesized overview of multi-feature decomposed probing illuminating radiation resulting in plurality of stacks of partial images and synthesized images.

State-of-the art of current s-mmw technology allows to have a plurality of coherent partial sources, exhibiting any distinct value of physical features (frequency, polarization and so on) of the emitted radiation. The radiation, comprising partial components every of which is emitted by said coherent source independently modulated, may exhibit any distribution of said radiation features and their distribution may be adaptively changed in real time. For example, any spectrally wide-band multi-frequency s-mmw radiation may be obtained as a result of the superposition of partial beams emitted by a number of coherent narrow band sources, each of them characterized by its own code. The aforesaid principle of synthesizing an encoded multi-frequency radiation can be extended to other parameters of the radiation components. For example, multi-polarization radiation can be synthesized in the same way. Thereby the type of the modulation employed for encoding carrier frequency may be easily extended to modulation of polarization. Multi-angle component radiation will be produced after scattering multi-frequency and/or multi-polarization by the diffuser. The total amount of multiple-parameter partial images, which can be obtained by the novel imaging technique is schematically presented in FIG. 35. For each carrier frequency of the s-mmw spectrum of source 12, stacks $750.a1$, $750.a2$, $750.b1$, $750.b2$, . . . , $750.n1$, $750.n2$ of partial images received at the receiver array 18 for different angles of incidence and for different polarization states (co and cross-polarization state) of the illumination are stored.

V. Doublets

A proposed principle of s-mmw radiation decomposition was discussed above. In the preferred embodiment, this principle is based on the distinct encoding (e.g., modulation) of multiple radiation components. Such modulation is possible due to the fact that artificial sources of s-mmw radiation are, as a rule, the sources of highly coherent radiation. High coherence of radiation is known to cause a reduction of visual quality of s-mmw partial images but, from another side, allows the realization of modulation principles for independently encoding the radiation whereby each encoded radiation component yields a partial image.

For different implementations different modulation embodiments are proposed. The peculiarities, and pros and cons of distinct modulation techniques are concisely addressed.

High radiation coherence means that the amplitude (or intensity) of the radiation is only substantially different from zero for a particular combination of radiation parameters (frequency, polarization characteristics, directivity, . . . ), whereby each of the parameters is restricted to a very small interval. To realize distinct modulation of radiation signals, the narrow-band nature of the radiation spectrum exhibiting a reduced level of phase-noises is of great interest. Such narrow-band radiation permits different kinds of frequency and phase modulation (FM and PM) techniques of the radiation carrier. For even more enhanced noise immunity, s-mmw radiation may be encoded by particular FM technique for doublets. Hereby the relative frequency and/or phase shift between the twin components of every such doublet are under static or dynamic control. The doublet radiation FM techniques will be discussed in detail later.

The radiation components may be effectively modulated by different amplitude modulation (AM) methods as well. AM methods do not require the frequency purity of the used radiation and may be effectively employed for the modulation of radiation exhibiting different spectral compositions including ones with enough extended bandwidths. Contrary to FM techniques, as a rule, AM techniques allow a simpler apparatus realization but since they are based on modulation of signal power, inherently lead to power losses. In addition, AM techniques are effective and low cost, as a rule, for lower frequencies of the modulation signals (up to 100 KHz–1 MHz) although the possibilities for AM modulation with 100 MHz and higher exist as well.

In some applications distinct radiation components exhibit two or more physical features simultaneously. For example, such components are simultaneously characterized by a particular carrier frequency (100 GHz, for example) and a particular angular propagation (being scattered by distinct diffuser element located at some particular space point). The later case may take place when the diffuser is illuminated by the s-mmw coherent radiation source exhibiting said carrier frequency.

The multiple component radiation may be under at least two different modulation modes. The first modulation mode is applied for encoding a particular carrier frequency. Being primarily modulated, the radiation is modulated a second time by being scattered by elements of the diffuser. In one example, the first modulation mode may be FM while the second is AM.

Double modulation (or even a higher number of modulation modes) is the typical approach for radio communication links and correspondent multiple modulation techniques (e.g., FM-AM, AM-AM, FSK-AM-AM, ASK-AM, PSK-AM and so on) can successfully applied to modulation of s-mmw radiation. Of course the implementation of the receiving apparatus of an imaging system has to be adapted to provide the needed multiple demodulation procedures of the s-mmw radiation.

State-of-the-art s-mmw technology enables the implementation of special kind of frequency modulation to realize s-mmw sources featuring very effective encoded coherent radiation not only for goals of the encoded quasi-optical imaging but also for any communication applications based on the usage of s-mmw radiation. It may be applied in ultra-fast indoor wireless intercomputer links or for ultra safe telecommunication systems exhibiting enhanced noise immunity.

The principle of the proposed FM technique utilizes the simultaneous emission of at least two coherent radiation beams whose carrier frequencies and, in some realizations whose phases, are in a well-defined relationship with respect to each other. The spatial directivities of the beams are preferably the same. The source is able to produce two such coupled spectral lines, which can be referred to as a doublet.

The doublet may preferably be composed from a pair of identical s-mmw voltage-controlled oscillators (VCO), each of which is loaded by a radiation emitting antenna. The antennae are preferably identical and spatially disposed in the same manner. A VCO is known to allow the control of the frequency of emitted s-mmw radiation by means of changing a drive voltage or keeping the frequency stabilized. This fact is widely used in different s-mmw applications including satellite applications, or different radar applications when the frequency of emitted s-mw radiation has to be changeable in some defined manner. The spectral purity is enhanced by phase locking the VCO radiation by means of harmonics of quartz stabilized LF oscillators. The possibility of controlling the frequency of emitted radiation may be effectively used for controlling the frequency difference between carrier frequencies of the doublets.

A generalized scheme of possible waveguide realization of the doublet line radiation source is shown in FIG. 36. The circuit for controlling the frequency shift between doublet signals generated by paired s-mmw VCOs 850, 853 comprises a mixer 846 producing a beat signal of the VCO's signals, which is electrically coupled to amplifier 848 followed by frequency divider 849 which, in turn, is followed by frequency discriminator 852. The voltage at the output of the divider 852 appears to be proportional to the instant frequency difference of the doublet VCOs signals.

By means of the operational amplifier 855, a feedback circuitry is established to equalize the output of frequency discriminator 852 and the output of the modulation signal generator. This equalization is achieved by sending the error output signal of operational amplifier 855 to one of the VCOs 853. This electrical feedback circuitry allows the control of the difference frequency of VCO's signals in accordance with time varying of the modulation signal of the oscillator 854. Due to this fact, the frequency shift between spectral components of such doublet s-mmw radiation source may be modulated. The oscillator of modulation signal 854 may be substituted by a source that produces a constant biasing voltage only. In this case, the frequency shift is static in time and may be chosen in accordance with application needs.

Different spectral regions in a wide spectral band application can be encoded by filling up the spectrum with doublets, each having a distinct frequency shift between its spectral lines. The outputs of VCOs are connected to the same waveguide by means of couplers 841, 842 and corresponding isolators 849 and 847. The waveguide is loaded by a single horn antenna such that both spectral components have the same phase center of their emitting radiation and will therefore propagate identically in free space. Every independent channel of particular VCOs may be provided by independent p-I-n switches 845, 844, which can be used for possibility of switching off one of the channels (in this case the source may be used as a source of single spectral line radiation) or for additional amplitude modulation of radiation of one VCO or both.

Enhanced stabilization of the frequency and essentially enhanced phase properties of the beat signal being produced by the doublet components at the mixer 846 can be achieved if the chain producing the beat Signal (VCO's and the mixer) are phase locked by a reference oscillator 858 producing a highly stabilized lower frequency signal. The reference oscillator may be an oscillator stabilized by quartz with an extremely high quality factor Q (which can range from 1,000,000 up to 1,000,000,000). The beat frequency is compared to harmonics of the reference signal at the harmonic mixer 857. An $N^{th}$ harmonic multiplier block 860 is coupled between oscillator 858 and mixer 857. The output of the mixer 857 is electrically connected to the VCO 853 through operational amplifier 855. The described phase lock loop (PLL) can include, as well, a linear frequency/phase discriminator (852) followed to the harmonic mixer.

The counter—synthesizer may be used as a reference oscillator as well because the signal of one is highly stabilized as well (as a rule on a basis of usage of quartz LF oscillators). The stabilization of the beat signal is much more effective in comparison with the stabilization of the carrier frequency of s-mmw radiation in many aspects. Here, first of all, the carrier frequencies themselves of the VCOs are not synthesized but it is made only for their difference. In this case, the spectrum of beat signals may become very sharply peaked (e.g., below 1 Hz width) if phase lock loops are delicately designed. This can be important because the free running spectrum of a Gunn source may extend over several MHz.

If the reference source 854 is modulated in frequency or/and in phase then the frequency shift between spectral components appears to be modulated FM/PM with reduced phase-noises. This fact is of great interest both for multi-parameter encoded imaging as well as for wireless communication application.

To extract the FM signal from a doublet radiation with modulated frequency shift between the doublet components, it is typically enough to perform only rectification of the doublet signal, which can be realized by any non-linear element such as a Schottky diode. After mutual multiplication of the doublet components at the non-linear element, a correspondent beat signal may be effectively produced. This beat signal will exhibit all the above-mentioned enhanced modulation features. Moreover the self-mixing may be realized only after required amplification of the received doublet signal.

The amplification can be performed in any conceivable way. The radiation may be received by an s-mmw antenna and then directly amplified by low-noise s-mmw amplifiers up to the needed level and then rectified by a suitable non-linear element (e.g. by Schottky diode,) which follows after the circuits of direct amplification.

The received doublet signal may be amplified in any heterodyning amplification circuits. Such circuits are known to be based on down-converting the frequency of received signal up to IF range with subsequent additional amplification of the signal by IF amplifiers. Any down-converting is preferably performed for both doublet components in the same way so their difference will not be changed at all in any heterodyning circuits. Moreover, phase noises of local oscillators (LO) of the heterodyning stage will not influence the resultant beat signal at all because they will be added to every doublet component in the same way and will be automatically self-deleted from the beat signal after the self-mixing of the doublet components. It is a big advantage of the proposed transceiver FM apparatus because in case of heterodyning amplification of standard FM signal, phase-noise features-of the local oscillator have a big impact because the LO phase noises will be automatically transferred to the received signal after correspondent heterodyning of the signal. Hence the stabilization of the LO-frequency is a critical issue in the design of heterodyning circuits for standard FM signals. In the case of doublet spectral components this stabilization issue is not important.

It was mentioned before that for doublet signals, only the stabilization of the doublet difference is important. Because the frequency difference of a doublet is essentially smaller (typically several orders of magnitudes) than its central carrier frequency, phase locking the difference signal will always be performed much more perfectly and easier then phase locking its carrier frequencies. Any frequency stabilization and enhancing phase properties of emitted radiation is based on phase locking the s-mmw oscillator to essentially lower frequency reference oscillator, which can be much easier extremely highly stabilized.

The reference oscillator may be high a stability crystal oscillator if fixed frequency of the s-mmw oscillator is to be stabilize. The s-mmw oscillator is stabilized by means of the $N^{th}$-harmonic of the high-Q reference oscillator. The higher harmonics one needs for the stabilization, the stronger the spectral degradation of this harmonic with resect to the original high-Q reference. Hence the embodiment of doublet spectral lines provide extreme improvement in the phase properties of a doublet with respect to a source emitting a single line.

It should be noted that the stabilization apparatus for s-mmw is significantly more expensive and less reliable than stabilization apparatus for the beat signal. Moreover, for usual s-mmw communication systems, at least two stabilized s-mmw oscillators are needed both for signal emitting apparatus and for signal receiving apparatus. Because of this requirement, this apparatus may be either more expensive or less reliable and noise immune.

S-mmw communication systems are attractive due to the fast growth in communication needs and in the rising speed of electronic components. For transceiving the signals with extra wide band spectrum, the aforesaid doublet signal stabilization may be only periodically performed in some calibration time when the information signals are not transceiving. In this case, there are not any limitations on frequency deviation and speed of such deviation. It is important to note that the beat frequency is not limited for the proposed approach and may achieve 1–3 GHz and even more.

The carrier frequency of the doublet signal may be located at any part of the s-mmw spectrum. It is very attractive because the state-of-the-art technology of direct low-noise amplification circuits allows amplifying signals with carrier frequencies up to 140 GHz (or more) and have tendency to increase the spectral bandwidth. So the doublet embodiment provides a simple implementation of a receiving apparatus for wide band s-mmw radiation that does not require first stabilized local oscillators and second does not require an LO with changeable frequency at all.

Wide band antenna of the receiving apparatus can receive radiation in any wide range (for example, from 70 up to 120 GHz) which can be directly amplified without any heterodyning and then only self-mixing. After the self-mixing the resultant beat frequency signals with enhanced phase properties will be located in the appropriate LF or IF range and be correspondingly modulated in accordance with modulating features of correspondent doublet signals. If some heterodyning procedures are needed for frequency selecting of the beat signals, this may be accomplished in the lower frequency range of the beat signals, simplifying the circuitry and reducing cost.

The principle of encoding the radiation by means of doublets with strictly stabilized frequency shifts can be important for multi-parameter imaging because it allows implementation of multiple encoded illumination of objects and essentially increases the dynamic range (and correspondingly sensitivity) of receiving apparatus because narrower band amplification circuits may be used.

State-of-the art current s-mmw technology allows to have a coherent source exhibiting any distinct value of physical features (frequency, polarization and so on) of the emitted radiation. The radiation, comprising partial components each of which is emitted by an independently modulated coherent source, may exhibit any distribution of radiation features and their distribution may be adaptively changed in real time. For example, any spectrally wide-band s-mmw radiation may be obtained as a result of the superposition of partial beams emitted by a number of coherent narrow band sources. The radiation frequencies of such source may be distinctly different and their spectral distribution may be chosen adaptively to an particular application. A magnitude of the spectral density of such "polychromatic" radiation at some particular frequency in the spectrum is really an intensity of radiation of the correspondent partial source emitted at said frequency.

The aforesaid principle of synthesizing multi-frequency radiation where each component has its own modulation code can be extended to other parameters of the radiation components. For example, multi-polarization radiation can be synthesized in the same way. Thereby the type of the modulation employed for encoding carrier frequency may be easily extended to modulation of polarization. Multi-angle component radiation will be produced after scattering multi-frequency and/or multi-polarization by the diffuser.

Such complexly decomposed and encoded radiation, being scattered by the observable object, will carry much information about the object. All this information may be distinctly extracted from the radiation and independently processed after receiving this radiation by the imaging system supplied by correspondent decoding apparatus.

The optimal multi-features composition of object probed radiation may be adaptively generated depending on the specific application. It may be realized if the scattering properties of objects being needed to be detected are known a priori. The choice of the radiation features that can optimally characterize a particular object can be determined by experimental investigation of the object scattering properties. When a more universal imaging is envisioned when the object needed to be detected is not known beforehand it is of great interest to employ the radiation decomposed over so many radiation features as possible.

Figure 36A:
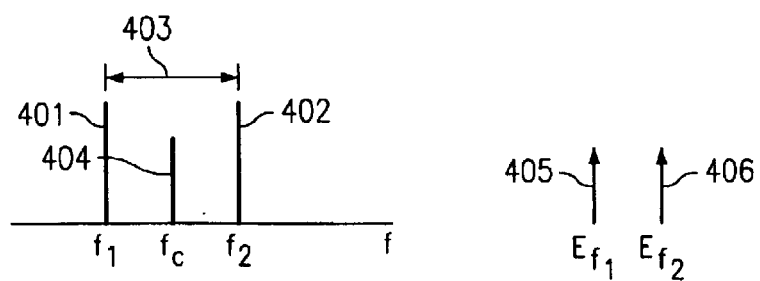
FIGS. 36a–36b are representations of a s-mmw doublet.
Figure 36B:
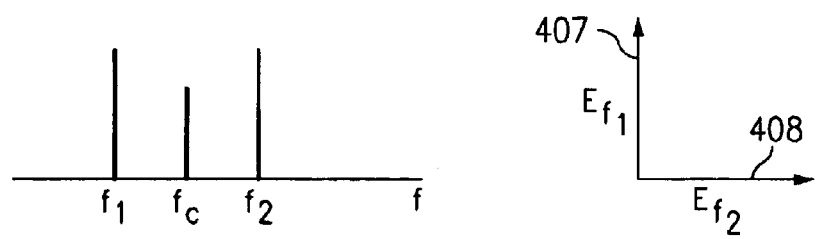

A preferred building block of a s-mmw source is the doublet 400 as illustrated in FIGS. 36*a*–*b*. The doublet is defined as a pair of two closely spaced frequencies 401 and 402. The value of their frequency difference 403 is essentially smaller than the value of their central frequency 404. One can distinguish two different kinds of doublets: cross-polarized doublets (FIG. 36*b*) and co-polarized doublets (FIG. 36*a*). The two components of a co-polarized doublet have the same polarization characteristics 405 and 406, whereas in the case of cross-polarized doublets the polarization states 407 and 408 are crossed.

The doublet radiation can be produced in many different ways some examples of which will be illustrated below.

Some advantages of using doublets as a basic radiation element are now illustrated.

In the case of co-polarized doublets, the corresponding speckled image produced by each frequency component independently will be very similar due to the small frequency difference (e.g., statistically dependent images). The two components of the doublet signals will be mixed by the first nonlinear element (operating in rectification mode) in every amplification channel, electrically connected with correspondent antenna element of receiving array of s-mmw imaging system. By using doublets, one eliminates the need of a powerful local oscillator (or even multiple oscillators) to down convert the s-mmw signal frequency for following amplification and processing of the signal.

Figure 37A:
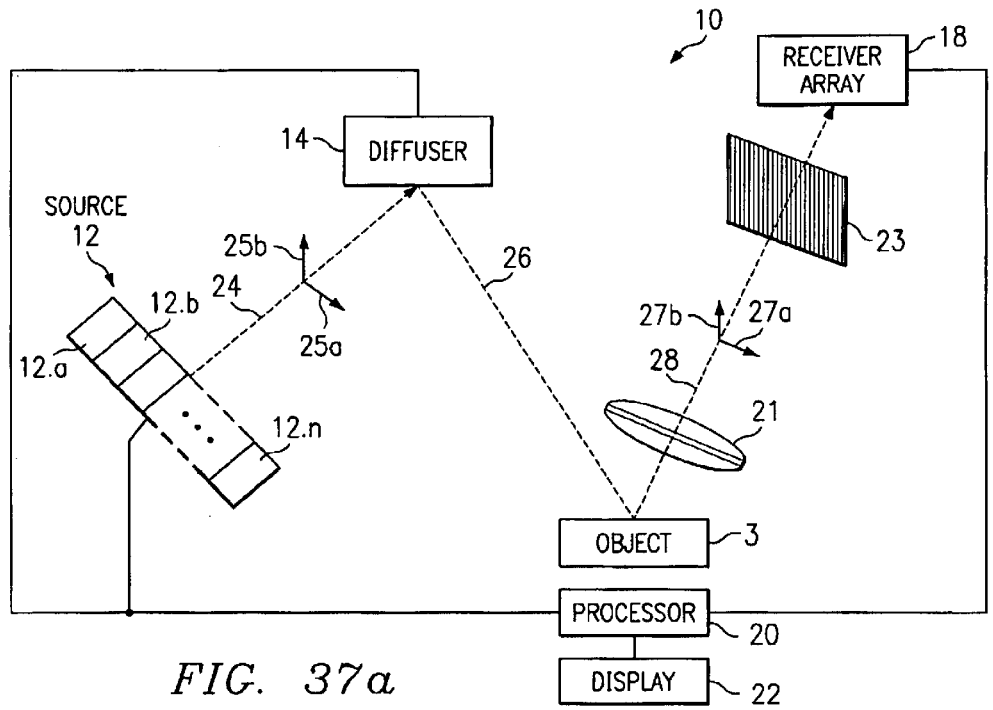
FIGS. 37a–37b show the basic building blocks of a quasi-optical 2D s-mmw imaging system of the present invention for polarization sensitive imaging.
Figure 37B:
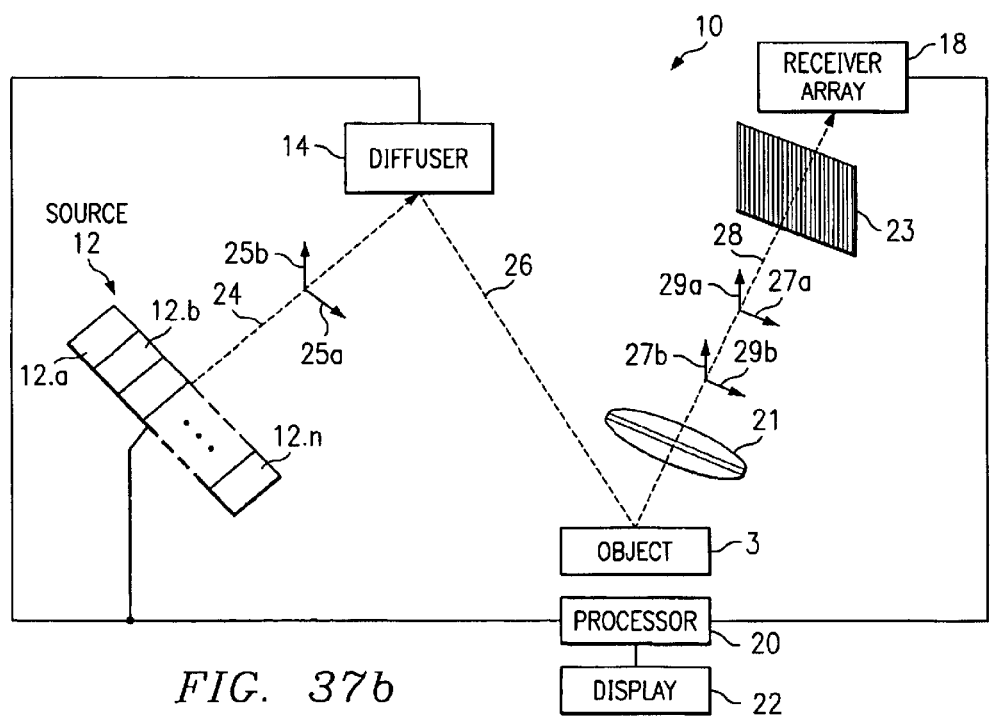

Cross-polarized doublets are preferably used in combination with a polarizing grid 23 as shown in FIGS. 37a and 37b. As shown in the Figure, the polarizing grid 23 is positioned in front of the receiving array 18. When the object 3 under investigation does not induce any polarization changes in the object reflected radiation, both doublet components keep their original polarization states 25a and 25b, but with reduced amplitudes 27a, 27b as indicated in FIG. 37a. As a consequence the polarizing grid eliminates one of the frequencies, such that no beat signal can be generated in the mixer, indicating the absence of depolarizing or polarization rotating materials.

However, when the polarization states 25a, 25b of one or both of the frequencies is affected by the object, for example due to internal mechanical stress (e.g., in plastics) or due to the internal amorphous granular structure of the material (e.g., narcotics, explosives), both as frequencies having polarization states 27a, 27b, 29a, 29b partially transmit through the polarizer such that a non-zero beat frequency signal is generated by the mixer.

Co-polarized doublet radiation may be used for polarization imaging as well if the polarizing grid 23 of the imaging system is oriented to block the radiation 28 when the primary polarization state of one of the components is not changed by a scattering object 16. However, cross-polarized doublet radiation is preferable for polarization imaging in comparing with co-polarized ones due to better polarization sensitivity of receiving apparatus for the same imaging conditions. The latter teaches that the choice of the polarization state of the doublet determines for which kind of materials of the object the imaging system is most sensitive.

The doublet principle of radiation decomposition allows distinct encoding of different multiple radiation components each of which exhibits distinct radiation features. Thereby the number of such radiation components may be really very large as the frequency shift between doublet spectral components may be practically as large as is needed. The effective carrier frequency of particular doublet spectral line may be located at any spectral point of s-mmw radiation. It is only desired that the antennas of receiving array elements be sensitive to the radiation at this spectral range.

After the first rectification element in the correspondent amplification/processing channel, which is electrically connected with particular receiving antenna, the s-mmw doublet spectral line will be down-converted in a spectral range that is defined by value of frequency difference between the spectral components of the doublet. A processing portion of the receiving apparatus should be able to effectively demodulate the received radiation. This means that the apparatus should be designed in accordance with the modulation technique(s) exploited for particular decomposition of object illuminating radiation. Demodulation procedures should be performed in an order inverse with respect to the order during modulation procedures, which were applied for particular radiation decomposition. It is obvious that the demodulation principles and correspondent demodulation circuits will be different in case of different multiple modifications of AM or FM (or their multiple combination).

Figure 38:
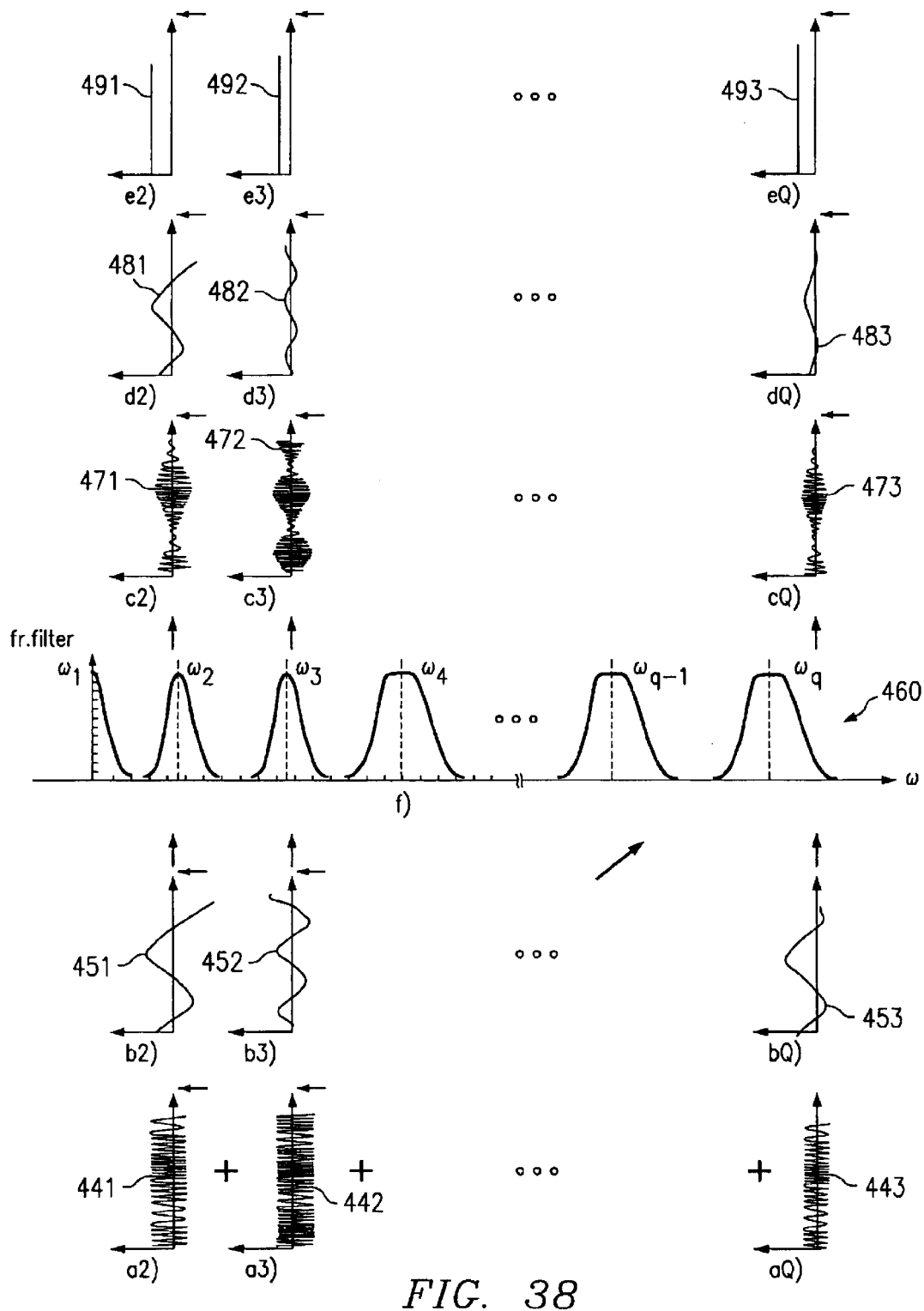
FIG. 38 shows a demodulation principle of multiple FM signals.

A simplified illustration of a possible demodulation principle of multiple FM signals, the spectral locations of which maybe distinctly selected, is shown in FIG. 38. The FM signals, shown in FIG. 38, may be produced by correspondent doublet radiation signals after their amplification and self-mixing or by single FM spectral lines of s-mmw radiation after their down-converting up to desirable spectral range being performed in correspondent heterodyne circuit (s). Curves 451–453 indicate the time—evolution of frequencies of correspondent FM signals 441–443. As shown in the figure, the curves have some well-defined shifts along time-axis of the plots, which are preferably distinct.

The FM signals (time-varied evolution of their amplitudes) 441, 442, . . . , 443 are separately shown in FIG. 38 for illustrative goals although the real signal received by a particular antenna and then down-converted to considered spectral range is a sum of such signals. The maxima of amplitude oscillations of every signal 441–443 exhibits some particular information about scattering properties of those part of observable object surface at which the correspondent antenna element "looks" by means of a focussing lens.

Because the amplitudes of every component of the decomposed of object illuminating radiation is preferably calibrated and stored in memory, any changes of each component's amplitude will be proportional to its coefficients of surface scattering. As every component exhibits distinct physical feature(s) of the incident radiation, hence the scattering properties of the object's surface will be revealed for every particular physical feature of current interest (carrier frequency, polarization state, angle of incidence and so on). Because all other antennae of the receiving array that "look" at other complementary parts of the object surface receive analogous signals at the sane time, multiple images exhibiting scattering peculiarities of object surface (or/and even ones internal structure) will be obtained simultaneously. Each such image will exhibit distinct physical feature of object illuminating radiation. The latter is a basis of essentially enhancing recognition capabilities of the detection system based on s-mmw imaging.

Distinctly located FM partial signals may be distinctly separated by band-pass filter(s) and then independently amplified and processed in different parallel circuits. A comb filter 460 embedded into a particular channel of multichannel receiving apparatus may perform such separation. Because the beat signals frequencies may be very high (e.g., 1–3 GHz), the filters may have a solid-state device realization (e.g., piezoceramic filters, plane acoustic waves, and so on) having high temperature and temporal stability.

Since the proposed principle of radiation decomposition allows having strictly defined frequencies of the beat signals (including the fact that the same filters may be used in the feedback PLL loops of the correspondent doublet s-mmw radiation sources for enhancing stabilization of the beat signals frequencies), the receiving apparatus using the solid state filter components will exhibit reliable operation and simple, low cost performance concurrently.

The FM signals may belong to any spectral range (e.g., KHz, MHz, or GHz ranges) depending on the realization of the receiving apparatus and illumination source system, which will be adapted to real goals of the imaging system operation. At any time, there are a lot of realizations for selective frequency circuits being able to effectively operate in said LF-IF spectra ranges.

For demodulation of selected FM signals appropriate frequency/phase discriminators should be applied. The frequency selective filters may be used for the frequency demodulation as well.

For this goal the central frequencies of the correspondent FM signals should be located on the linear part of the slope of the transmission curve of the correspondent band-pass sub-filter (see e.g., FIG. 38). After filter demodulation FM signals are transformed into time-varied forms of AM signals 471–473 in FIG. 38, the envelopes may easily extracted 481–483. If FM demodulation frequency/phase discriminators are used in the demodulation circuit, the AM signals 481–483 at the discriminator outputs will appear unaffected. The time-varying evolutions of the signal 481–483 will reproduce time evolutions of primary modulating signals 451–453 thereby amplitude maxima of the signals 481–483 will be linearly proportional to amplitude maxima of correspondent FM signals 441–443. The latter can be important to the goals of proper decoding the signals responsible for different radiation components of the received complicated decomposed radiation.

FM signals may be spectrally clustered around every central frequency $\omega_q$ of every band-pass sub-filter (or correspondent frequency discriminator) depending on filter performance.

Amplitude detection circuits (including synchronous detectors) allow revealing amplitudes 491–493 of the signals 481–483. Squared amplitudes of the envelopes are acceptable. Fine structure of demodulated LF signals may be obtained in real time by means of using either a scanning quadrature detection apparatus or by sampling the LF signals by an ADC followed by digital Fourier processing.

Figure 39:
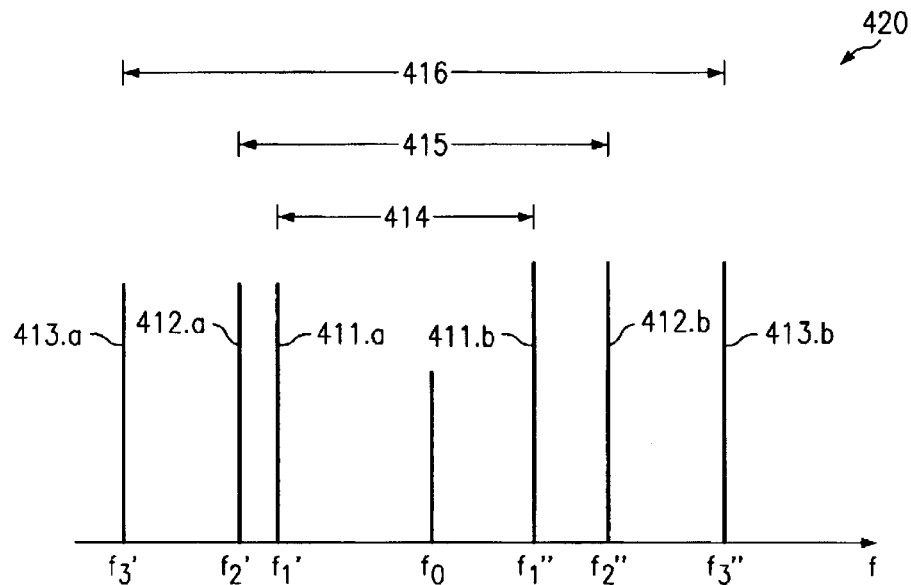
FIG. 39 is a schematic representation of a s-mmw multiplet.

The aforesaid principle of doublet line decomposition of object illuminating radiation is preferable for a majority of applications. S-mmw VCOs, however, can be further extended to multiplet line decomposition of the radiation as well. A multiplet line decomposition is defined as a set of doublets whose central frequencies are very close to each other but with each doublet of the multiplet characterized by a distinct frequency difference as illustrated in FIG. 39. The principal of ordering the spectral components of the shown multiplet 420, comprising of three doublets is as follows: doublet 1 (2; 3) has spectral components 411a, 411b 412a, 412b; 413a, 413b) and frequency differences 414 (415; 416) respectively.

It may be useful when one wants to implement a combined encoding whereby one state of one physical feature of radiation is encoded together with a limited number of states (or magnitudes) of another physical feature (for example, the multiplet may comprise two co-polarized doublets exhibiting mutually orthogonal linear polarization characteristics and almost the same central carrier frequency). The latter allows duly ordering the radiation components with near the same values of physical features (or the same value of one feature from whole set of the features being under encoding).

Generally, the frequency of the beat signal of a particular doublet "n" belonging to a multiplet "m" may be written as $$\omega_{bm,n} = \omega_{sm,n} + \omega_{dm,n} \cos(\omega_{m,n} t + \omega_{m,n}) \quad (4)$$

This formula shows that there could be a static part (or slowly changing one) $\omega_{sm,n}$ and a dynamic part (e.g., a sinusoidally varying part) characterized by its frequency $\omega_{m,n}$ and its oscillation amplitude $\omega_d m,n$. The subscript m denotes the number of the multiplet; the subscript n denotes the number of the doublet in said multiplet.

The radiation components, each of which is emitted by correspondent s-mmw VCO, can be grouped in a set of s-mmw radiation multiplets by means of electronically controlling the radiation frequencies of said VCOs. At the receiver side, these multiplets are self-mixed by the rectification elements leading to beat signals in each antenna element in response to its incident radiation components. In accordance with an organization rule, these beat frequencies will exhibit some special law of their mutual spectral location.

In accordance with one possible organization rule of ordering, the radiation components belonging to the same particular frequency multiplet (cluster) $m_x$, will produce the beat signals, frequencies of which exhibit the same static part $\omega_{sm,n} = \omega_{s,ml}$ for all n components of said multiplet $m_x$ (being distinct for different multiplets) and distinct time-varying parts $\omega_{dx,n}$ for different radiation components belonging to the same multiplet $m_x$ (n=1,2, . . . , $n_{mx}$). This organization rule of multiplet ordering of s-mmw radiation components may be effectively used for encoding multi-parameter radiation, whose spectral composition is not additionally and substantially transformed after being emitted. For example, such spectral composed radiation may be applied in cases of multi-frequency and multi-polarization imaging when the radiation directly illuminates an observable object or when the radiation is previously scattered by a diffuser which is not able to destroy the radiation spatial coherence (e.g., a gradually roughed multi-layer diffusing structure). The radiation may be effectively demodulated in a way described in detail above (see e.g., FIG. 38 where the signals belonging to the same multiplets may be selected by the same band-pass filter and then distinctly processed.

In cases of spatially non-coherent imaging when the radiation, being primarily decomposed over radiation carrier frequencies and/or multi-polarization states, is subjected to additional modulation by the coherence destroying diffuser, each spectral line of the primarily decomposed radiation is additionally spread (and in ordered manner for some kind of diffuser). For simplifying the demodulation process of such decomposed radiation another organization rule of primary ordering of the multiplet radiation components may be proposed.

According to the organization rule, the beat signals produced by the doublets, belonging to some particular multiplet $m_y$ will only be characterized by distinct temporally non-varying (or very slowly varying) parts $\omega_{(\ )my,n}$ (in accordance with the formula (4) thereby any time-varying parts $\omega_{dmy,n}$ will be absent at all ($\omega_{dmy,n}=0$).

Figure 40A:
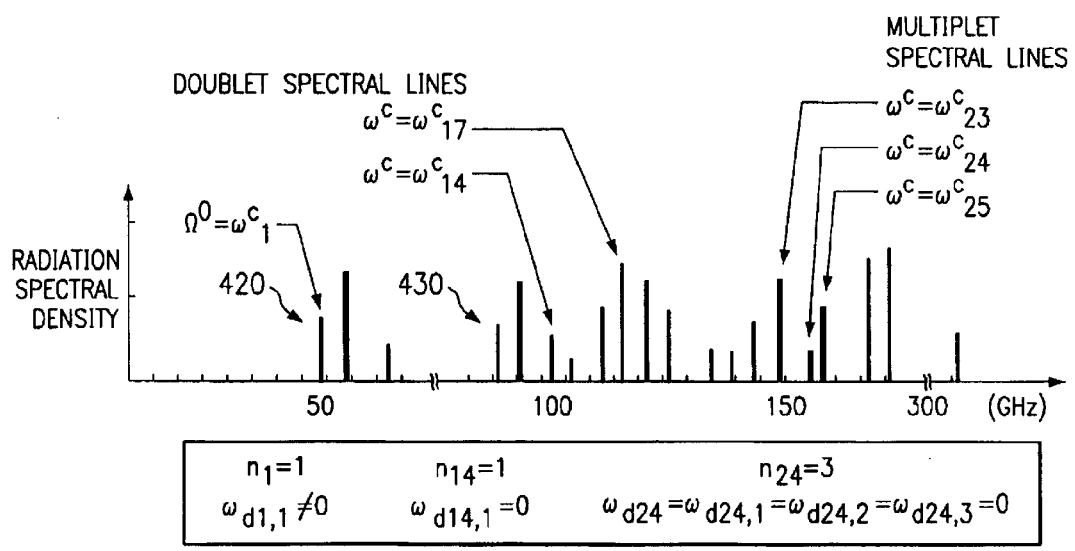

Some possible realization of decomposition of multi-feature radiation comprising doublets and multiplets is presented in FIG. 40, which includes FIGS. 40a–40g. FIG. 40a is an out-zoomed view, showing only the central frequencies of the multiplets, on the spectral axis, which can range within whole s-mmw spectrum (e.g., 30–3000 GHz) or within any limited band of one depending on the application. The doublets and multiplets are numbered (by subscripts e.g. 1, 13, 14, 24, 25 in this example) in accordance with the ascending order of their central frequency. In FIGS. 40b–40g, one zooms in on temporal snapshots of a few doublets (with ordinal numbers 1 and 14) and one multiplet with ordinal number 24.

For illustrative purposes, one doublet (with spectral line ordinal number 1) exhibits the first organization rule of doublets. The snapshots for this doublet are shown in FIGS. 40b and 40c at different moments of time delayed from each other by half an oscillation period of correspondent beat frequency ($\omega_{d1.1}>0$). Snapshots of another doublet (ordinal number 14) are shown in FIGS. 40d and 40e at the same moments of time. The beat frequency of this doublet has no dynamic part. In this case, the signal does not oscillate. The multiplet spectral line (its ordinal number in the total s-mmw spectrum is 24) comprises six spectral components, mutual spectral locations of which are non-varying in time (the second organization rule of ordering).

The snapshots of multiplet m24 are shown in FIGS. 40f and 40g in analogy with the above-mentioned doublets. Multiplet 24 is ordered for producing three distinct beat signals, the frequencies of which are shown as $\omega_{24.1}$, $\omega_{24.2}$ and $\omega_{24.3}$ respectively. Each distinct beat signal, carrying independent physical information about the observed object, will be produced by an independent particular doublet, the components of which exhibit the same radiation feature. When three beat signals of the multiplet 24 are produced, six independent spectral components are needed. In the general case, beat signals formed by spectral components exhibiting different radiation features will carry mixed information about physical and geometrical properties of the scattering objects leading to difficulties for value-to-value recognition of received image information arrays but sometimes it may be useful (for example in the case of cross-polarized doublet).

The implementation of cross-polarized doublets may allow to decrease the number of needed components nearly twice. In this example, low frequency components $\omega^c_{24,n}{'}$ of all the $n_{24}$ doublets of multiplet m=24, are shifted equidistantly with respect to each other in descending order $\omega^c_{24,n'}=\omega^c_{24,n-1}{'}-2\Omega$. Conversely, high frequency doublet components $\omega^c_{24,n}{''}$ are shifted equidistantly with respect to each other in ascending order with mutual shift increased in $n_{24}$ times $\omega^c_{24,n}{'}=\omega^c_{24,n-1}{'}+2n_{24}\Omega$. Here $n_{24}=3$ is the number of partial independent doublets in the multiplet m=24).

The spectral distance between components of the same multiplet should always be larger than the spectral broadening $\Omega_0=2\Omega$, which could be induced by any element in the imaging system, more in particular by the electronically modulated diffuser array. This avoids any overlap of the spectra of distinct doublets (multiplets) after being scattered by the object and-or diffuser.

Figure 41A:
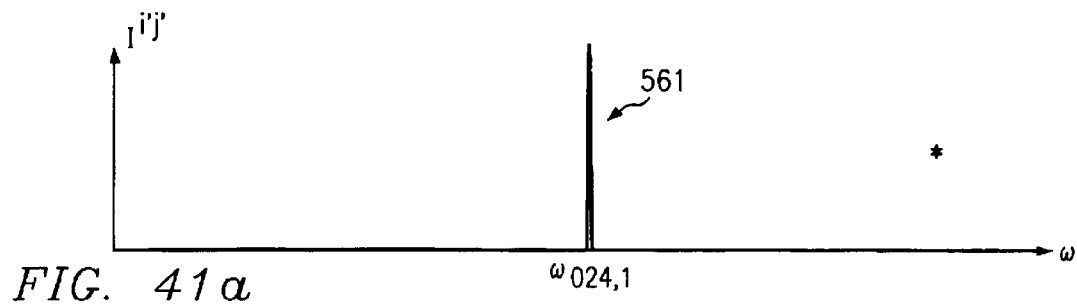
FIGS. 41a–41c are graphical representations of a fine structure of beat spectrum of a doublet.

It was discussed that the beat signal spectrum will exhibit a set of narrow band spectral lines without any spectral broadening only if the composite radiation is directly directed towards the observed object or to a (e.g., multilayer) diffuser being not able to destroy the spatial coherence of the radiation A fine-structure of non-broadened narrow-band spectrum of a beat signal produced by particular doublet spectral line radiation, which is scattered by object (and by said non-coherence destroying diffuser) and received by particular antenna, is shown in FIG. 41a. The fine structure of the beat signal will reproduce in average the spectral structures of the doublet components. It will be a single narrow line (having a spectral width being practically equal to twice the width of the primary doublet component) spectrally located at the value of difference between carrier frequencies of doublet components $\omega_{s24,1}$. Without any loss of generality, only one beat signal exhibiting frequency $\omega_{s24,1}$ of multiplet 24 is shown in FIG. 41a.

If the radiation is directed first to the diffuser array, which is intended to destroy the radiation spatial coherence, then every spectral component of the radiation will be additionally spectrally decomposed and correspondingly spectrally broadened. This is connected with the fact that every spatially different element of the array will modulate the scattering radiation at a particular frequency.

Figure 41B:
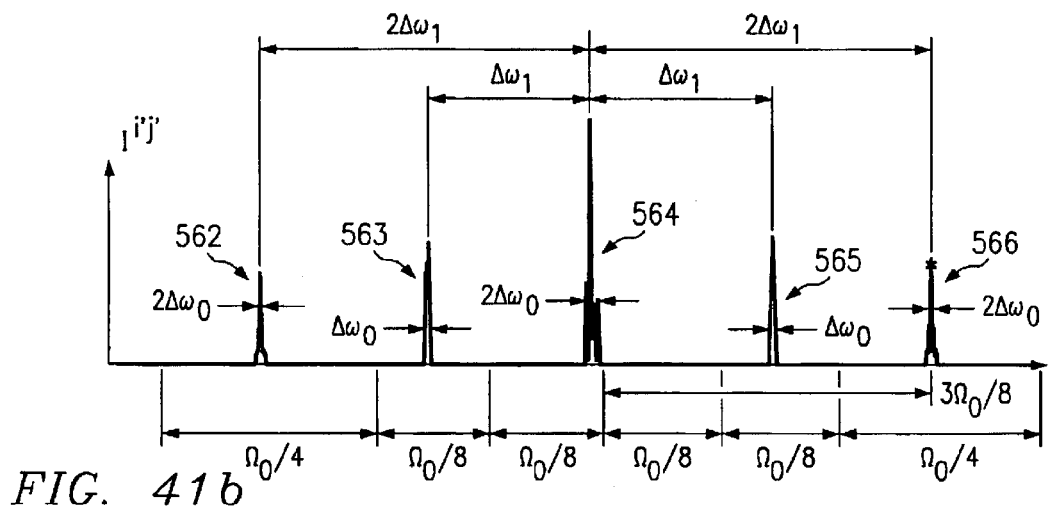
Figure 41C:
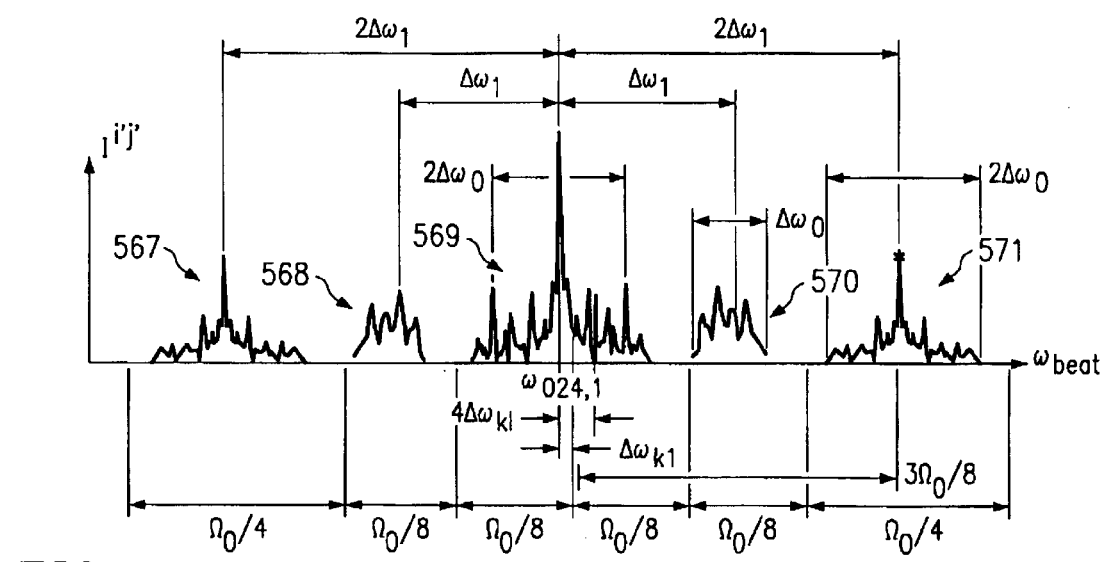

If the radiation primarily illuminates the diffuser consisting of an array of independently modulated scattering elements, then the spectrum of scattered radiation will be broadened depending on type of scattering elements and peculiarities of spectrum of modulating signals. FIGS. 41b and 41c depict two different possible transformations of the spectrum of the beat signals after multiplet components have been scattered by diffuser elements, which induce amplitude modulation of the scattered radiation. Such kind of modulation may be performed by the diffuser being an array of antenna-coupled loads with modulated impedance.

The broadened spectra of beat signals are depicted in FIGS. 41b and 41c for different cases of modulating spectra of the diffuser elements. In the beat signal spectrum 561 of FIG. 41a, a doublet, primarily exhibiting single narrow-band line, will be transformed in an extended spectrum with width $\Omega_o$ which consists of distinct intermodulation sidebands of different orders 562–566 in FIG. 41b and 567–571 in FIG. 41c. The zero order spectral bands 564, 569 of the beat signal are centered at the frequency $\omega_{s24,1}$, the +/– first order sidebands 563,565 and 568,570 are shifted relatively to the frequency $\omega_{o24,1}$ by a value $\Delta\omega_1$ being equal to the average of all frequencies of modulating signals. The +/– second order side-bands will be correspondingly shifted by a value +/–$2\Delta\omega_1$ relative to frequency $\omega_{s24,1}$. Only first order sidebands, characterized by particular frequency shift, will contain the information about the value of modulating frequency of particular elements. The spectral density of the signal at said spectral point within the first order side-band will be proportional to spectral density of doublet n=1 of multiplet m=24 (in this example) after being scattered by the particular diffuser element which is distinctly modulated by the signal exhibiting modulation frequency of said value (being equal to the said frequency shift).

It is obvious that the width of first order side-bands $\Delta\omega_0$ will be equal to width of modulation signal spectrum Zero and +/– second order side-bands contain different combinations intermodulation products of paired spectral components extended after being scattered by the diffuser. These sidebands have no distinct information about diffuser elements but they can be very effectively used for goals of enhancing the visual quality of resultant images because mutual spectral density components here are really two-frequency image components.

Contrary to the two-frequency images formed by two radiation components with essentially distinct carrier frequencies being emitted from the same spatial point, said two-frequency images will be formed by multiplication of two components with near the same carrier frequencies but being scattered by essentially distinct elements of the diffuser array and, as a consequence, will preferably have essentially distinct angles of incident on object surface.

FIG. 41b presents the case when the central frequency of modulation signals $\Delta\omega_1$ is much larger than the spectral width $\Delta\omega_0$ containing all the modulation signals. Hence the side-bands of first order 563, 565 are narrow bands ($\Delta\omega_1>>\Delta\omega_0$).

The case where $\Delta\omega_0$ is comparable with $\Delta\omega_1$ is shown in FIG. 41c. Here all spectral parts are proportionally extended around their primary central frequencies. If all the elements of the diffuser array are modulated at a different frequency and if said modulation frequencies differ from each other by a value $\Delta\omega_{kl}$ and the total number of array elements is N=$k_0$=$l_0$ ($k_0$, $l_0$ are the rows and columns of the array of diffuser elements) then $\Delta\omega_0 = \Delta\omega_{kl} \times N$. If the modulation frequencies of the diffuser elements are distinguishable at the receiver side, then radiation scattered by a particular diffuser element of the array can be identified in each receiver element at the spectral points corresponding to the first order sidebands (568, 570). The same identification can be derived when the diffuser elements are partitioned in clusters, each cluster having a particular distinguishable modulation frequency.

Figure 42A:
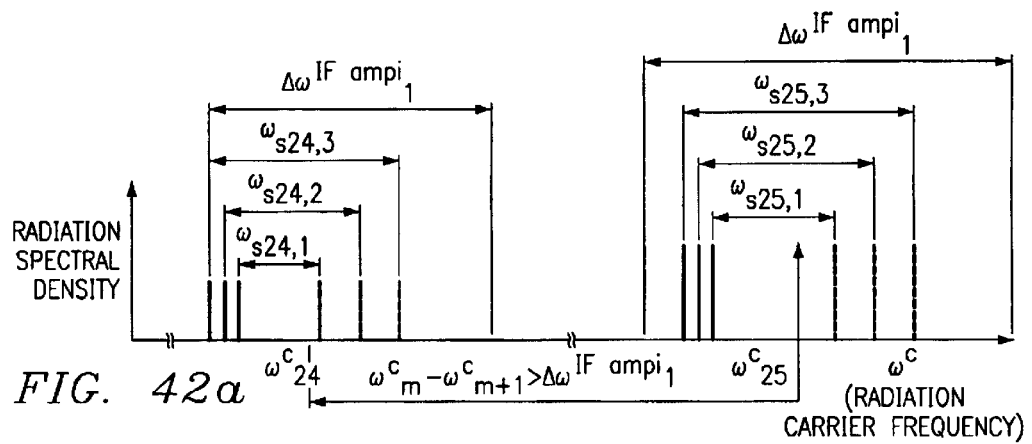
FIGS. 42a–42b show a spectral composition of multiplet radiation.
Figure 42B:
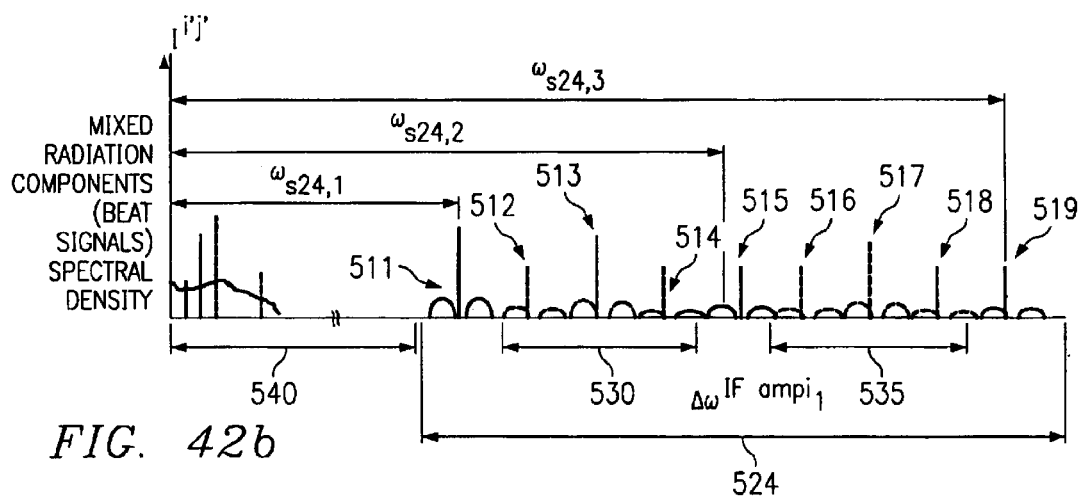

The possible spectral composition of multiplet radiation (multiplet 24 and 25) and the spectrum of beat signals for all components of multiplet 24 are shown correspondingly in FIGS. 42a and 42b. The fine structure of beat signals shown in FIGS. 41b and 41c are schematically only depicted in FIG. 42b. It will be shown that three different intervals in the beat spectrum can be distinguished. These intervals are distinguished by their origin of intermodulation products:

1) unmixed doublet intermodulation products, i.e., the beat frequencies of spectral lines belonging to the same doublet and called the unmixed doublet interval;
2) equivalent mixed doublet intermodulation products, i.e., the intermodulation products of spectral lines belonging to different doublets, but lying at the same side of the doublet=equivalent mixed doublet interval; and
3) non-equivalent mixed doublet intermodulation products, i.e., the intermodulation products of spectral lines belonging to different doublets, but lying at different sides of the doublet non-equivalent mixed doublet interval The information content of the beat signal spectrum relating to the multiple s-mmw spectral lines will be localized in a strictly defined spectral frequency sub-range called the unmixed doublet information interval 524 and may be easily checked for any doublets. This information interval 524 may be defined as $$\omega_{b,m}^{low} \leq \omega \leq \omega_{b,m}^{high} \tag{5a}$$

$$\omega_{b,m}^{low} = \omega_{m,1''}^{c} - \omega_{m,1'}^{c} - \Omega \tag{5b}$$

$$\omega_{b,m}^{high} = \omega_{m,n_{m''}}^{c} - \omega_{m,nm'}^{c} + \Omega \tag{5c}$$

The frequency of beat signals formed by the paired radiation components with the same radiation attributes (intra doublet components) will be equidistantly separated by a value being equal to $2(n_m+1)$ $\Omega$ inside this spectral interval so the position of the beat signals (511, 515, 519) of doublet n of multiplet m may be found as $$\omega_{bm,n} = \omega_{sm,1} + 2(n-1)(n_m+1)\Omega, \; n=1, 2, \ldots, n_m \tag{6}$$

The frequencies of the $2n_m$ beat signals (512, 513, 514, 516, 517, 518) of non-equivalent mixed doublet components are equidistantly distributed at every non-equivalent mixed doublet interval 530, 535 between nearest frequencies. (Mixed-doublet components are paired radiation with distinct radiation physical features. Such components may produce beat frequencies as well). The frequency step between the different non-equivalent mixed-doublet intermodulation products inside these intervals 530, 535 is $2\Omega$. Some of these signals may represent interest for imaging goals, others may be the result of unrecoverable mixing of partial images for different radiation attributes and have not to be used in further signal and image processing.

It can be seen from FIGS. 42a–b that overlapped intermodulation products for equivalent singlesided components of mixed doublets like $\omega_{m,n}^{c}{}' - \omega_{m,n-1}^{c}{}'$, $\omega_{m,n}^{c}{}' - \omega_{m,n-2}^{c}{}'$, $\ldots$, $\omega_{m,n}^{c}{}' - \omega_{m,n-1}^{c}{}'$, $\omega_{m,n}^{c}{}'' - \omega_{m,n-2}^{c}{}'$, $\ldots$ will be concentrated in the equivalent mixed doublet interval 540 defined as $$0 \leq \omega \leq \omega_{inter\;mod,m}^{high} \tag{7a}$$

$$\omega_{inter\;mod,m}^{high} = 2(n_m - 1)^2 \Omega \tag{7b}$$

This interval 540 of the beat signal spectrum cannot be used for either extracting information about the object or enhancing an image quality by following processing.

Figure 43:
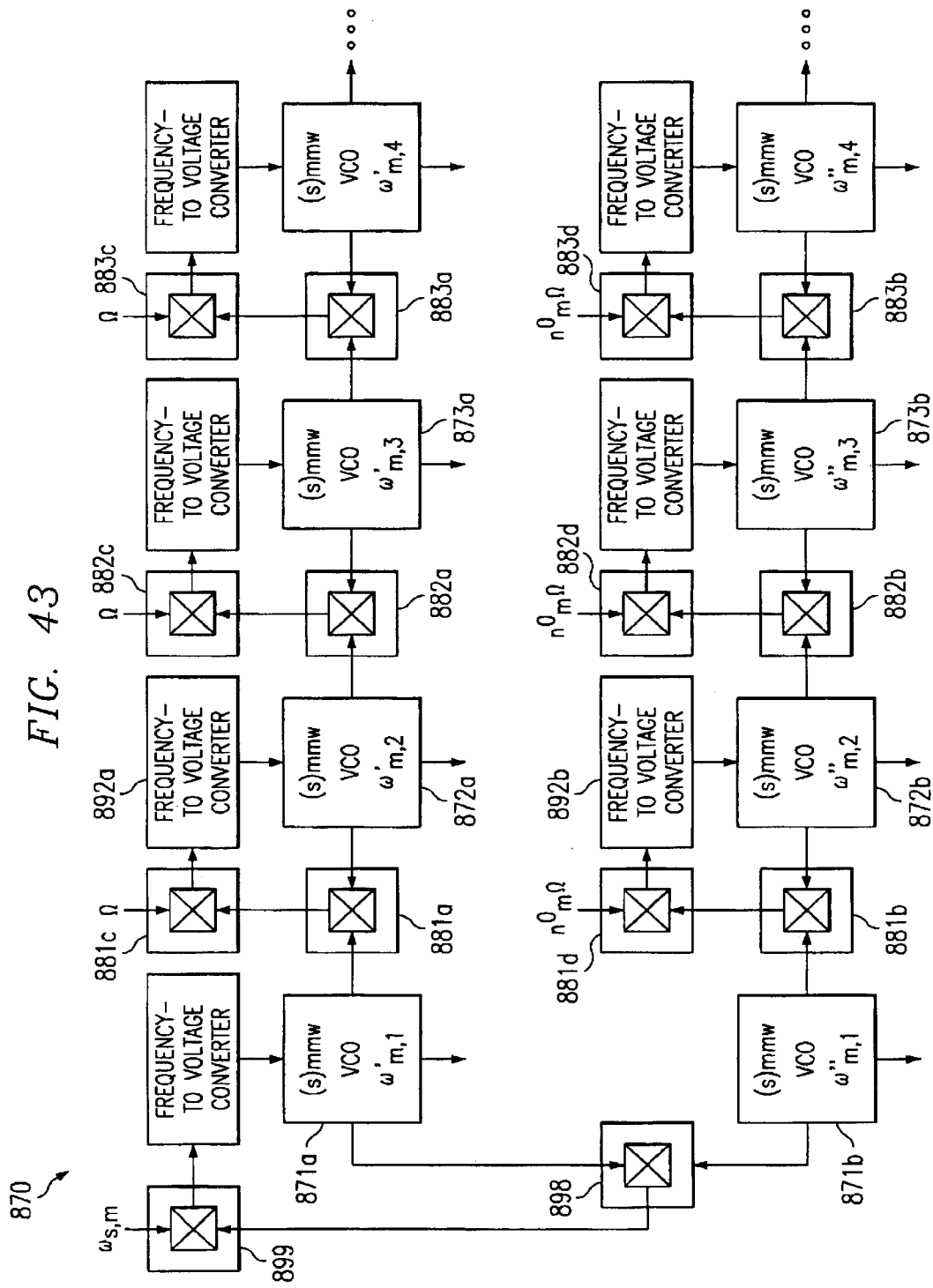
FIG. 43 shows block scheme of implementation of VCO multiplet radiation.

A generalized scheme for ordering the doublet components within a multiplet will now be discussed. FIG. 43 presents a block diagram of a s-mmw controlled composite source 870 emitting the radiation of a multiplet that includes n strictly ordered doublets. Two equivalent branches exist: the branch of the lowest frequency components comprises the VCO 871a, . . . , 873a, . . . which are shifted in frequency by a value $\Omega$ and the branch of the highest frequency components comprises the VCO 871b, . . . , 873b, . . . which are shifted in frequency by a value $n_m^0 \Omega$. The difference between two consecutive components of the lower frequency branch is stabilized by means of mixers with subscript a and c. As an example the frequency difference between VCO s-mmw sources 871a and 872a is controlled by means of a mixer 881a, having as input some radiation of the two s-mmw frequencies. The output of this mixer 881a is combined with the lower frequency difference value in the mixer 881c, which sends its output to the frequency-to-voltage converter 892a, which controls the VCO s-mmw source 872a. In a completely stabilized case the output of this frequency-to-voltage converter is zero, indicating that the frequency difference is equal to the required frequency difference. Similar reasoning for the consecutive VCO can be followed. In the higher frequency branch the stabilization of the frequency difference between the two consecutive VCO s-mmw sources is achieved by means of the combination of mixers having subscript b and d. As an example mixer 881b receives s-mmw signals from 871b and 872b, whereby the mixed output is further mixed with the high frequency difference signal $n_m^0 \Omega$ in mixer 881d. Finally the output of mixer 881d serves as the input to the frequency-to-voltage converter 892b, which drives the s-mmw source 872b. Again similar reasoning can be extended to the other VCO s-mmw sources of the high frequency branch of the multiplet 870.

Finally at the input of this chain, one finds two other mixers 898 and 899 which serve to stabilize the frequency difference $\omega_{s,m}$ of the first-doublet 1 of multiplet m. Two independent inputs, oscillator 871b and the external oscillator providing the frequency signal $\omega_{s,m}$ are controlling the complete multiplet. It is possible to sweep the multiplet over some range of the s-mmw spectrum by sweeping source 871b. All the other source keeping the required frequency differences will follow.

VI. Polarization

In another aspect, some embodiments utilize polarization sensitive imaging as a powerful additional asset in object detection. In polarization sensitive imaging an appropriate polarization state analyzer is provided at the receiver side to analyze changes in the polarization state of the radiation due to polarization dependent scattering and reflection after its interaction with observed object. Detecting and analyzing at the receiver side these polarization state changes, yields new image information about objects, irretrievable in intensity sensitive imaging. Polarization information can be used to obtain additional physical information about the object, e.g., it enhances the possibility of discriminating man-made objects from clutter caused by a natural background. It can help to differentiate different natural surfaces with similar spectral signature. It can also increase the signal-to-noise ratio, for example, in the cross-polarization state as will be explained below, allowing the detection of masked objects with decreased level of false alarms.

It is known that polarization sensitive signatures depend on various factors including (an)isotropic material refractive index, surface roughness, surface shape within a single viewing resolution element, the degree of granularity of the material (e.g., going from monocrystalline towards amorphous), the mechanical stress inside the material, the frequency of interest, view angle, and the radiation environment. Different interactions can lead to different polarization effects. Three examples are: 1) polarization, i.e., the amplitudes of the base electric field components are essentially differently scattered by the object; 2) polarization rotation and phase retardation in anisotropic materials; and 3) depolarizing effects in amorphous materials or due to surface roughness where a major percentage of the polarized illuminating radiation is converted in an unpolarized state after its interaction with observed objects.

The angular dependence of the polarization sensitive reflection and scattering is important as well because metals and non-metals clearly behave differently. As an example, for an opaque object with a quasi-flat surface, the largest polarized signature components are mostly observed at viewing angles in the range from 60–85 degrees (measured with respect from the normal to surface). In addition, the percentage of depolarization inherent with plastics (typically more than 85–90%) can be used to additionally confirm that an observed object in the image is in fact made from plastic. This could provide a distinguishable feature for detecting plastic weapons.

On the contrary, metal surfaces exhibit much smaller depolarization ability over a wider range of angles of incidence. Normally incident radiation will not exhibit any polarization effect in metals. In addition, the spatial distribution of geometrical irregularities of the object's surface or its internal structures (for transmittance materials) can be revealed. This is due to s-mmw polarization sensitive imaging when the angles of incidence of radiation are near to the surface normal (generally between about 0 and 40 degrees).

Since metallic and plastic man-made objects are able to induce distinguishable changes in polarization characteristics of scattered s-mmw radiation, polarization sensitive imaging can essentially increase the discrimination capabilities of imaging systems to increase signal-to-clutter ratio.

An angular-polarization decomposed imaging embodiment is intended to realize an innovative s-mmw technique by extracting these effects properly and in real time. When the principle of decomposition by means of, for example, FM-coding and/or doublet coding is applied to the angle of incidence and the polarization state, the receiver apparatus provided by a polarizer can distinguish independent images for different combinations of angle of incidence and polarization. The performance of the angular-polarization sensitive quasi-optical imaging system will depend on the polarizability of a wide spectral band metal grid polarizer, operating over a wide range of angles of incidence.

The polarization sensitive scattering and reflection of every particular area of the object, which is observed under a particular angle of view by each detector element, will be recorded at the same imaging frame. While illuminating an object by polarization and angular coded spatially non-coherent radiation in accordance with the aforesaid embodiment, an angular orientation of every object surface part, fitting into field of view of correspondent detector array element, may be revealed by means of polarization sensitive imaging.

Such possibilities appear when the imaging system encompasses a rotating polarizing grid that can obtain four polarization images obtained at 0 (the so called co-polarization state), 45, 90 (the so called cross-polarization state) and 135 degree orientation of the grid about optical axes of imaging system. The images can be combined at every pixel in accordance with known equations and the Stokes parameters (and the coherence matrix as well). Accordingly, the scattered radiation at every resolution cell of scattering surface can be obtained. Images of the degree and angle of polarization of the radiation scattered on the object, obtained by a posterior processing of the arrays of the Stokes parameters can reveal smooth relative changes of the surface orientation for the majority of man-made plastic objects (including mines).

In the s-mmw spectral range, frequency-dependent resonance effects may take place for majority of man-made objects. These effects can be more distinctly revealed due to a multi-frequency polarization sensitive imaging.

Figure 44:
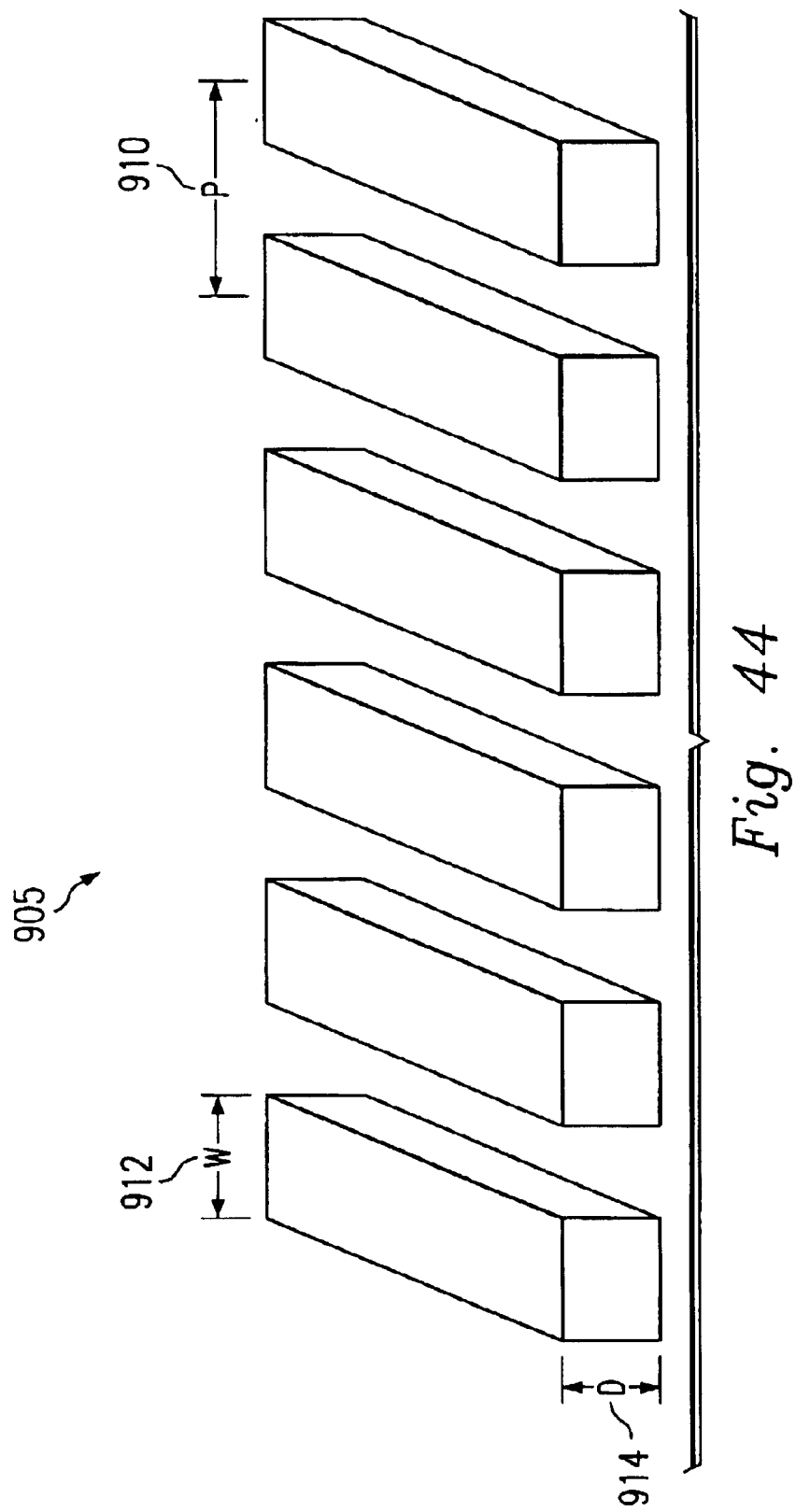
FIG. 44 is a three-dimensional view of a polarizing grid.

For adequate operation in multi-frequency imaging systems, it is preferred that the polarizing grids provide sufficient performance over a wide spectral range and a wide range of angles of incidence. A preferred embodiment polarizing grid 905 comprises closely spaced metal wires or conductive strips on a transparent material as shown in FIG. 44. This grid polarizes the incident radiation by transmitting radiation components having an electric field vector perpendicular to the direction of metal lines and reflecting the other polarization if the wire/strip pitch (center-to-center separation) 910 is much smaller than the wavelengths of the spectral component of the incident radiation.

Figure 45A:
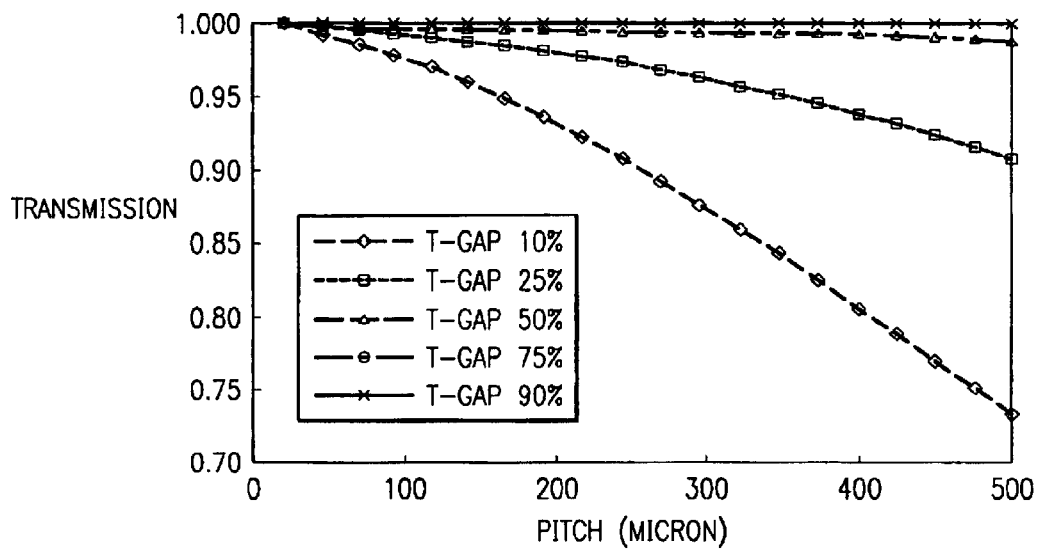
FIGS. 45a–45b are graphs illustrating pitch and airgap dependence of polarization characteristics of polarizing grid suspended in air for wavelength equal to 3 mm.
Figure 45B:
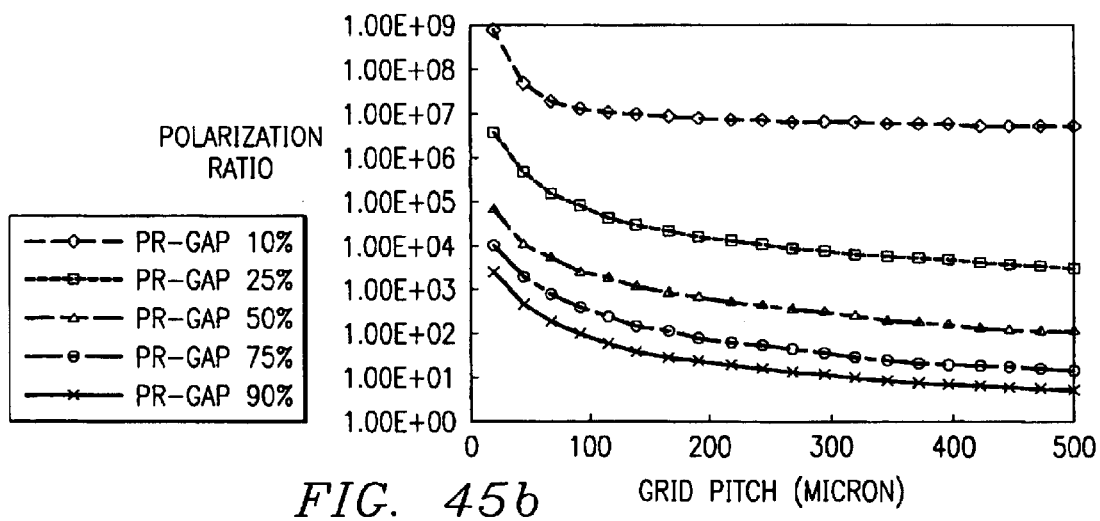

In FIGS. 45*a* and 45*b* different theoretical transmission and polarization ratio curves are plotted for monochromatic radiation having a wavelength equal to 3 mm incident on a gold grid suspended in air and whereby the metal strips with a height equal to 2 micron. The geometrical parameters of the metal grid are the metal width 912, the period 910 and the metal thickness 914. It is obvious from these curves that smallest grid pitches yield the highest desired transmission and polarization contrast ratio. High polarization contrast ratio allows very sensitive cross-polarization imaging.

A compromise is to be taken between this grid pitch and the air gap between the metal stripes. The largest grid pitches can be realized with the cheapest and most reliable technology. When the pitch goes down, the technological efficiency gets a function of the asymmetry of the wire grid. The highest efficiency is obtained for the most symmetric structures (e.g., 50% air gaps). Air gaps larger than about 50% do not provide any advantages as further optimization of the transmission coefficient is not desirable for most imaging applications.

Figure 46A:
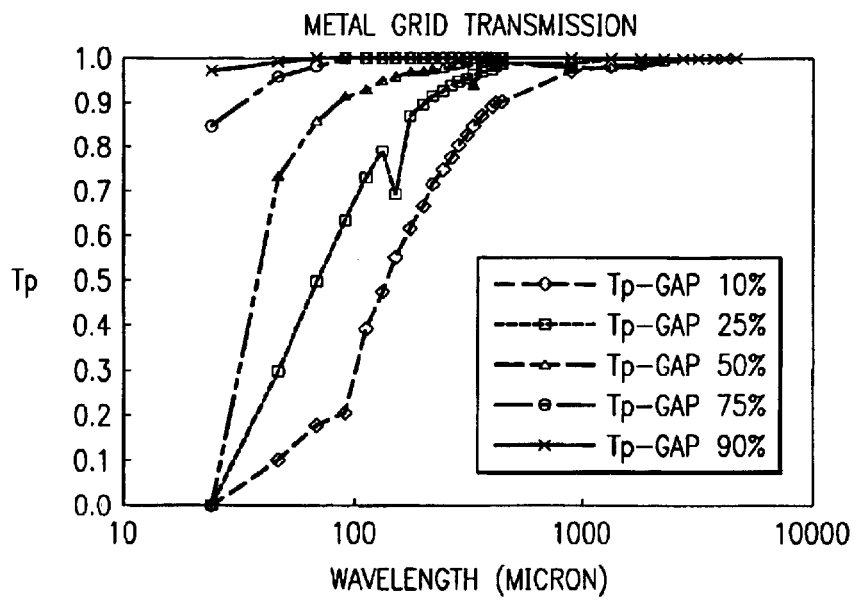
FIGS. 46a–46b are graphs illustrating wavelength and airgap dependence of polarization characteristics of polarizing grid suspended in air for grid pitch equal to 25 $\mu$m.
Figure 46B:
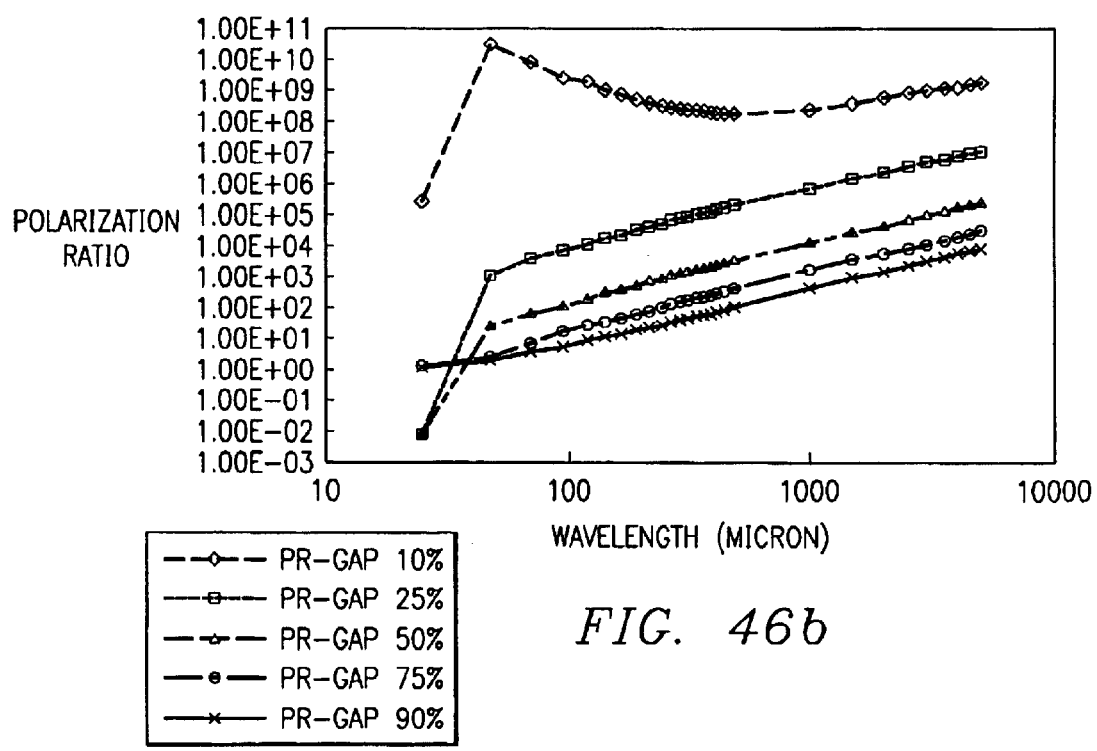

The design issues for a multi-frequency approach are shown in FIGS. 46*a* and 46*b*. Here the pitch of the metal grid is kept constant and equal to about 25 microns. The smaller the airgap, the larger the smallest wavelength of the illuminating radiation should be for having sufficient transmission level. For airgaps of about 50% or more, about 95% transmission is achievable when the minimum wavelength in the spectral composition of the radiation is at least 6 times larger than the period of the metal structure. For air gaps of 10% this minimum wavelength needs to be about 25 times larger than the period of the metal structure. Finally, the contrast can be further improved when the metal strips are thicker, further decreasing the transmission of the cross-polarized radiation. The transmission of the co-polarized radiation is not a strong function of the metal thickness, however, the transmission of the cross-polarized radiation is a very sensitive function of this thickness. Another factor that could affect the cross-polarized transmission coefficient is the manufacturing tolerance of the grid.

Figure 47:
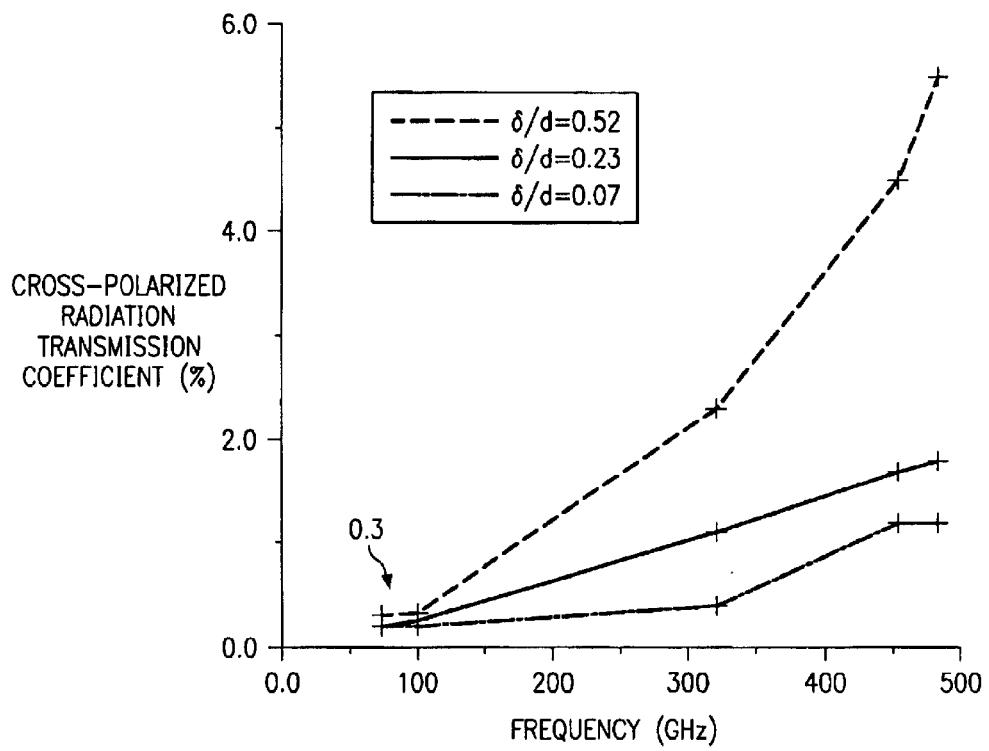
FIG. 47 is an exemplary graph showing the influence of mechanical tolerances on the transmission characteristics of the wire grid.

FIG. 47 illustrates three different curves to show the wide-band performance for different wire pitch irregularities. The different experimental curves show transmission coefficients of different wire polarizing grids 905, in which the wire pitch 910 was made to fluctuate according to a Gaussian distribution with selectable standard deviation σ. The grids wire diameter is equal to about 25 μm and the middle pitch is equal to about 100 μm. It is clear that at lower frequencies, where the wire spacing remains much smaller in comparison with the wavelength, the transmission coefficient slightly changes with rising mechanical imperfection of the grid. At higher frequencies, where the spacing is comparable to the wavelength, the transmission coefficient rises sharply for fractional deviation above about twenty-five percent. If accurately manufactured, such kind of grids should have an extrapolated upper frequency limit of about 1 THz for a wire diameter of 10 μm if 1% transmission of the cross-polarized radiation is considered to be sufficient for polarization imaging. Such wide-band operation is quite sufficient for proposed multi-frequency imaging technique.

VII. Detector

In order to detect the wide band s-mmw radiation reflected and scattered from the objects under investigation in quasi-optical imaging, the preferred embodiment uses arrays of integrated wide band antenna coupled non-linear elements (diodes or square law devices). In this context the term detecting needs to be interpreted in a broader sense. A single element collecting the incident radiation and yielding a response in accordance with the incident radiation is an act of detecting. An array of elements, each of them collecting the radiation incident on their respective area, which can also be interpreted as spatial sampling the radiation signal, and delivering an array of signals in accordance with the incident radiation is another act of detecting. It is well known in the art that Schottky diodes are preferably used in s-mmw nonlinear receivers because they have a very large operating bandwidth. As an example, they can be designed to pick up signals up to 1 THz or more.

Alternatively, or in addition, many other non-linear elements can be successfully used for these goals. Preferably, these elements include frequency-independent antennas. For example, the element could be a structure that is only determined by angles of conductive antenna elements, for example, a bow—tie antenna As another example, the element could be a structure having self-complimentary planar arrangements, such as where metallic and non-metallic parts can be interchanged, e.g., spiral antennas, log-periodic antennas and so on. Truncating these ideal structures to finite dimensions keeps the lowest frequency limit of their wide band operation in the frequency range of interest. Spiral antennas exhibit circularly polarized antenna patterns with extremely low cross-polarization levels. Log-periodic antennas exhibit linearly polarized patterns with −20 dB or near −10 dB cross-polarized components depending if the antenna is either located in free space or being disposed on substrate lens.

Wide-band performance of the antennas may be effectively employed for sub-harmonically pumping the integrated receivers. The basic idea of this preferred embodiment is the possibility to receive both the subharmonical signal of the local oscillator (LO) and the image s-mmw signal by antenna simultaneously. The non-linear element coupled with antenna is intended here for mixing the $N^{th}$-order harmonic of the LO signal and said s-mmw signal. The antennae should be designed in such way that the lowest resonant frequency of the antenna will be higher than the probable frequency of the LO signal so that the antenna will not reradiate the LO signal in free space. In this case the frequency of LO will be N times smaller than the frequency of incoming s-mmw radiation. The latter provides a big advantage because the LO with relatively low operating frequency has much better operation performance. Moreover if a frequency tuned LO is able to cover some frequency range $\Delta\omega_{LO}$, then the receiver operating in subharmonic mode will be able to cover N times this $\Delta\omega_{LO}$ frequency range, e.g. if chosen multiplification order of the non-linear element N=10 and the sweeping range of LO frequency $\Delta\omega_{LO}$=10 Ghz, then the operating frequency range of the integrated receiver will be equal to $N\times\Delta\omega_{LO}$= 100 GHz at least. The said principle of sub-harmonically pumping a mixer may be employed for any kind of mixers and, of coarse, including wave-guide mixers as well but integrated receiver have better performance for frequencies higher than 300 Ghz.

Another type of antenna, suitable for monolithic realization of the integrated receivers is the end fire (traveling wave) antenna. Due to peculiarities in its construction—they are extended in the direction along the optical axes of quasioptical system—they make correspondent 2-D receiver arrays very compact because they allow the z-axes (being parallel to the optical axes) for propagation of the imaging radiation and allow to provide the X-Y plane (perpendicular to the z-axis) for the non-linear elements and interconnections. All these antenna exhibit wide band performance and medium gain patterns. One typical such antenna is a tapered slot (Vivaldi) antenna, which presents an exponentially tapered slot which can be etched on metallized dielectric substrates. Such antennas may provide 3 dB beam width for two frequency octaves at least.

There exist possibilities to use crossed-antennas structures in the same receiver for realizing balanced mixers. In each receiver, one antenna receives the s-mmw signal while another injects the radiation of local oscillator. In this case, the s-mmw radiation and the radiation of the local oscillator are cross-polarized that provides excellent RF/LO duplexing. The classical realization of s-mmw antennas is in micro-strip technology.

Figure 48A:
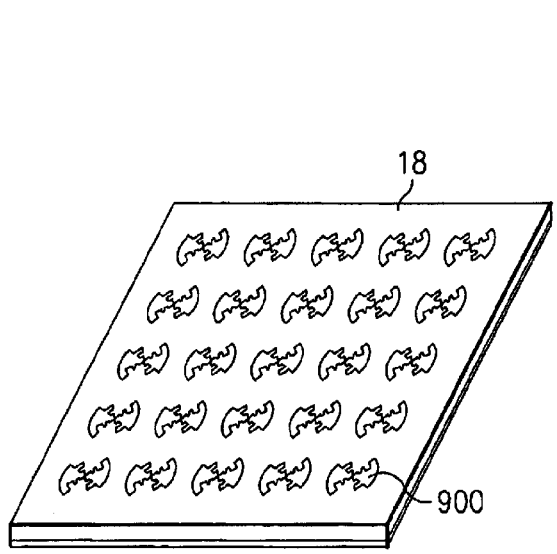
FIG. 48a is a view of an exemplary two-dimensional wide-band antenna coupled receiver array.
Figure 48B:
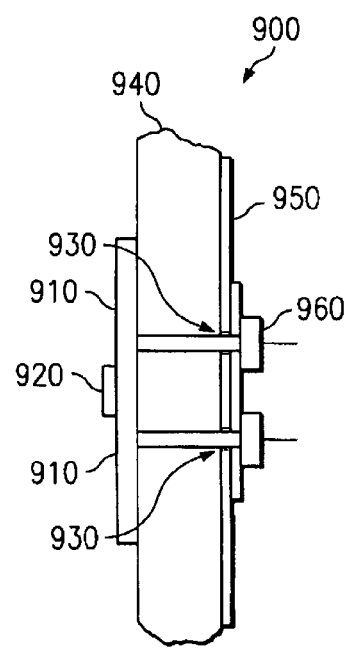
FIG. 48b is a detailed view of one element of a two-dimensional wide-band antenna coupled receiver array.

FIG. 48b zooms in one s-mmw sensitive element 900 of the multi-element receiver array 18. This receiver element comprises a wide-band antenna conductor pair 920, connected to each other by an antenna-coupled nonlinear element 910. The antenna conductor pair 920 is connected to the bias contacts 960 by means of the via pair 930 through the dielectric substrate 940. Metal layer 950 grounds the detector plane.

Figure 49A:
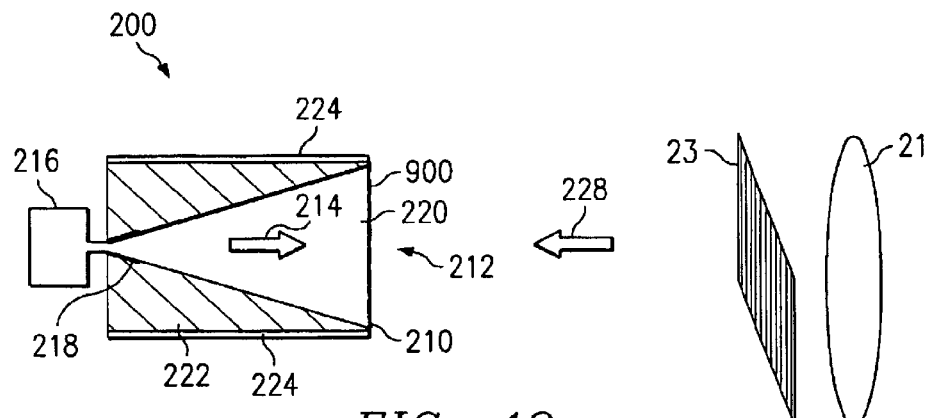
FIGS. 49a–49b illustrate a novel principle according to the invention to distribute the LO-signal to the multi-element receiver array.
Figure 49B:
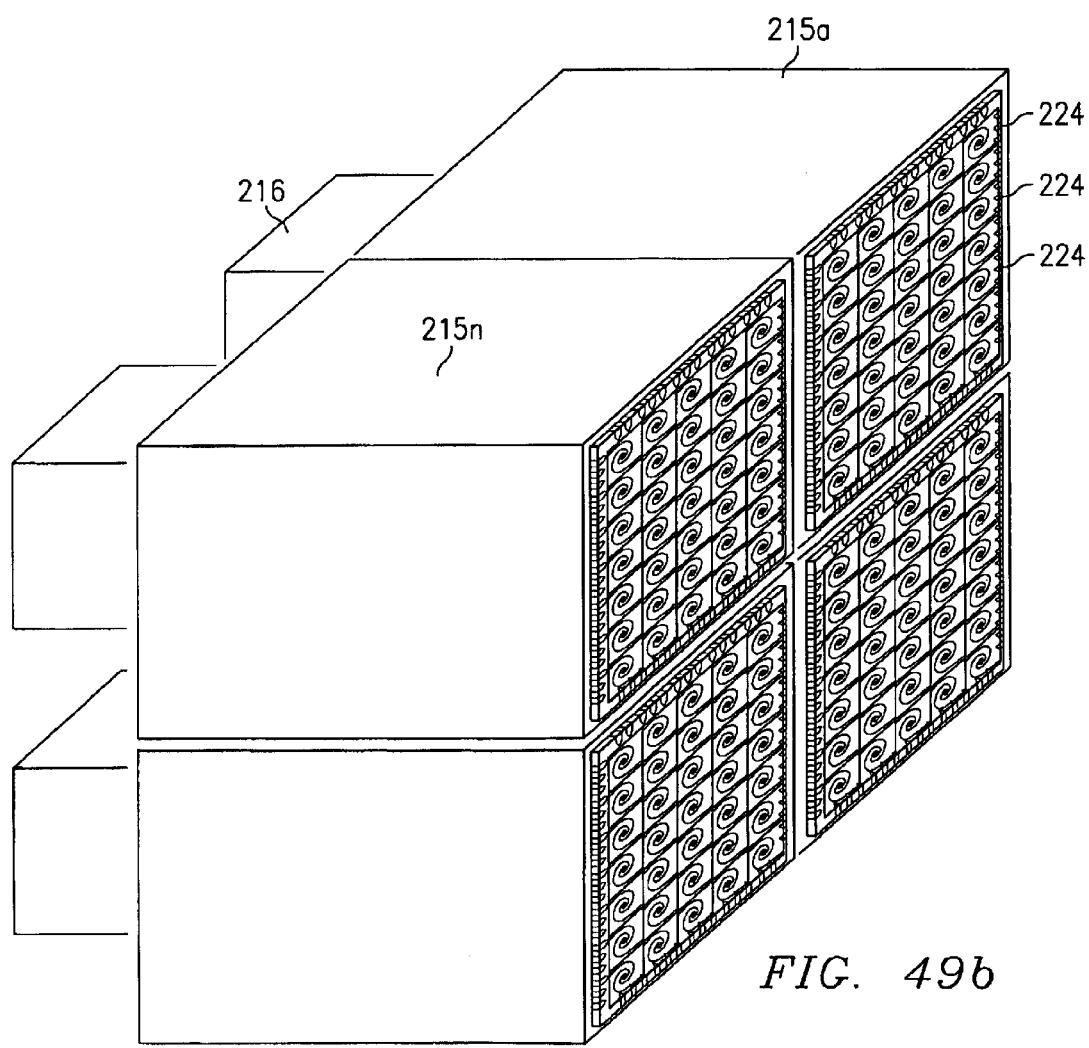

Another embodiment receiver 200 is presented in FIG. 49, which includes FIGS. 49a and 49b. FIG. 49a illustrates a compact wide-band receiver unit where pumping multiple mixers are pumped in a quasi-optical way. A two-dimensional array of integrated mixers is disposed on thin dielectric membrane 210. The membrane material may be either any soft dielectric material (e.g., MYLAR™, or others) or hard ones (e.g., DUROID™, or others) depending on the operating frequencies of the unit. The thickness of the membrane needs to be chosen such that substrate modes are not excited in the membrane. The number of mixer element needs to be limited in order to provide an appropriate topology for any biasing/output connections of the mixer elements located in the same plane.

Connection pads are provided at the edges of the membrane 210. The design allows the IF signals of the mixers to be immediately supplied to correspondent IF amplifiers (224) which are located outside the membrane plane but near the edges and in planes being perpendicular to the plane of the membrane. The latter permits to make multi-unit receiver arrays with high density of the receiver elements as illustrated in FIG. 49*b*. The membrane functions as a termination plane of an over-sized wave-guide structure 220, which is optimal for the propagation of the radiation 214 of wide-band LO 216. The LO radiation directing structure 218 may be provided by absorber 222, suppressing interference reflections.

Image radiation 228 impinges a thin penetrative membrane 210. Local oscillator (LO) radiation 214 is generated by s-mmw frequency sweeping source/isolator 216 and directed toward membrane 210 through a directive structure 218. The receiver array is disposed on a penetrative substrate 210 (without grounded metal plate). LO radiation 214 can be incident on the substrate 210 from direction being opposite to the direction of propagation of imaging radiation. This configuration makes the imaging system 200 more compact because one does not need any quasi-optical diplexing elements. The size of such unit 212 should not be overly extended since the bias and output IF signal leads 224 (FIG. 49*a*) should be able to output the signals from the array elements 212 without mutual electrical coupling.

The total mixer receiver array can be composed from a set of sub array units 215*a* ... 215*n* every of which has a limited number of receiver elements and is provided by individual LO source as shown in FIGS. 49*a* and 49*b*. The proposed geometry of the units allows all components of the heterodyning scheme (including the IF amplifiers) to be configured in a compact way while allowing the creation of as big an array as needed. The design allows providing wide band radiation, pumping the mixer elements and such pumping may be done in subharmonical regime. The mixers can also be operated in the homodyning mode if the radiation of the powerful LO is used both for pumping all the units of the array as well for illuminating the field of view of imaging system. This is achievable when the LO radiation is split in the appropriate way.

A multi-element receiving system of the s-mmw imaging system is intended for multi-element reception of the decomposed radiation. In the preferred embodiment, the radiation has been scattered by an observable object and further imaged by lens (or mirror) at the multiple elements of antenna receiving array of the system, with following optimal decoding of the received radiation. The receiving system generally comprises a multi-element antenna array, each element of which is able to receive the (decomposed) radiation, being scattered by a particular distinct point of observable object, and multi-channel image data acquisition block.

Due to the lens (see element 21 in FIG. 6), the elements jointly "look" at a complementary set of distinct points of the concealed object's surface that allows to produce partial and synthesized images of the object from correspondent multiple signals of the receiving array after their decoding. The image data acquisition block IDA (122 in FIG. 6) comprises a set of signal amplifying and processing (SAP) units (102.1, 102.2, ... in FIG. 6) each of which is individually connected to correspondent antenna of the receiving antenna array (see FIG. 6). The units are preferably the same.

In essence, every unit of IDA block is similar to a signal amplifying and processing (SAP) channel of a one-element communication or radar system (depending on encoding type for the radiation signals and imaging goals of the system), radiation carrier frequencies of which belong to s-mmw radiation spectrum. Almost as the SAP channels of communication systems, SAP units of the imaging system generally comprise of (a) a particular set of information demodulation blocks for extracting the encoded information from the signals and (b) a set of signal amplifying/ transforming (SAT) blocks which primarily amplify the antenna received signals and transform the signals such that information can be optimally extracted in the following demodulation blocks.

Generally a set of SAT blocks comprises selective s-mmw low-noise amplifiers, heterodyning mixer(s) for down-converting the signals to desired IF spectrum, some IF amplifiers and finally demodulator circuits for demodulation of carrier frequency of the signal after (or even without) being down-converted. In accordance with current s-mmw technology the units may have different realisations.

Figure 50C:
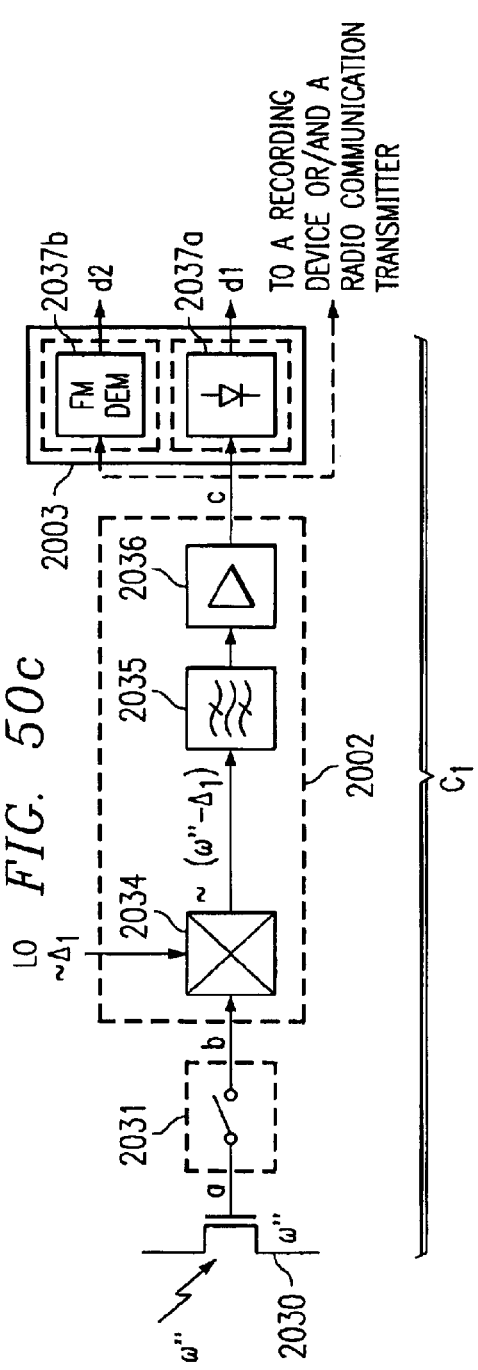

Some basic realizations of SAT units are presented in FIGS. 50*a–c*. Peculiarities of compositions of the SAT part of the receiving apparatus depend on the type of antenna element 2030 (FIGS. 50*a–e*), which serves as input port to correspondent SAT blocks. It may be a classic antenna element, scaled and suitably designed for operating at s-mmw frequency band. In this case, electrical signals, induced on the antenna by incident radiation are immediately supplied to the antenna following electrical circuits. As the signal exhibits s-mmw frequency spectrum range, performance of the first electrical circuits need to operate in the s-mmw frequency band.

State-of-the-art s-mmw monolithic low-noise amplifiers (LNA) operate over a wide frequency band (e.g., up to 10 GHz spectral width and even more), at least from considered lowest s-mmw limit even up to highest limit of F-band (e.g. up to 140 GHz). Moreover the current trend in the development of LNA shows a steady increase in the upper frequency limit of the LNA operation, which favors the further development of ultra wide band s-mmw imaging receiver circuits.

For the s-mmw spectrum bands where LNA's are available the classic realisation of SAT blocks may be successfully employed. Such a possible realisation is shown in FIG. 50*a*. This module $A_1$ comprises the following successive blocks: LNA block 2001 which comprises s-mmw band-pass filter 2032 and LNA 2033 respectively; the signal heterodyning block 2002 which includes mixer 2034 that down-converts the signal spectrum to IF range, IF band-pass filter 2035 and IF amplifier 2036; and finally the frequency carrier demodulator block 2003 which can comprise either some rectification non-linear element that performs envelop detection of down-converted signals 2037*a* if the signal was AM modulated or some frequency/phase discriminator 2037*b*, if the signal was FM modulated. In the latter case, the frequency $\Delta_1$ of the local oscillator (LO) pumping the mixer 2034 should be highly stabilized.

The SAT block may be supplied by PIN diode or MEMS switches being inserted in front of LNA block 2001. In this case, and if the SAT block ended by the rectification non-linear element (Schottky barrier diode, for example), one can successfully implement Dicke radiometer operation and correspondingly radiometric imaging. Currently, multi-element monolithic implementations of the SAT block are emergent: 32 parallel down-converter module, composed of GaAs monolithic microwave/millimeter wave integrated circuits (MMIC), demonstrates >40 dB RF-to-IF gain with averaged noise figure near 5.7 dB over a 10 GHz bandwidth centered at 92 GHz. (see SPIE Proceedings Vol. 3378, pp 46–56 (1998), incorporated herein by reference).

The array of MMIC modules is able to provide both multi-element Dicke operation radiometric imaging and gain tracking within +/−2.5 dB and phase tracking within +/−18 degrees between the whole set of receiver channels. As a consequence, this module allows implementing vector measurements of the receiving signals in case suitable LO signals (being phase locked with receiving signals), are available. Such MMIC modules may be successfully used in s-mmw imaging receiver apparatus in case of doublet encoding of object illuminating radiation as any other modules realised in accordance with the block-scheme in FIG. 50a.

As it was discussed above, any amplification and-or down-conversion of doublet signal components does not disturb their (modulated or stabilized) frequency difference. Correspondent beat signals (i.e. the frequency differences) of the doublet components will be produced at the output of rectification element 2037a. The consecutive amplification and processing of multiple beat signals will be discussed below.

The next possible realisation of SAT block, based on usage of s-mmw LNA, is shown in FIG. 50b. In this case, the down-conversion step of s-mmmw signals is skipped. Being directly amplified in the multi-stage LNA, the antenna received RF signals are immediately rectified by non-linear element 2037a, which is electrically connected to the output of the final LNA stage. Such SAT block realisation has real advantages due to total absence of any power LO required in any heterodyning mixing circuit. Eliminating the LO, a main heat source of the SAT block, drastically reduces the temperature rises and heat removal problem of circuits elements. Hence the eminent thermal dissipation problem for any RF blocks including the s-mmw LO, is non-existing in LO-free RF-blocks. The latter is important because it allows essentially increasing the circuit density and enhancing their reliability.

Direct amplification and detection (DAD) receivers are very limited in their usage for communication goals when traditional methods for modulation of carrier frequency are used because actually in that case only AM modulation may be really employed. Situation in the preferred embodiment of doublet encoding of the radiation carrier frequencies essentially changes. In this case the frequencies of beat signals generated by the rectification diode 2037a, will be strictly ordered and spread over the whole desirable range (up to 1–3 GHz and higher). These beat signals may be modulated by any known AM or FM modulation method or any of their combinations, as it was discussed above, thereby their demodulation may be effectively realised in low power circuits, already extensively developed for operating in the spectral ranges of doublet beat signals. Thereby such demodulation circuits may be only digitally implemented. One of the advantages of doublet modulation of carrier frequency is the possibility to vary absolute values of the carrier frequencies of doublet radiation components while saving modulation features of their difference. Quick carrier frequency hopping is urgently needed for increasing safety in communication applications because it creates great difficulties to find and recognize the hopping carrier frequencies of the radiation and to suitably demodulate the radiation by traditional communications means.

Finally DAD realisation of SAT block is ideally suited for MMIC implementation. State-of-the art W-band s-mmw receiving arrays consisting of 1040 integrated direct amplification and detection receiving channels has been developed. See SPIE Proceedings Vol.3378, pp.57–62, 1998, incorporated herein by reference. Every channel comprises a highly integrated MMIC chip receiver. The MMIC chip consists of wide band, low noise, high gain, 0.1 $\mu$m InGaAs multi-stage HEMT amplifier followed by a integrated Schottky barrier diode detector. To realize the Dicke mode operation of the chip, balanced switching LNA was integrated as a first amplifying stage of the chip. This is schematically shown as a switch element 2031 in FIG. 50b.

In the chip the Dicke mode operation is intended to reduce the gain fluctuations and "1/f" noise of the diode. Integration of the LNA, diode and switch at the same chip allowed dramatically increasing a density of space packaging of receiving apparatus channels, reducing their complexity and cost. Using the (1024) multi-element receiver array, a passive mmw camera, capable of generating real time images of the scene under observation at a frame rate of 17 Hz, similar video cameras, was developed. The array is built in modular form. The front modules providing signal amplification/demodulation comprise four MMIC receiver chips, a four-element antenna array, current regulator and video-amplifiers. Three signal processing modules follow. These modules typically comprise hybrid circuitry for further signal amplification, filtering, integration and digital control and digital signal processing.

In the preferred embodiment, the camera is based on quasi-optical imaging through 18" plastic lenses. In the preferred embodiment, the central frequency of the passive mmw camera system is 89 GHz, its operational bandwidth is 19 GHz and its resolvable temperature equal to 2K at the lens output. The camera is intended for outdoor imaging and the camera temperature resolution allows obtaining high quality and contrast images of observable outdoor scenes. The latter is achievable due to high temperature contrast between cold sky (T=100K) and Wart earth (T=300K). In case of indoor detection of contraband carried by individuals on their body beneath their clothes, the temperature contrast of the scene shrinks to 5–15 K in the best case. Hence possibilities of passive indoor imaging are very limited for the current camera technology.

However, the performance (e.g. the quality and contrast of images) of such camera can be substantially enhanced by simply substituting the processing modules of the camera with specially designed processing modules (even based on hybrid electronics) adapted to the modulations of decomposed radiation, actively illuminating the scene. Thereby the averaged power level of object illuminating radiation, required for contrast imaging by the camera in active imaging mode, will be essentially lower than the averaged power level of radiation received by the camera from thermal environmental when operating in the original passive imaging mode. The signal processing modules needed for realising the adaptation as well as the adaptation of the SAT blocks, being suitable for the proposed imaging/communication receiving apparatus, will be discussed below.

When the proposed doublet principle of encoding the s-mmw radiation is used, the DAD MMIC multi-element receiver array may be easily adapted for s-mmw communications applications. In this case, a compact multi-element communication receiver may be realised, every element of which will be able to receive a plurality of communications signals, each of them propagating within a distinct narrow solid angle. This may be achieved by attaching the antenna array of the DAD MMIC receiving array to some immersion lens at its focal plane. Such construction design was successfully employed for realisation of multi-element radar head when every receiving element of the radar "looks" within particular narrow solid angle, direction of which depends on the position of the antenna element at the focal plane. See, C. J. Alder et al., "Microwave and millimetre-wave staring array technology," Proc. IEEH, vol.138, pp.253–257, June 1991, incorporated herein by reference.

Multiple antenna elements of such communication receiver will complementarily and independently of each other cover the whole field of view. The latter may be very useful when several transmitting communication stations, spread over different locations, have to be simultaneously controlled and, at the same time, subjected to intensive radiation interferences coming from different directions. Such situation is typical, for example, for indoor wireless inter-computer communication when multi-path propagation of the transmitted radiation takes place due to multiple reflections between room walls. Adaptively designed processing modules as it was discussed above, will be able to distinctly decode correspondent AM/FM modulated beat signals, produced by the rectifying detector element at the back end of corresponding multi-stage LNA in every DAD MMIC chip of the receiver independently.

The physical size of such wide-band multi-beam lens-coupled receiver may be quite small because reasonable sizes of any antenna directly disposed at the substrate lens, made from a material with refractive index n, will approximately shrink n times in size compared to free-space antennas. In the preferred embodiment, the substrate lens is made from materials transparent in the s-mmw spectrum and having a large refractive index such as geranium (n=4), silicon (n=3.40), GaAs (n=3.30), fused quartz (n=1.95) and ZnSe (n=2.40). The biggest linear size of a 10×10 antenna element receiver may range from less than 1 cm up to 3 cm depending of the exploited antenna type and the lens material refractive index. Really, possibilities exist to create a multi-channel wide-band s-mmw transceiver, based on the principle of doublet modulation of carrier radiation and multi-beam principle of receiving the radiation, which will have low cost, low power reliable performance based on MMIC technology.

Figure 50D:
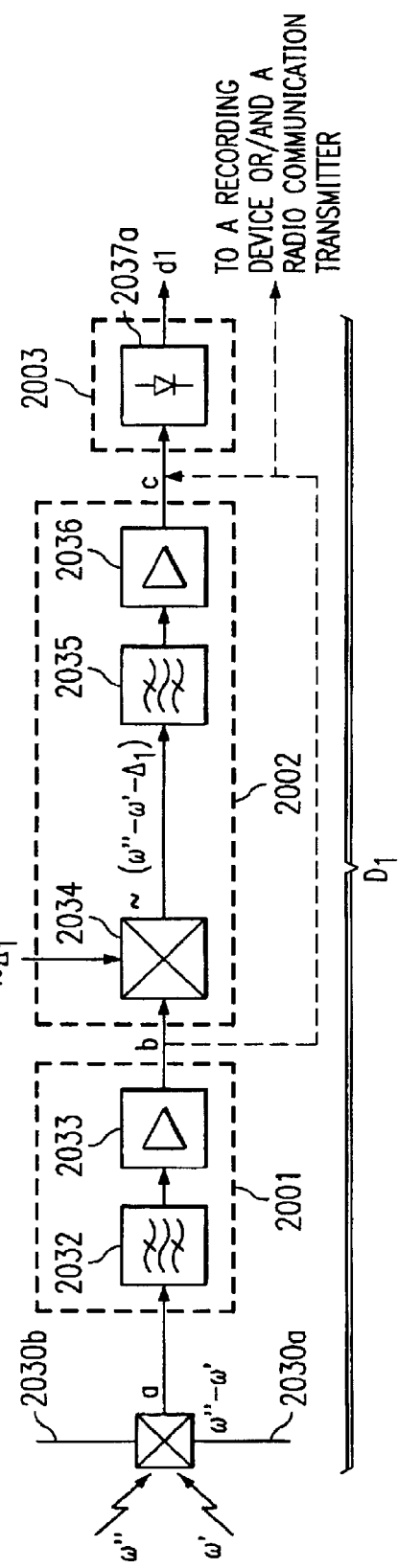

Classic block-diagram of a s-mmw SAT module, which can be developed for operation in any part of s-mmw range (from mmw up to terahertz bands) is shown as module D1 in FIG. 50d. Such module is, as a rule, fabricated in wave-guide technology. Standard wave-guide antenna 2030 in FIG. 50d for s-mmw radiation is a machined conical horn antenna. Two antenna horn designs are very typical: the corrugated horn antenna (40% of usable bandwidth) and dual (Porter) mode (near 10% of usable bandwidth) antenna. Both antenna horns exhibit rotationally symmetric antenna patterns, high gain (up to 30 dB) and low cross-polarization levels (below −30 dB). The higher frequency limit for the corrugated horn is 300 GHz and for dual mode horn is near 500 GHz. The frequency limitation is primarily due to difficulties in manufacturing such horns.

For still higher frequencies (up to 900 GHz) simpler pyramidal or conical horns without complicated construction may be applied. Machined design is possible for travelling-wave corner-cube construction. The horn has an open construction, which may be loaded by a whisker diode. In this case such construction will be able to perform signal heterodyning or envelop detection functions. The corner-cube antenna exhibits relatively high level side-lobes but are the only available waveguide based receivers for radiation above 1000 GHz.

In the SAT module $C_1$ of FIG. 50c, the signal received by antenna 2031 is immediately down-converted up to IF range in mixer 2034, which is pumped by a local oscillator signal having a frequency $\Delta_1$. (PIN diode switch 2030 may be additionally inserted in front of the mixer 2034 if the module C1 will be used for passive radiometric imaging as well.) The module $C_1$ of FIG. 50c can be ended by carrier demodulation block 2037a or 2037b discussed above in connection with SAT module A1 of FIG. 50a.

State-of-the-art s-mmw technology permits to use monolithic (or hybrid) antenna-coupled non-linear elements immediately in front of SAT module. The integrated receivers are easier to manufacture, more reliable, less expensive than waveguide based receiving elements and allow creating fully monolithic multi-element receiver arrays. They are an alternative solution for receiving mmw radiation and a practical solution for s-mmw (e.g., 300 GHz–3 THz) and even higher frequency bands up to the optical range.

Many novel antennas were developed such as dual-slot, log-periodic and spiral antennas, integrated horn antennas, which can be disposed on different kind of substrates ranging from microstrip substrates up to hemispherical lens substrates.

The integrated receiver preferably comprises a single s-mmw antenna, a non-linear element integrally coupled with the antenna, and the matching network. The receiver is able to mix the signal radiation $\omega'$ and pumping radiation $\omega''$ of the local oscillator delivered to the mixer in quasi-optical way. The resultant IF signal is immediately produced by antenna coupled non-linear element (which can be e.g. a Schottky barrier diode, or MOM diode, or others).

The LF-signal, after being filtered by a band-passing matching circuits, is amplified by IF amplifier circuit 2001 of FIG. 50d, which schematically comprises IF band-pass filter 2032 and amplifier 2033 following the receiver 2030a. The output of the IF amplifier may be directly connected with carrier demodulators blocks 2037a or 2037b, which are the final stages for the SAT module. All discussed SAT modules (A1–D1 . . . ) may be provided by additional down-converting block (which is shown only in FIG. 50a as block 2002). In this case the resultant sum frequency ($\omega'$+ $\Delta_1$) of the first LO signal $\omega'$ and the second LO signal $\Delta_1$ have to be chosen in such way that the double (or multiple) down-converted signals exhibit spectral location coinciding with operating frequency range of the following IF amplifier (2035 and 2036 amplifying chain 2002 of FIG. 50d). Multiple down-conversion of a signal in super-heterodyning modules is known to lead to better performing systems: e.g. to achieve simultaneously higher amplification gain and stability of the electrical circuits, better frequency selectivity and so on).

In the last discussed SAT-module E1 of FIG. 50e, the antenna-coupled non-linear element (in monolithic as well as in hybrid technology) may be used as rectifying elements. In the SAT module $E_1$ the integral receiver element 2030 may be immediately followed by video amplifiers 2001. In case of traditional LF AM approaches for modulating a radiation carrier, 1/f noise of the non-linear element 2030 will essentially decrease S/N ratio of the signals after their demodulation by such element. S/N ratio may be essentially enhanced if proposed doublet modulation principle is used because the frequency band of beat signals, which will be produced in this case by such receiver element 2030 may be located in IF range depending on a realisation of the doublet radiation source used.

The SAT module $E_1$ may need to be modified. For example the receiver element 2030 may be followed by IF amplifier (like 2034 of FIG. 50*d*) and even down-converting block (like 2001 of FIG. 50*d*) depending on frequency features of applied doublet modulation of the radiation. The latter blocks are able to essentially enhance signal-to-noise and extends the bandwidth of the SAT module $E_1$.

The receiving apparatus has to be supplied by additional signal demodulating modules if the doublet modulation principle is applied for encoding the s-mmw radiation. Such modules may be realised in accordance with the block-schemes being shown in FIGS. 51*a–b*. The module is intended for demodulating the beat signals, which are produced by rectification elements 2037*a* or 2037*b* in the SAT modules A1–E1 of FIG. 50. The block-diagram of the module, which is intended for processing the radiation being decomposed over multiplet(s) (or doublets) exhibiting distinct, constant (or even phase-locked) frequency shifts of its radiation components, is shown in FIG. 51*a*.

The spectra of the correspondent beat signals were discussed before in connection with FIGS. 40–42. The module comprises a band-pass amplifier block 2004, selecting and amplifying the beat signals of a particular multiplet or a whole set of beat signals produced by all radiation multiplets, which have to be processed. The block 2004 of module F2 also suppresses any inter-modulation products of the interference type discussed above in connection with FIG. 42*b*. Heterodyning block 2005 of F2, following the amplifier block 2004 is pumped by the signal, produced by doublet radiation source at output of the source mixer 846 in FIG. 14*a* or FIG. 14*b* (depending on the type of source realisation).

Spectrum of such signal is preferential in IF spectral range or even in lower spectral ranges and, as a consequence, may be delivered from the radiation source to the receiving apparatus through flexible coax cable. The latter leads to a non-expensive realisation of the imaging system because one does not require any waveguide couplers and other waveguide elements for delivering reference signals.

Before pumping the mixer 2041 of F2, the source beat signal is primarily amplified. It was discussed above that the signal difference between doublet components are either frequency stabilised in accordance with scheme of FIG. 14*a* or even phase-locked by steady low phase-noise reference signal of external or internal oscillator, (which, in turn, may be stabilized, for example by high Q-value quartz crystal). The phase-locked doublets of the multiplet radiation is of great interest because along their propagation path from the multiplet radiation source up to the receiver array multiple scattering and reflections will not change the original phase relationship between the phase locked doublet components (e.g., they propagate identically). The phase relationship between them will not be distorted while they are amplified, down-converted and self-mixed in the SAT modules. In other words the beat signals produced by rectification elements of the discussed SAT modules will be strictly ordered in accordance with their frequency (for the radiation produced by source of FIG. 14*a*) and moreover every beat signal will be phase locked by correspondent reference signal produced by frequency stabilised oscillator 858 in FIG. 14*b*.

If beat signals of this type of illumination radiation produced by demodulator 2037*a* of SAT modules A1–E1 and amplified by the amplification block 2004 of F2 will be down-converted in the mixer 2041, which is pumped by amplified original beat signal produced by the radiation source mixer 846, all double down-converted signals at output of the mixer 2041 of module F2 will be phase-locked by the stabilized oscillator 858 and reflect its phase noise characteristics.

The latter may be effectively exploited for speckle-free imaging, which can be realised even if the observable objects (having any kind of surface roughness) are illuminated by spatially coherent multiplet radiation as it was discussed above. The amplitudes of the beat signals at output of block 2003 of SAT modules A1–E1 will be proportional to the intensity (but not to the amplitude as it takes place for traditional active imaging) of radiation scattered by those small parts of the observable object at which the receiver element 30 of the considered receiving channel looks at.

Phase distortions in the radiation that appear due to random structure of the object's surface and which usually cause speckle structures in images in case of usual active coherent imaging, will be self-destroyed in the considered receiving apparatus. Any doublet images will exhibit quality of spatially non-coherent images even if spatial coherence of the object illuminating radiation will not be destroyed at all before interacting with the object. In other words, the quality of images obtained by doublet illumination is the same with and without a spatially coherence destroying diffuser placed in the imaging system.

Moreover in the case of using the diffuser precisely extending the spectrum of the illuminating radiation (for example, the array of modulated antenna-coupled non-linear elements) any particular angle of radiation incidence on the object surface may be distinctly revealed thereby any angular distinct image produced by the partial radiation being incident on the surface with particular resolved angle will exhibit quality of spatially-non-coherent image (without any speckle structure).

Absolutely novel and unique imaging possibilities become acceptable when the multiple decomposed radiation with phase-locked paired radiation components will be used for illuminating the scene and the eventually concealed objects. It is important to emphasize here that due to the fact that doublet radiation images will be equivalent to images obtained while illuminating an observable object by spatially non-coherent radiation (one possible realisation of such kind of imaging is the a well-known passive radiometric imaging), all methods of digital processing which lead to enhancing the quality and resolution, may be applied. In particular, the digital methods of super-resolution, based on obtaining over-sampled images, which are subjected to further image processing to overcome diffraction limits in spatial resolution of the images being only provided by a limited aperture lens used, may be effectively employed here.

If the imaging radiation comprising doublet components, is not subjected to additional spectral broadening (it may be performed by only diffusers like the array of antenna-coupled modulated non-linear elements spectrum of their beat signals (differences) exhibits narrow-band form (see FIG. 41*a*)). Moreover the resultant second order beat signal at the output of mixer 2041 of module F2 will be down-converted strictly to zero value (to offset of the spectral axes) with accuracy of its spectral location being equivalent to accuracy of stabilization of the reference signal of stabilized oscillator 858 in the doublet radiation source in FIG. 14b (within the reference signal bandwidth). In this case the final amplifier 2042 of the processing module following mixer 2041 and band pass filter 2062 of F2 has to be a LF amplifier with extremely narrow bandwidth (for example in some implementations less than 1 Hz).

All other signals will be effectively rejected. In considered case the output k of module F2 in FIG. 51a should be directly connected to the multiplexer 130 of FIG. 6. If the spatially non-coherent imaging system being based on ordered angular decomposition of the object illuminating radiation is employed, then as it was discussed the spectrum of the imaging beat signals, being produced by block 2037a of any of the SAT blocks A1–E1 will exhibit precisely extended spectrum. Thereby the fine structures will be strictly ordered in such way that the spectral shift of any spectral component of the spectrum relative to the primary beat frequency $\omega_{s,24,1}$—without any loss of generality one referred as an example to doublet n=1 of multiplet m=24, the beat signal frequency of which is equal to the static value $\omega_{s,24,1}$—will be precisely equal to the modulation frequency of a signals, which modulates a particular scattering element of the diffuser. In other words, information parts of extended spectrum 565, 563, 570, 568 in FIG. 41 was shown to be some additive set of spectral components every of which is responsible for radiation scattered by particular diffuser element and having a spectral component precisely shifted from frequency $\omega_{s,24,1}$ with a value of frequency of the element modulating signal $\Delta\omega_1$. (Generally the number of independent spectral components in the information spectrum structures 565, or 570 an so on is equal to the number of the diffuser scattering elements). After second down-conversion of the signal at block 2041 of module F2, the spectral components of the information spectrum part 565, 570, . . . will be shifted relative to offset to values being exactly equal to modulating frequencies of diffuser elements $\Delta\omega_{1el}$. In this case if only angular information spectrum part is of interest (565,563 or 570,568) the filter 2062 or 2063 have to be band-pass and to exhibit $\Delta\omega_0$ (see 565,570) bandwidth (being equal to the bandwidth of the information spectrum parts) and centred around the centre frequency of the diffuser modulating signals $\Delta\omega_1$.

The module F2 may be adapted for processing any part of extended spectrum and any their combination depending on image signal processing methods. It needs to be emphasized that the spectral position of all components of the extended spectrum is precisely defined both after their first down conversion (in 2034 blocks of the SAT modules) and after their second down-conversion (2041 of F2); it means that the electrical circuits of the modules may have sharply frequency selective characteristics and as narrow as it is needed. Because the reference beat signals pumping the mixer 2041 of F2 are not s-mmw signals they may be delivered from the doublet radiation sources to the receiving apparatus via usual flexible coax cables that essentially simplifies the apparatus because there no any necessary in any waveguide couplers for splitting the s-mmw radiation to obtain reference signals.

In addition, the block F2 is able to precisely process any doublet beat signal of any other multiplet (or doublet) of the decomposed radiation. Really in considered case the mixer 2041 of F2 is pumped with stabilized (or even phase locked) beat signal of some particular doublet components exhibiting particular frequency shift $\omega_{s,24,1}$. As a result in offset point of the spectral axis, only those particular imaging beat signals, which are precisely located around the frequency $\omega_{s,24,1}$ are down-converted. If the mixer will be pumped with beat frequency of any doublet component of the multiplet, the imaging fine spectrum structure of namely the last doublet components will be precisely down-converted to the offset. Moreover the spectral components being responsible for particular scattering element of the diffuser array will be shifted relative to the offset at the same magnitude for any beat signals after their second down-conversion (or more exactly, their homodyning). This fact may be effectively exploited in following LF sections of the processing module. The value of spectral density of every the double down-converted spectral components distinctly reflect the scattering properties of the object surface for different angles of incidence, polarization and carrier frequency. All these values may be distinctly determined in synchronous detectors, whose reference signals will be supplied from the correspondent oscillators of the diffuser modulating signals. Whole set of the modulating signals may be switched on to the reference input of the synchronous detector step by step sequentially in time. In this case not only quadrature value but in-phase and co-phase features of the signal, responsible for the radiation scattered by the particular diffuser element and then, in turn, by the particular point of the object surface may be determined with very high accuracy and sensitivity.

Figure 52B:
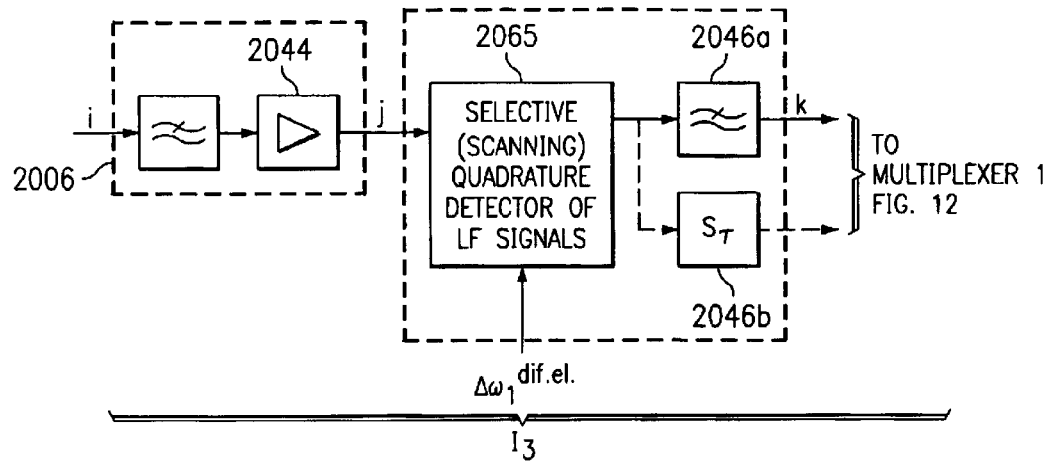
Figure 52C:
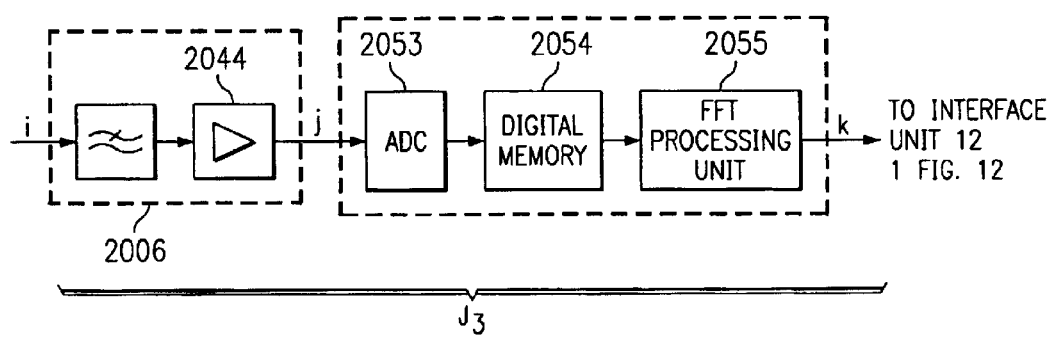

The signal features may be determined in a LF processing unit of FIG. 52c being fully digital. Such processing unit contains analog-digital converter (ADC) 2053 of block J3, which is intended for properly sampling the temporal signal being produced at the output h of the module F2 (or any other module which is able to finally produce the signal containing needed information and which can be sampled by ADC). In front of ADC may be embedded some LF amplifier 2006 of block J3 for additional amplification of sampled signal. The digital samples of the signal are sent to digital memory 2054 of J3 ADC and then are processed by processing unit 2055 of J3 performing the complex Fourier transformation (for example, the unit 2055 of J3 may be some fast DSP processor). It is well-known that all spectral features of the sampled signal (quadrature, in-phase, and co-phase values of all signal spectral components) maybe digitally calculated thereby the spectral resolution of the components will be defined by the time duration of the signal sampling. Thereby the number of the points of the samples sequence have to be enough to satisfy the Nyquist's theorem for optimal signal sampling.

The simplest LF processing module H3 being an amplitude detector is shown in FIG. 52a. This module may be used for extracting the sum of values of spectral density of all components belonging to an electrical signal including the signal produced by and appearing at output h the block F2. In this LF processing module H3 signals are first amplified by wide-band amplifier 2044 of H3, and further rectified by element 2045 of H3. Then the signal is filtered by low-frequency narrow-band filter 2046 of H3 for rejecting all inter-modulation products of the signal. The resultant output signal of H3 module provided at output k will be equal to sum of spectral densities of all spectral components of considered information parts of the decomposed spectrum 563 and 565 and so on. The bandwidth of the filter 2046a (or equivalently the time of signal integration by integration circuits 2046b) should be properly chosen. Namely the bandwidth of the filter 2046 of H3 needs to be at least smaller than smallest frequency difference between two consecutive modulating frequencies of diffuser array. This preference is analogous of the similar requirement on the integration time of an optical detector. The condition means that inter-modulation products, exhibiting interference nature, need to be deleted in the detecting signal. In optics the condition is automatically satisfied because optical detector exhibit as a rule relatively very long integration times due to detectors physical nature.

The same condition needs to be satisfied for low-frequency band filter 2046a of block I3, following the sweeping synchronous detector block 2065 of I3. For digital processing the condition is automatically fulfilled as a result of Fast Fourier processing (FFT) due to weighting nature of FFT.

If the used multiplet radiation exhibits FM modulation of doublet beat signals the module G2 of FIG. 51b may be used. This module only differs from the module F2 by FM demodulation block 2061 instead of mixer 2041 of block F2. The block 2061 of G2 may be a frequency or/and phase demodulator being able to operate in frequency band of the correspondent SAT module (A1–E1). This FM modulation of the radiation is much more attractive in communication applications. In this case the LF processing module may be absent at all or essentially changed in comparison with what was considered above.

Finally all the above discussions show that the receiving apparatus for imaging or communicating applications with s-mmw encoded radiation, may be easily adapted to passive imaging without any additional expenses. Really any considered SAT module (probably except D1 due to its low sensitivity) may be very effectively used for amplification of signals of passive imaging system if in front of them the switch 2031 is used. In this case the LF signals produced by the SAT A1–D1 may be adaptively processed by any of the considered LF processing schemes or any another designed LF processing schemes suitable for particular modulation signals by switches 2031.

Figure 53A:
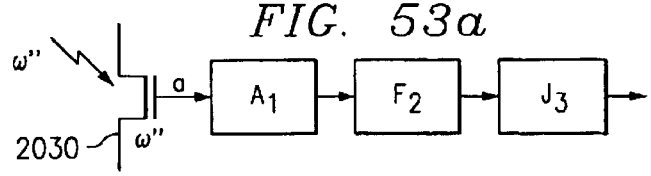
FIGS. 53a–53d are block diagrams representing possible configurations for s-mmw receiver apparatus for imaging or communication systems.
Figure 53B:
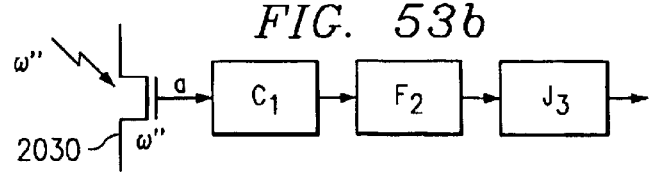
Figure 53C:
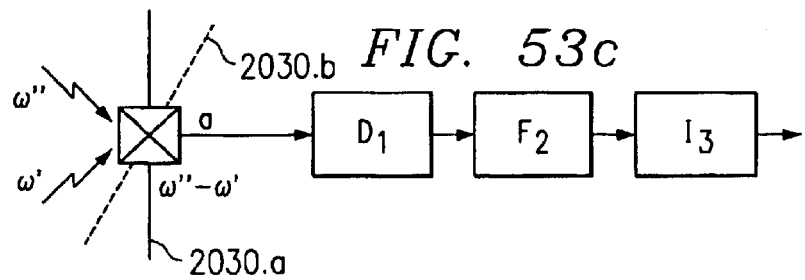
Figure 53D:
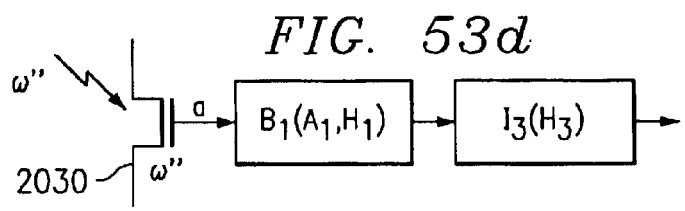

Such situation is illustrated by FIG. 53d.

Finally some possible block-schemes of a single channel of the receiving multi-channel apparatus being suitable for amplification and demodulation of decoded radiation (including the above discussed) are shown in FIGS. 53a–c. Suitable demodulation schemes may be adaptively designed for any kind of encoding (decomposition) the s-mmw radiation, starting from the simple AM modulation methods up to the more preferred doublet modulation methods, featuring much higher sensitivity, larger and denser information capacity, simple and cheap receiving apparatus for imaging and communication applications in the s-mmw frequency band.

As to additional possibilities of quasi-optical imaging based on a usage of multi-element receiving array which is able to receive multi-frequency wide-band signals from multiple independent directions, it is needed to emphasize that three-dimensional imaging may be realized. The first realization of the three-dimensional imaging is based on the fact that the all aforesaid mixers, being intended for down-converting the s-mmw radiation, permits to make vector measurements of received signals (to sense both amplitude and phase changes of the radiation). To do such measurements the local oscillator signal has to be phase-locked by the emitting radiation oscillator (or both of them have to be phase-locked by harmonics of highly stabilized reference oscillator which can exhibit essentially lower frequency). The same may be done even if only beat signal between the s-mmw radiation and LO radiation will be primarily phase-locked by the reference signal of the stabilized oscillator. In the case of the stabilization of the said beat signal, any changes of phases of s-mmw radiation wave-front, after ones multiple reflection and propagation through field of view of the imaging system, will be precisely indicated by the same phase changes in the beat signal produced by the receiving mixer (for example by any of the said integral receiving mixers). At last, any s-mmw homodyning technique may be effectively used for vector measurements. Here the down-converting mixer has to be pumped by the same s-mmw radiation signal which is used for illumination the field of view. In the last case the s-mmw radiation may be appropriately split into mixer pumping part and illuminating part, which will be further mixed at the mixer of the receiving channel. It is well-known fact the complex Fourier transform of a vector signal response versus s-mmw frequency can be transformed in a temporal response function. As the speed of s-mmw radiation propagation is known, the time response may be translated into distances along the propagation path up to radiation reflecting obstacles. Any element of the receiving array is responsible for particular distinct direction. As a consequence wide-band quasi-optical vector imaging by means of multi-element receiving array allows realizing a three-dimensional image of the observable scene. For contraband detection goals, both the said three-dimensional multi-element imaging system and a single receiver element system may be effectively used. Hand-held portable frequency scanning units, with embedded processing means to provide vector processing a contraband reflected radiation may be effectively used in the cases when it is possible to make mechanical scanning the unit immediately near the clothes of an observable individual (as closely as 1–2 cm up to clothes surfaces). The unit may be very compact because one does not need in quasi-optical lens at all for said operation mode. The depth resolution in the observable scene is reciprocal to frequency range of the object probing radiation. In this case higher s-mmw frequency ranges are preferable for achieving more precise distance resolution.

Any vector analyzer apparatus is quite expensive and complicated for properly operating in wide-band ranges.

The embodiment of the invention proposing much more simple and cheap realization of three-dimensional imaging based on usage of Fresnel zone lens and doublet multi-frequency realization will be discussed below.

Generally quasi-optical refractive lenses, used as a focussing element 21 for multi-frequency imaging need good imaging properties over a large field of view (+/−30 degrees) and preferable quasi-identical properties within the whole frequency band of imaging system. It is known that for a refractive lens the best focus, as a rule, lies on a curved surface. This fact may be partially corrected by disposing every element of receiving array (or a subarray of receiving elements) individually on the same plane, whereby the planes tangentially coincide with the specified curve surface for optimal focussing. In general, to eliminate or minimize off-axis phase aberrations of the imaging lens 14, such lens design need to be subjected to a fully analytical treatment for optimizing a multi-component optical focussing system for multi-frequency radiation, at least, the possibilities to vary profiles for every said lens component and their mutual locations. It is obvious that the material of the different lens components need to have the same refractive index and absorption.

Reflecting mirrors, which can also be used as the focussing element, may exhibit quasi-identical imaging properties over wide-frequency band. However, the aperture diameter of any focussing element for a practical imaging system, is relatively small and for longer s-mmw wavelengths the diameter may be not larger than only a few hundred wavelengths. As the imaging spot size is proportional to the multiplication product of the focussing element f/D ratio (where f is the focus length and D is the aperture diameter) and the operation wavelength $\lambda$, the best spatial resolution may be achieved at higher frequencies of s-mmw. Additionally for symmetrically reflecting mirrors the blockage losses of the imaging radiation may be to high for longer s-mmw wavelengths.

Figure 54:
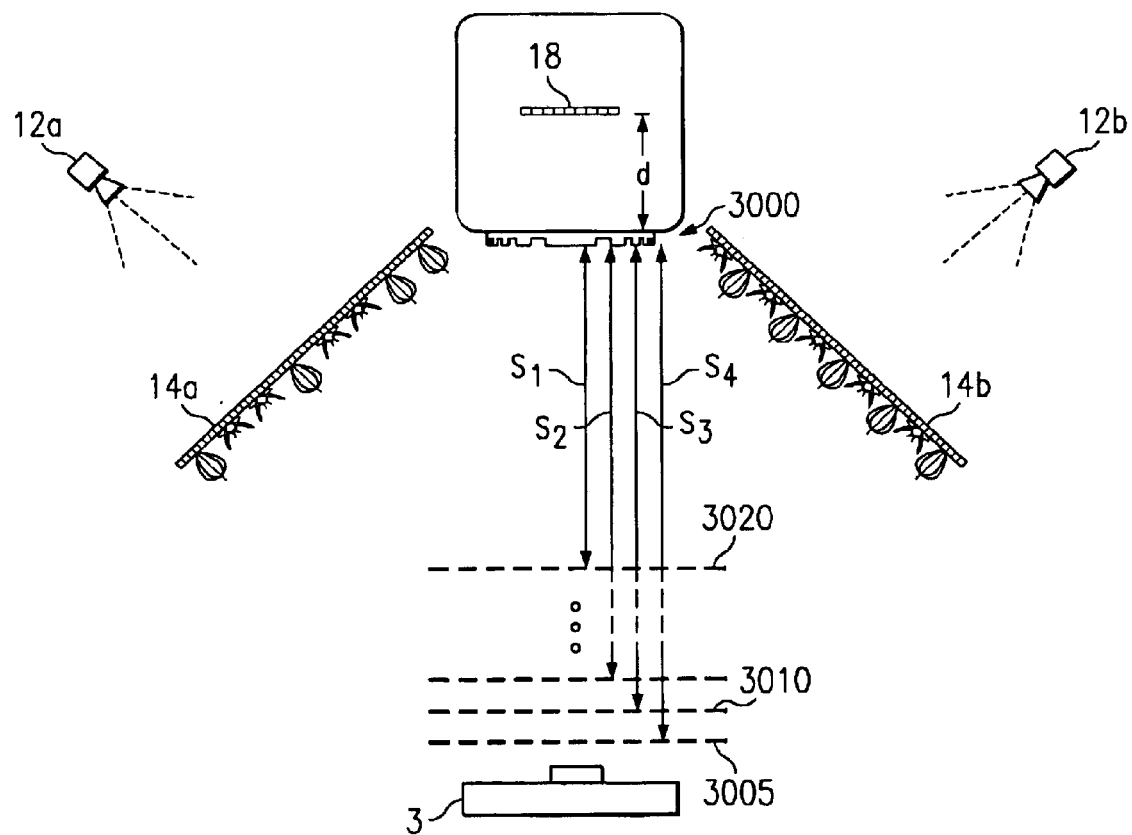
FIG. 54 is schematic diagram showing the usage of Fresnel lenses for 3D scanning depth of focus.

For s-mmw imaging diffractive focussing elements may be of great interest. Typical class of such focussing element is Fresnel zone plate lens. It is well-known fact that the resulting focal length of such lens depends on the wavelength of imaging radiation. When the distance d in FIG. 54 between the Fresnel lens 3000 and the receiving array is kept constant, then the planes 3005, 3010, . . . 3020 of the observable scene (perpendicular to the lens axis) which can be focussed at the receiving elements 18, will vary with the wavelength of imaging radiation (s1, s2, s3, . . . ). These wavelength dependent distances from the planes towards the lens are indicated in the exemplary FIG. 54 by the indices S1, . . . S4 for four distinct wavelengths. It is of great of interest for s-mmw frequency range where the frequency of s-mmw sources may be varied over the 20 per cent and more of its central frequency. But said imaging possibilities had no practical meaning up to now, because the used s-mmw source radiation exhibited high coherence that led to speckled imaging with very bad visual quality. The situation may be totally changed if spatial coherence of the s-mmw source (12a, 12b of FIG. 54) radiation will be previously destroyed by any of the diffusers (14a, 14b of FIG. 54) of preferred embodiments of this invention, and only after the destruction of the radiation's spatial coherence, the radiation will be redirected towards the observable scene 16. In this case, multiple enhanced visual quality images of distinct planes of the scene at different distances S1,S2,S3, . . . from the Fresnel lens 3000 may be obtained just by sweeping the frequency of s-mmw source 12. In other words, a whole volume of observable scene will be scanned by sequentially imaging the different cross-section planes of the scene and this can be performed in real time.

Furthermore multiple images of the different planes may be obtained with the same visual quality without using any using diffuser if the object illumination radiation being under frequency sweeping comprises phase-locked doublet components. The s-mmw source of the doublet radiation needs to provide the phase locking of the beat signal of the doublet components by a reference oscillator stabilised by a high Q crystal. As it was discussed before such spatial coherent radiation even subjected to multiple scattering processes at random surface structure of object 16 will produce enhanced visual quality images, which are physically totally equivalent to speckle-free images which would be obtained when the object is illuminated by spatially non-coherent radiation emitted from the position of the doublet radiation source 12a or 12b. Thereby diffusers may be used for creating diffuse illumination of the object that will additionally allow overcoming destructive effects of possible specular reflection of the doublet radiation by the object surface. It is important that such diffuser may be even a simple diffuser even not conceived for destroying the radiation spatial coherence. It allows using any natural diffuser (like ordinal room walls) for illumination of the observable scene. As the Fresnel lens is compact and light, and the doublet radiation images will exhibit high quality even only point like source is used, cheap hand-held portable systems may be developed for special kind of imaging goals outside a specially designed observable room of FIG. 55. For such portable system any type of wall nearby an observable individual or another object of interest may be used as a diffuser. The receiving apparatus of aforesaid Fresnel imaging systems needs to be provided by suitable demodulation modules.

Finally, if the doublet radiation will be first scattered by a coherence destroying diffuser such as an array of antenna-coupled modulated non-linear elements before impinging on the object, the receiving apparatus will be able to independently show multiple speckle free images, each of which is produced by radiation, scattered by particular element of the diffuser. It is obvious that the volume of information about the observable scene which can be produced by the proposed imaging system will be more than enough to detect the contraband located at any point of the scene.

VIII. Applications

The systems and methods described herein can be utilized in a variety of contexts. Millimeter wave active imaging has numerous applications. The ability to penetrate a solid substances like clothes, rocks, fog, dust, smoke, and light rain is at the root of several potential applications. The following paragraphs will discuss just of few of these contexts.

In a first example, the present invention can be used for security purposes to examine people for controlled substances, such as weapons and/or drugs, as two examples. This system can be implemented, for example, in airports, schools, courtrooms, or any of a practically infinite number of other places.

Figure 55:
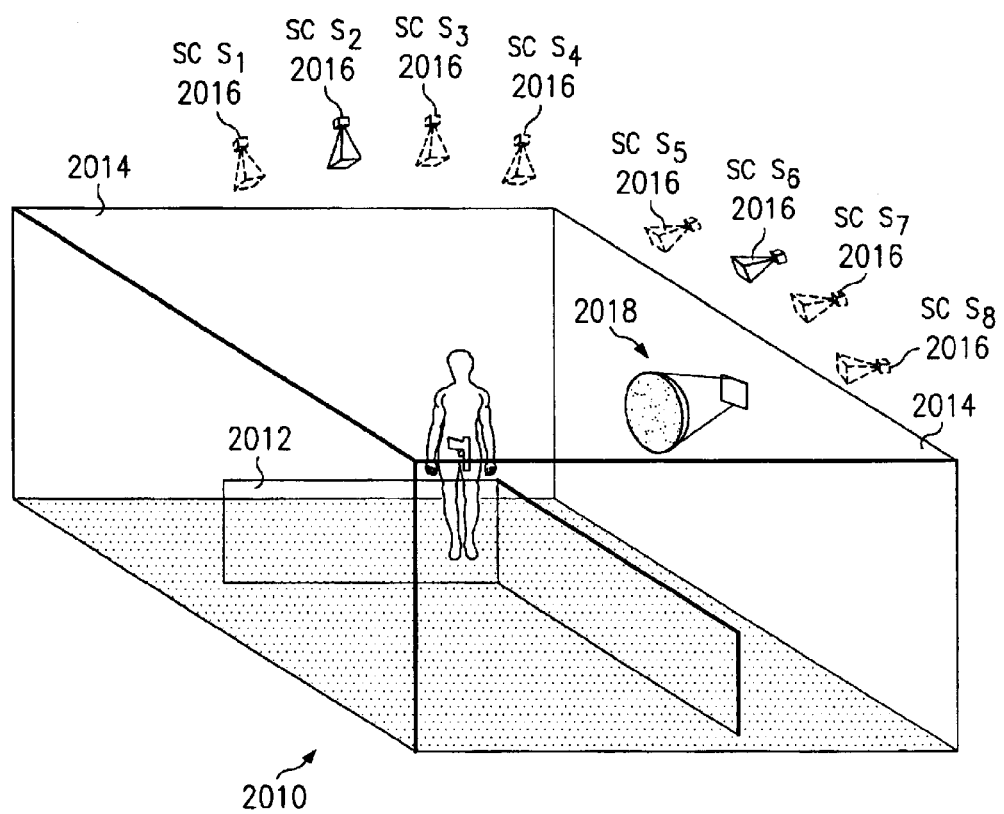
FIG. 55 illustrates an observation room for security applications.

FIG. 55 illustrates an observation room that can be used for this security purpose. To best organize the procedure, it may be useful to restrict the path of the human carriers to part of the observation special room by some device, such as railing 2012. The walls 2014 of such room 2010 may be covered by radiation coherence destroying diffusers (not shown), which are illuminated by a "polychromatic" radiation source 2016. The imaging system 2018 (or several systems) may be located for the optimal visualization of the carriers. All elements may be under computer control and act in real time. A special computer system intended for processing multiple partial images for fast and reliable recognition of masked objects can be utilized.

There are numerous other civilian applications. Civilian air transportation would benefit from systems, such as the autonomous landing guidance systems under development, that could aid pilots in landing in averse weather conditions. Because of the penetration at millimeter wave frequencies, imaging systems could be used to fight fires, by seeing through smoke. It might also be used for inland waterway navigation in fog. This same ability might make the system useful for remote sensing of earth resources or ice.

As the technology advances-and the activity of research in this area assures that it will other applications are likely to become apparent.

Other applications that make use of penetration of s-mmw through solids include de-mining applications. Millions of near surface buried mines are spread over thousands of mine fields. These near surface mines are covered with all kind of layered materials such as vegetation, rocks, all kind of sands penetrative for some parts of the s-mmw spectrum. Active s-mmw imaging of these mines may be a possible secure de-mining method.

Finally all kind of non-destructive testing methods for visualization of objects packaged by packaging material which are not transparent by IR or the visible part of the electromagnetic spectrum, can be developed on the base of active s-mmw imaging systems. As an example we refer to the semiconductor industry where metal interconnects between the chip and its non-transparent ceramic package can be visualized. In other applications, one can devise sorting techniques on the base of subsurface distinguishable features. In the food industry sub-surface features of vegetables, fruits, meat, . . . invisible for the eye can be revealed by active s-mmw imaging systems and leading to new sorting techniques. Other applications of s-mmw imaging could comprise preventive periodical testing of aging of constructions, which are vulnerable for the absorption of destroying liquids. When the liquid inside the construction can be revealed by the mmw spectrum and not by the eye, new testing techniques can be devised such that construction do not need to be disassembled or destroyed.

It is noted that different applications will require different features and therefore can be implemented at different costs. For example, in the security context, it may be sufficient to develop a system that provides a simple yes/no indication of the presence of weapons and/or drugs. A system like this that does not require a full image can be implemented more inexpensively than a system that provides a full image. As a result, not all of the features described herein must be utilized in every application.

While this invention has been described with reference to illustrative embodiments, this description is not intended to be construed in limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An s-mmw imaging system, comprising
  a non-rotating diffuser destroying a spatial coherence of radiation incident on the diffuser and directing the radiation towards a field of view, wherein the diffuser comprises a spatially distributed diffuser and wherein the diffuser comprises a plurality of spatially distributed point scatterers;
  at least one radiation source disposed to illuminate the diffuser, the at least one radiation source generating radiation having a wavelength between about 0.1 mm and about 10 mm;
  a quasi-optical element disposed between the field of view and a multi-element receiver, the quasi-optical element directing radiation from the field of view toward an imaging plane;
  said multi-element receiver disposed in the imaging plane, wherein particular ones of the receiver elements transform radiation into a set of electrical signals; and
  a processor coupled to receive the electrical signals from the receiver, the processor causing the point scatterers to be controlled based on information determined from the electrical signals.

2. The system of claim 1 wherein the diffuser comprises a two-dimensional array of point scatterers, each of the point scatterers having a position and orientation which can be independently changed in time relative to a reference plane.

3. The system of claim 1 wherein the point scatterers comprise conductive structures being loaded by impedances.

4. The system of claim 3 wherein magnitudes of the impedances of the loaded structures are time-varied due to modulation.

5. The system of claim 4 wherein said spatially distinct scatterers are modulated by signals exhibiting distinct modulation features.

6. The system of claim 5 wherein one of the distinct modulation features is the frequency of the modulation signals.

7. The system of claim 4 wherein the point scatterers are divided into sets and wherein each point scatterer within a set of point scatters is modulated by the same modulation signal.

8. The system of claim 7 wherein each set of point scatterers is frequency modulated by a unique modulating signal, wherein the frequencies of the modulation signals are distinct.

9. The system of claim 7 wherein the composition of each set of point scatterers can be dynamically changed.

10. The system of claim 3 wherein the conductive structures comprise antennae.

11. The system of claim 1 and further comprising a processor coupled to receive the electrical signals from the receiver, the processor generating resultant images from the electrical signals.

12. The system of claim 1 wherein the radiation directed from the diffuser toward the field of view comprises a set of multiple phase-independent partials being independently controllable and exhibiting distinct physical features and wherein the electrical signals include information relating to features of the partials.

13. The system of claim 1 wherein the radiation incident on the diffuser includes doublet spectral components.

14. The system of claim 1 wherein the spatially distributed point scatterers are disposed on a corrugated substrate.

15. The system of claim 1 wherein each of the point scatterers change the phase of scattered radiation independently of others of the point scatterers.

16. The system of claim 1 wherein each of the point scatterers change the frequency distribution of scattered radiation independently of others of the point scatterers.

17. A source of partially coherent radiation for illuminating a field of view, the source comprising:
  at least one non-movable diffuser destroying a spatial coherence of radiation being incident on the diffuser and directing the radiation towards a field of view, the diffuser including an array of independently controllable radiation scatterers; and
  at least one radiation emitting source being arranged to illuminate said diffuser with radiation;
  wherein each radiation scatterer comprises a static high-Q resonant scatterer exhibiting frequency resonance belonging to a particular frequency band and wherein the radiation emitting source comprises a radiation source that sweeps over the particular frequency band.

18. The radiation source of claim 17 wherein each of the radiation scatterers is electronically controllable.

19. The radiation source claim 18 wherein each of the radiation scatterers is controllable by a time-varying modulation signal.

20. The radiation source of claim 19 wherein said radiation scatterers are assigned into sets and wherein each radiation scatterer within a set of radiation scatterers is modulated in the same manner.

21. The radiation source of claim 20 wherein the sets are assigned according to an angle of incidence of radiation scattered by the diffuser.

22. The radiation source of claim 21 wherein the sets are dynamically assigned.

23. The radiation source of claim 19 wherein the modulation signal exhibits distinct modulation features for distinct scatterers.

24. The radiation source of claim 19 wherein the radiation scatterers are controlled by frequency-modulated modulation signals.

25. The radiation source of claim 17 wherein the radiation scatterers can be independently controlled by physically moving the point scatterers with respect to a reference plane.

26. The radiation source of claim 25 wherein each radiation scatterer is under piezoelectric control.

27. The radiation source of claim 25 wherein each radiation scatterer is under electromagnetic control.

28. The radiation source of claim 17 wherein each radiation scatterer comprises a conductive structure loaded by an impedance.

29. The radiation source of claim 28 wherein each radiation scatterer includes a resistive element.

30. The radiation source of claim 28 wherein each radiation scatterer includes an inductive element.

31. The radiation source of claim 28 wherein each radiation scatterer includes a capacitive element.

32. The radiation source of claim 17 wherein the at least one radiation emitting source is arranged to illuminate the diffuser with radiation having a wavelength between about 0.1 mm to about 10 mm.

33. The radiation source of claim 17 wherein the radiation scatterers are disposed on a corrugated substrate.

34. The radiation source of claim 17 wherein the radiation scatterers have polarization selective characteristics.

35. The radiation source of claim 17 wherein the radiation scatterers have frequency selective characteristics.

36. The radiation source of claim 17 wherein each radiation scatterer is controlled by an electric signal.

37. The radiation source of claim 17 wherein each radiation scatterer is controlled by an optical signal.

38. The radiation source of claim 17 wherein the radiation scatterers comprise antennas with closely spaced frequency resonances that are spatially clustered in given geometrical profiles.

39. A millimeter wave system comprising:
   a source of radiation, the radiation comprising a set of independently controllable radiation components, each radiation component comprising a doublet that includes two spectral lines, and each radiation component being labeled by a given frequency shift between the two spectral lines;
   a receiver including an array of receiver elements disposed to receive the radiation emitted by the source, the receiver transforming the received radiation into an array of electrical signals; and
   a processing system coupled to receive the array of electrical signals and for decoding the array of electrical signals based on the labels of the radiation components.

40. The system of claim 39 wherein the processing system is coupled to the source of radiation to provide instructions on how to control the radiation components.

41. The system of claim 39 wherein the frequency difference between the two spectral lines is modulated.

42. The system of claim 39 wherein the central frequency of the two spectral lines is swept in time.

43. The system of claim 39 wherein the two spectral lines comprise a co-polarized doublet and wherein the source of radiation comprises:
   a pair of voltage controlled oscillators operating at a s-mmw frequency and having a first characteristic polarization state;
   a set of load-modulated point scatterers that are illuminated by the voltage controlled oscillators, the set of load-modulated point scatterers being preferentially sensitive to the first characteristic polarization state;
   wherein the load of each point scatterer is modulated with a time varying signal; and
   wherein the scattered radiation is directed to an object being imaged.

44. The system of claim 43 wherein the time varying signal is a periodic signal.

45. The system of claim 39 wherein the source of radiation is in a substrate configuration, the source further comprising means to combine the radiation of the two spectral lines of each component.

46. The system of claim 39 wherein the source of radiation is in a waveguide configuration, the source further comprising means to combine the radiation of the two spectral lines of each component.

47. The system of claim 39 wherein the two spectral lines have co-polarization characteristics.

48. The system of claim 39 wherein the two spectral lines have cross-polarization characteristics.

49. The system of claim 39 wherein the receiver elements comprise mixers which generate difference frequency signals for the radiation components.

50. The system of claim 39 wherein the source of radiation includes:
   a first voltage controlled oscillator operating at a first frequency;
   a second voltage controlled oscillator operating at a second frequency; and
   an embedded mixer;
   wherein the combined energy of the first and second voltage controlled oscillators is divided into two unequal parts, a major part being used to direct to a destination and a minor part being used to control a difference frequency between the two spectral lines by mixing the minor part in the embedded mixer.

51. The system of claim 39 wherein the two spectral lines comprise a cross-polarized doublet and wherein the source of radiation includes:
   a first set of load-modulated point scatterers, the first set exhibiting a first polarization state;
   a second set of load-modulated point scatterers, the second set exhibiting a second polarization state, the first polarization state being orthogonal to the second polarization state; and
   a voltage controlled oscillator operating at an s-mmw frequency having a third characteristic polarization state which differs from the said first and second polarization states, the voltage controlled oscillator illuminating the first and second sets of load-modulated point scatterers.

52. A method for creating radiation that includes a polarized doublet, the method including:
   emitting radiation at a first s-mmw frequency;
   emitting radiation at a second s-mmw frequency, wherein the difference between the first s-mmw frequency and the second s-mmw frequency is much smaller than the average of the first s-mmw frequency and the second s-mmw frequency;
   controlling the difference between the first s-mmw frequency and the second s-mmw frequency;
   polarizing the radiation at the first s-mmw frequency into a first characteristic polarization;
   polarizing the radiation at the s-mmw frequency into a second characteristic polarization;
   combining the radiation at the first s-mmw frequency and the radiation at the second s-mmw frequency; and
   directing the combined radiation to a destination.

53. The method of claim 52 wherein the first polarization is essentially equal to the second polarization.

54. The method of claim 52 wherein the first polarization is essentially orthogonal to the second polarization.

55. The method of claim 52 wherein the combined radiation is divided into two unequal parts, a major part being directed to the destination and a minor part being used to control the difference frequency.

56. The method of claim 52 and further comprising changing average of the first s-mmw frequency and the second s-mmw frequency.

57. The method of claim 52 and further comprising modulating the difference between the first s-mmw frequency and the second s-mmw frequency.

58. The method of claim 52 wherein the method is performed in a waveguide configuration.

59. The method of claim 52 wherein the method is performed in a planar substrate configuration.

60. A method of creating radiation that includes a cross-polarized doublet, the method comprising:

providing a voltage controlled oscillator operating at a first s-mmw frequency;

directing energy of the oscillator to uniformly illuminate first and second sets of load-modulated point scatterers, the first set exhibiting a first polarization state and the second set exhibiting a second polarization state, wherein the first polarization state is orthogonal to the second polarization state;

polarizing the oscillator in a third characteristic polarization state;

positioning the first and second sets of point scatterers such that the first and second polarization state substantially differs from the third characteristic polarization state;

modulating the load of the first scatterer with a first time varying signal;

modulating the load of the second scatterer with a second time varying signal, wherein the ground harmonic of first time varying signal essentially differs from any harmonic of the second harmonic time varying signal; and scattering radiation from the first and second sets of point scatterers.

61. The method of claim 60 wherein the first and second time varying signals are periodic signals.

62. The method of claim 61 wherein the sum of the ground harmonics of the first periodic signal and the second periodic signal is equal to a doublet frequency difference.

63. The method of claim 61 wherein the difference of the ground harmonics of the first periodic signal and the second periodic signal is equal to a doublet frequency difference.

64. The method of claim 61 wherein the periodic signals are binary signals.

65. The method of claim 61 wherein the periodic signals are harmonic signals.

66. The method of claim 61 and further comprising controlling the difference frequency between the periodic signals by dividing the energy of both periodic signals in unequal parts, a major part being used to drive first and second loads and the minor part being used to control the difference frequency.

67. A millimeter wave transmitter-receiver apparatus for transmitting and receiving image or communication data comprising:

a source of radiation, the radiation comprising a set of independently controllable radiation components, each radiation component comprising a doublet that includes two spectral lines, and each radiation component being labeled by a given frequency shift between the two spectral lines;

a receiver including an array of receiver elements disposed to receive the radiation emitted by the source, the receiver transforming the received radiation into an array of electrical signals; and a processing system coupled to receive the array of electrical signals and for decoding the array of electrical signals based on the labels of the radiation components.

68. The apparatus of claim 67 wherein the processing system is coupled to the source of radiation to provide instructions on how to control the radiation components.

69. The apparatus of claim 67 wherein the frequency difference between the two spectral lines is modulated.

70. The apparatus of claim 67 wherein the central frequency of the two spectral lines is swept in time.

71. The apparatus of claim 67 wherein the two spectral lines comprise a doublet and wherein the source of radiation comprises:

at least one pair of voltage controlled oscillators operating at different s-mmw frequencies;

a plurality of paired couplers each of which is individually coupled to an output of one of the voltage-controlled oscillators (VCOs) for dividing VCO radiation into a major portion for transmitting in free space and a minor portion for mixing;

a first mixer for mixing the minor radiation portion the VCO radiation to produce a first beat signal;

a phase locked loop (PLL) circuit providing phase-locking of the first beat signal by the reference signal, wherein one input of the PLL circuit is supplied by the first beat signal, another PLL circuit input is supplied by the reference signal and an output correction voltage produced by the PLL circuits is provided to a frequency correcting driving voltage input of one of the VCOs; and an antenna system to transmit the major radiation portions produced by the VCOs in free space.

72. An s-mmw imaging system, comprising:

a non-rotating diffuser destroying a spatial coherence of radiation incident on the diffuser and directing the radiation towards a field of view, wherein the radiation incident on the diffuser includes doublet spectral components and wherein the radiation incident on the diffuser is modulated by modulating a spectral shift between doublet spectral components;

at least one radiation source disposed to illuminate the diffuser, the at least one radiation source generating radiation having a wavelength between about 0.1 mm and about 10 mm;

a quasi-optical element disposed between the field of view and a multi-element receiver, the quasi-optical element directing radiation from the field of view toward an imaging plane; and said multi-element receiver disposed in the imaging plane, wherein particular ones of the receiver elements transform radiation into a set of electrical signals.

73. The system of claim 72 wherein the diffuser comprises a spatially distributed diffuser.

74. The system of claim 73 wherein the diffuser comprises a plurality of spatially distributed point scatterers.

75. The system of claim 74 and further comprising a processor coupled to receive the electrical signals from the receiver, the processor causing the point scatterers to be controlled based on information determined from the electrical signals.

76. The system of claim 74 wherein the diffuser comprises a two-dimensional array of point scatterers, each of the point scatterers having a position and orientation which can be independently changed in time relative to a reference plane.

77. The system of claim 74 wherein the point scatterers comprise conductive structures being loaded by impedances.

78. The system of claim 72 and further comprising a processor coupled to receive the electrical signals from the receiver, the processor generating resultant images from the electrical signals.

79. The system of claim 72 wherein the radiation directed from the diffuser toward the field of view comprises a set of multiple phase-independent partials being independently controllable and exhibiting distinct physical features and wherein the electrical signals include information relating to said features of the partials.

* * * * *